US009669085B2

(12) United States Patent  
Suradhat et al.

(10) Patent No.: US 9,669,085 B2  
(45) Date of Patent: Jun. 6, 2017

(54) NEEDLE-FREE ADMINISTRATION OF PRRSV V

(56) References Cited

OTHER PUBLICATIONS

Xue Q, Zhao YG, Zhou YJ, Qiu HJ, Wang YF, Wu DL, Tian ZJ, Tong GZ. Immune responses of swine following DNA immunization with plasmids encoding porcine reproductive and respiratory syndrome virus ORFs 5 and 7, and porcine IL-2 and IFNgamma. Vet Immunol Immunopathol. Dec. 8, 2004;102(3):291-8.*

Martelli P, Cordioli P, Alborali LG, Gozio S, De Angelis E, Ferrari L, Lombardi G, Borghetti P. Protection and immune response in pigs intradermally vaccinated against porcine reproductive and respiratory syndrome (PRRS) and subsequently exposed to a heterologous European (Italian cluster) field strain. Vaccine. Apr. 30, 2007;25(17):3400-8. Epub 2007.*

Martelli P, Gozio S, Ferrari L, Rosina S, De Angelis E, Quintavalla C, Bottarelli E, Borghetti P. Efficacy of a modified live porcine reproductive and respiratory syndrome virus (PRRSV) vaccine in pigs naturally exposed to a heterologous European (Italian cluster) field strain: Clinical protection and cell-mediated immunity. Vaccine. Jun. 8, 2009;27(.*

Barfoed AM, Kristensen B, Dannemann-Jensen T, Viuff B, Bøtner A, Kamstrup S, Blixenkrone Møller M. Influence of routes and administration parameters on antibody response of pigs following DNA vaccination. Vaccine. Mar. 29, 2004;22(11-12):1395-405.*

Biojector® 2000. Bioject Fact sheet. 2012.*

Murtaugh et. al. GenBank Acc. No. U87392.3, ORF7 GenBank Acc. No. AAD12131, updated Nov. 17, 2000.*

Kwang J, Zuckermann F, Ross G, Yang S, Osorio F, Liu W, Low S. Antibody and cellular immune responses of swine following immunisation with plasmid DNA encoding the PRRS virus ORF's 4, 5, 6 and 7. Res Vet Sci. Oct. 1999;67(2):199-201.*

Gurunathan S, Klinman DM, Seder RA. DNA vaccines: immunology, application, and optimization. Annu Rev Immunol. 2000;18:927-74.*

Chase CCL, Daniels CS, Garcia R, Milward F, Nation T. Needle-free injection technology in swine: Progress toward vaccine efficacy and pork quality. J Swine Health Prod. 2008;16(5):254-261.*

Wongyanin P, Buranapraditkun S, Thanawongnuwech R, Suradhat S. Induction of Porcine Interleukin-10 by Nucleocapsid Protein of Porcine Reproductive and Respiratory Syndrome Virus (PRRSV). Proceedings 8th Chula. Univ. Vet. Sci. Ann. Con., Apr. 3, 2009. P5.*

Suradhat S, Wongyanin P, Kesdangsakonwut S, Teankum K, Lumyai M, Triyarach S, Thanawongnuwech R. A novel DNA vaccine for reduction of PRRSV-induced negative immunomodulatory effects: A proof of concept. Vaccine. Jul. 31, 2015;33(32):3997-4003.*

Rompato G, Ling E, Chen Z, Van Kruiningen H, Garmendia AE. Positive inductive effect of IL-2 on virus-specific cellular responses elicited by a PRRSV-ORF7 DNA vaccine in swine. Vet Immunol Immunopathol. Jan. 15, 2006;109(1-2):151-60.*

Díaz I, Ganges L, Galindo-Cardiel I, Tarradas J, Alvarez B, Lorca-Oró C, Pujols J, Gimeno M, Darwich L, Domingo M, Domínguez J, Mateu E. Viral Immunol. Feb. 2013;26(1):93-101.*

Suradhat, Sanipa. Taming PRRSV: Revisiting the control strategies and vaccine design. Virus Research 154 (2010) 133-140.

Albina E., et al. Veterinary Microbiology 55 (1997) 309-3 16. Epidemiology of porcine reproductive and respiratory syndrome (PRRS): An overview.

Bautista EM et al. Seroprevalence of PRRS virus in the US. Swine Health and Production—Nov. and Dec. 1993.

Bautista EM et al. Structural polypeptides of the American (VR-2332) strain of porcine reproductive and respiratory syndrome virus. Arch Virol (1996) 141:1357-1365.

Benfield DA et al. J Vet Diagn Invest 4: 127-133 (1992). Characterization of swine infertility and respiratory syndrome (SIRS) virus (isolate ATCC VR-2332).

Brierley I. Ribosomal frameshifting on viral RNAs. Journal of General Virology (1995), 76, 1885 1892.

Cho SH et al. J Vet Diagn Invest 5:259-260 (1993). Seroprevalence of indirect fluorescent antibody to porcine reproductive and respiratory syndrome virus in selected swine herds.

Collins JE et al. J Vet Diagn Invest 4: 117-126 (1992). Isolation of swine infertility and respiratory syndrome virus (isolate ATCC VR-2332) in North America and experimental reproduction of the disease in gnotobiotic pigs.

De Vries, AA et al. Seminars in Virology 8, 33-47 (1997) The Genome Organization of the Nidovirales: Similarities and Differences between Arteri-, Toro-, and Coronaviruses.

Den Boon et al. Equine arteritis virus is not a togavirus but belongs to the coronaviruslike superfamily. J.Virol. 1991, 65(6):2910.

Dewey CE et al. The reproductive performance of sows after PRRS vaccination depends on stage of gestation. Preventive Veterinary Medicine 40 (1999) 233-241.

Done et al. Porcine Reproductive and Respiratory Syndrome (PRRS): A Review, With Emphasis on Pathological, Virological and Diagnostic Aspects. Br. vet. J. (1996). 152, 153.

Drew TW et al. Production, characterization and reactivity of monoclonal antibodies to porcine reproductive and respiratory syndrome virus. Journal of General Virology (1995), 76, 1361-1369.

Faaberg KS et al. The envelope proteins of lactate dehydrogenase-Elevating Virus and their membrane topography. Virol. 212. 512-525 (1995).

Faaberg KS et al. Disulfide Bonds between Two Envelope Proteins of Lactate Dehydrogenase-Elevating Virus Are Essential for Viral Infectivity. Journal of Virology, Jan. 1995, p. 613-617.

Gonin P et al. A nonstructural and antigenic glycoprotein is encoded by ORF3 of the IAF-Klop strain of porcine reproductive and respiratory syndrome virus. Arch Virol (1998) 143: 1927-1940.

Gonin P et al. Seroneutralization of PRRSV correlated with antibody response to the GP5 major envelope glycoprotein. J Vet Diagn Invest 11:20-26 (1999).

Halbur PG et al. Comparison of pathogenicity of two US PRRSV isolates with that of the Lelystad virus. Vet Pathol32:648-660 (1995).

Heinen E et al. Isolation of cytopathogenic virus from case of PRRS and its characterization as parainfluenza virus type 2. Arch Virol (1998) 143: 2233-2239.

Kwang J et al. Antibody and cellular immune response of swine following immunisation with plasmid DNA encoding PRRSV ORFs 4, 5, 6 and 7. Research in Veterinary Science 1999, 67, 197-199.

Mardassi H et al. Intracellular synthesis processing and transport of proteins encoded by ORFs 5 to 7 of PRRSV. Virology 221, 98-112 (1996).

Mardassi H et al. Molecular analysis of ORFs 3 to 7 of PRRSV Quebec reference strain. Arch Virol (1995) 140:1405-1418.

Meng XJ et al. A nested set of 6 to 7 subgenomic mRNAs is formed in cells infected with different isolates of PRRSV. Journal of General Virology (1996), 77, 1265-1270.

Meulenberg JJM et al. Identification and Characterization of a Sixth Structural Protein of Lelystad Virus. Virology 225, 44-51 (1996).

Meulenberg JJM et al. Characterization of Proteins Encoded by ORFs 2 to 7 of Lelystad Virus. Virology 206, 155-163 (1995).

Burtaugh MP et al. Comparison of the structural protein coding sequences of the VR-2332 and Lelystad virus strains of the PRRS virus. ArchVirol (1995) 140:1451-1460.

Nakamine M et al. Dual infection of enterotoxigenic E. coli and PRRSV observed in weaning pigs that died suddenly. J. Vet. Med. Sci. 60(5): 555-561 1998.

Nelsen CJ et al. Porcine Reproductive and Respiratory Syndrome Virus Comparison: Divergent evolution on two continents. J. Virol. 1999, 73(1):270.

Nelson EA et al. Differentiation of U.S. and European isolates of porcine reproductive and respiratory syndrome virus by monoclonal antibodies. J. Clin. Microbiol. 1993, 31(12):3184.

Panicali & Paoletti. Construction of poxviruses as cloning vectors Insertion of the thymidine kinase gene from herpes simplex virus into the DNA of infectious vaccinia virus. PNAS USA vol. 79, pp. 4927-4931, Aug. 1982.

Perkus ME et al. Cloning and Expression of Foreign Genes in Vaccinia Virus, Using a Host Range Selection System. Journal of Virology, Sep. 1989. p. 3829-3836.

(56) References Cited

OTHER PUBLICATIONS

Pirzadeh and Dea. Immune response in pigs vaccinated with plasmid DNA encoding ORF5 of porcine reproductive and respiratory syndrome virus. Journal of General Virology (1998), 79, 989-999.

Pirzadeh et al. Genomic and Antigenic Variations of Porcine Reproductive and Respiratory Syndrome Virus Major Envelope $GP_5$ Glycoprotein. Can J Vet Res 1998; 62: 170-177.

Pirzadeh and Dea. Monoclonal antibodies to the ORF5 product of porcine reproductive and respiratory syndrome virus define linear neutralizing determinants. Journal of General Virology (1997), 78, 1867-73.

Plana-Duran J et al. Baculovirus Expression of Proteins of Porcine Reproductive and Respiratory Syndrome Virus Strain Olot/91. Involvement of ORF3 and ORF5 Proteins in Protection. Virus Genes 14:1, 19±29, 1997.

Plana-Duran J et al. 1997. Efficacy of an inactivated vaccine for prevention of reproductive failure induced by porcine reproductive and respiratory syndrome virus. Vet Microbiol 55:361-370.

Sirinarumitr T, Zhang Y, Kluge JP, Halbur PG, Paul PS. 1998. A pneumo- virulent United States isolate of porcine reproductive and respiratory syndrome virus induces apoptosis in bystander cells both in vitro and in vivo. J Gen Virol 79:2989-2995.

Snijder E., van Tol H., Pedersen K.W., Raamsman M.J.B., and de Vries A.A.F. 1999. Identification of a novel structural protein of arteri viruses. J. Virol. 73, 6335-6345.

Suarez, P et al. 1996. Open reading frame 5 of porcine reproductive and respiratory syndrome virus as a cause of virus-induced apoptosis. J. Virol. 70: 2876-2882. 69. Sur JH, Doster AR, Osorio FA. 1998. Apoptosis induced in vivo during acute infection by porcine reproductive and respiratory syndrome virus. Vet Pathol 35:506-514.

Thacker EL et al. 1999. Mycoplasma hyopneumoniae potentiation of porcine reproductive and respiratory syndrome virus-induced pneumonia. J Clin Microbiol 37:620-627.

Nieuwstadt AP et al. Proteins encoded by open reading frames 3 and 4 of the genome of Lelystad virus (Arteriviridae) are structural proteins of the virion. J. Virol. 1996, 70(7):4767.

van Woensel PA et al. 1998a. Effect on viraemia of an American and a European serotype PRRSV vaccine after challenge with European wild-type strains of the virus. Vet Rec 142:510-512. 81. van Woensel PA, Liefkens K, Demaret S. 1998b. European serotype PRRSV vaccine protects against European serotype challenge whereas an American serotype vaccine does not. Adv Exp Med Biol 440:713-718.

Weiland E et al. 1999. Monoclonal antibodies to the GP5 of porcine reproductive and respiratory syndrome virus are more effective in virus neutralization than monoclonal antibodies to the GP4. Vet Microbiol 66:171-186.

Wensvoort, G.C. et al. 1991. Mystery swine disease in The Netherlands: the isolation of Lelystad virus. Vet Q. 13: 121-130.

Yeager, M.J et al. 1993. Evidence for the transmission of porcine reproductive and respiratory syndrome (PRRS) virus in boar semen. Swine Health Prod. 1(5): 7-9.

Yoon KJ et al. 1994. Assessment of the biological significance of antibody dependent enhancement (ADE) of porcine epidemic abortion and respiratory syndrome (PEARS) virus infection in passively immunized pigs. Proc. 13 Int. Pig Vet. Soc. Congress, p69.

Zimmermann, JJ et al. 1997. General Overview of PRRSV: A perspective from the United States. Veterinary Microbiology 55: 187-196.

Mengeling WL et al. The porcine reproductive and respiratory syndrome quandary. Part II: Vaccines and vaccination strategy. Journal of Swine Health and Production—May and Jun. 2005.

Suradhat, Sanipa (Applicant) Poster was presented in the Annual meeting of the Thailand Research Fund (TRF) in Oct. 2010. The meeting was Internal/Private (not open to public) for the TRF scholars and the researchers who received TRF grants. Applicants are happy to provide any additional information necessary for the Examiner to evaluate the relevance of this reference.

* cited by examiner

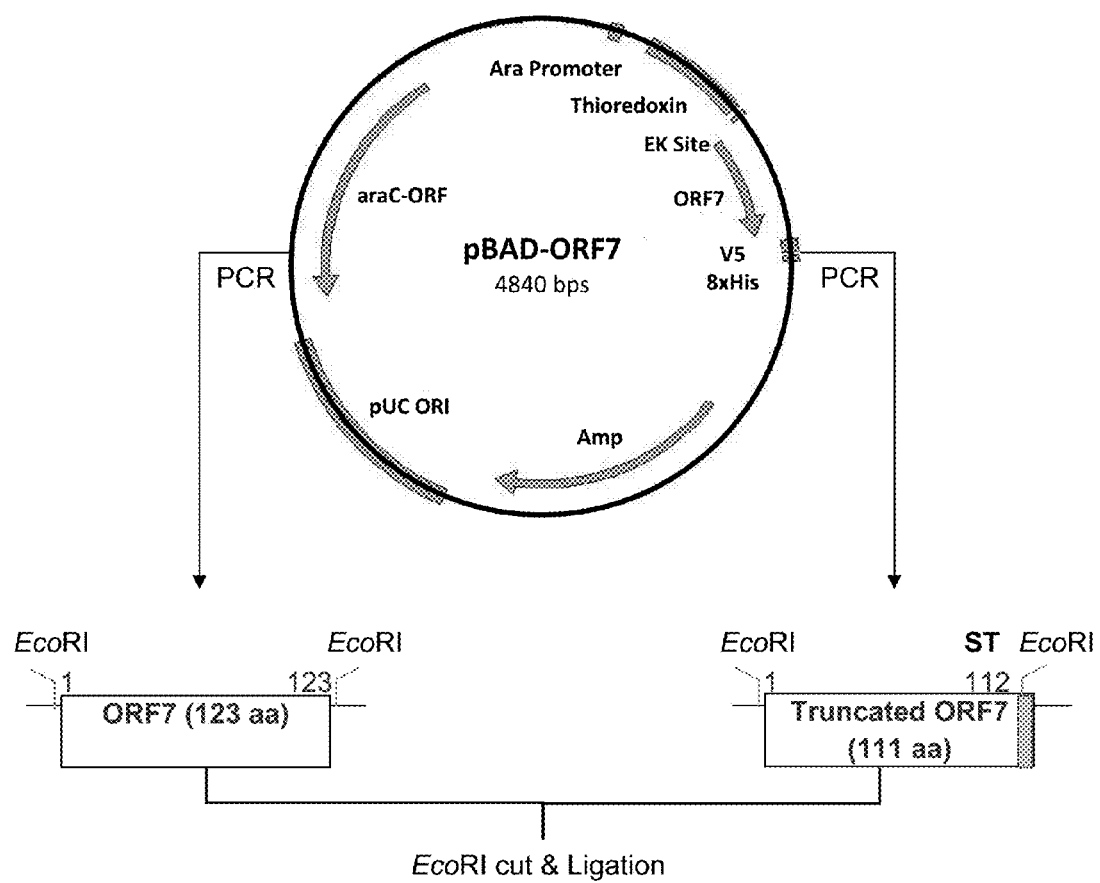
FIG. 1 (1/2)

FIG. 1 (2/2)
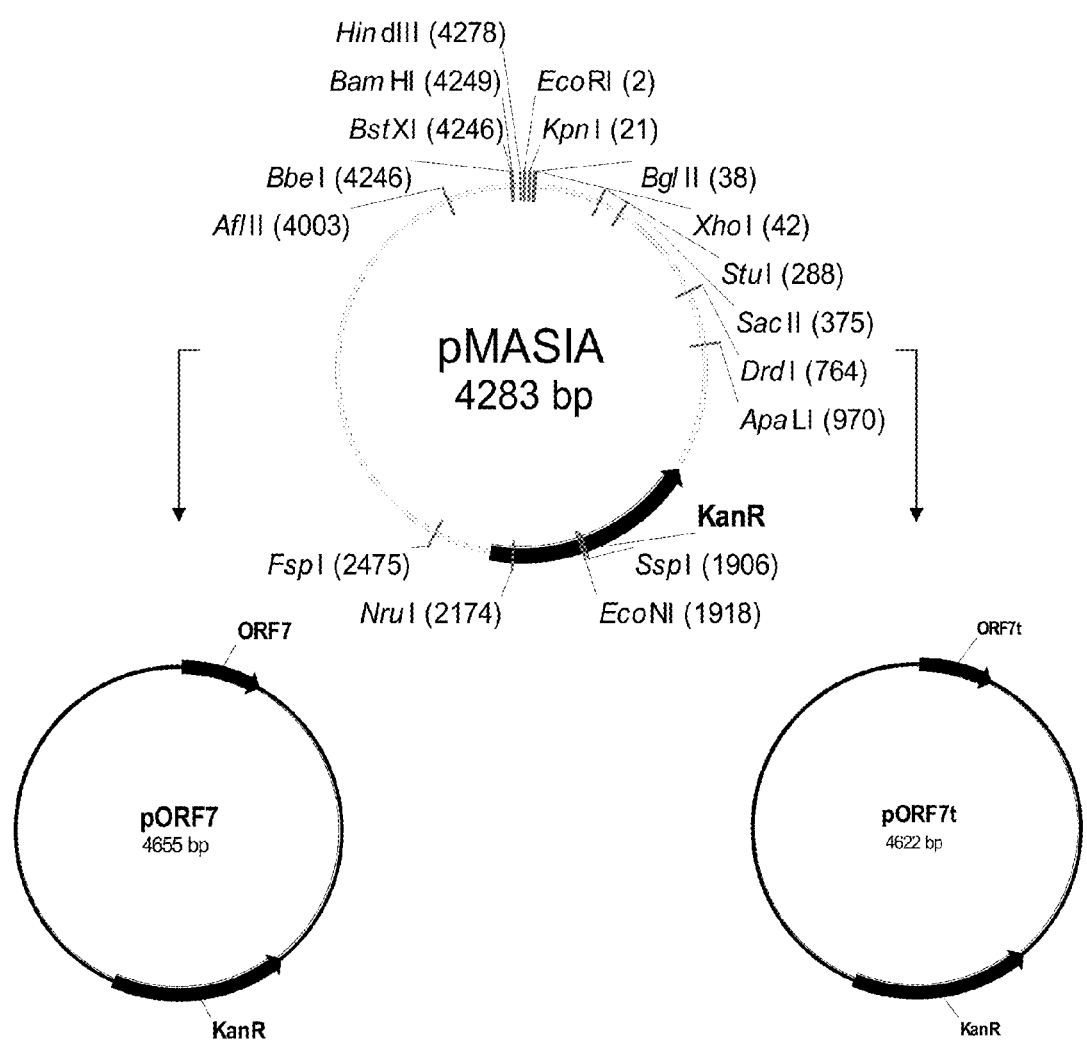

FIG. 2

```
US       MPNNNGKQQKRKKGDGQPVNQLCQMLGKIIAQQNQSRGKGPGKKNKKKNPEKPHFPLATE 60
01NP1.2  MPNNNGKQQKRKKGDGQPVNQLCQMLGKIIAQQNQSRGKGPGKKNKKKNPEKPHFPLATE 60
pBAD     MPNNNGKQQKRKKGDGQPVNQLCQMLGKIIAQQNQSRGKGPGKKNKKKNPEKPHFPLATE 60
         ************************************************************

US       DDVRHHFTPSERQLCLSSIQTAFNQGAGTCTLSDSGRISYTVEFSLPTHHTVRLIRVTAS 120
01NP1.2  DDVRHHFTPSERQLCLSSIQTAFNQGAGTCTLSDSGRISYTVEFSLPTHHTVRLIRVTAS 120
pBAD     DDVRHHFTPSERQLCLSSIQTAFNQGAGTCTLSDSGRISYTVEFSLPTHHTVRLIRVTAS 120
         ************************************************************

US       PSA 123
01NP1.2  PSA 123
pBAD     PSA 123
         ***

01NP1    MPNNNGKQQKRKKGDGQPVNQLCQMLGKIIAQQNQSRGKGPGKKNKKKNPEKPHFPLATE 60
ORF7t    MPNNNGKQQKRKKGDGQPVNQLCQMLGKIIAQQNQSRGKGPGKKNKKKNPEKPHFPLATE 60
         ************************************************************

01NP1    DDVRHHFTPSERQLCLSSIQTAFNQGAGTCTLSDSGRISYTVEFSLPTHHTVRLIRVTAS 120
ORF7t    DDVRHHFTPSERQLCLSSIQTAFNQGAGTCTLSDSGRISYTVEFSLPTHHTV-------- 112
         ***************************************************

01NP1    PSA 123
ORF7t    ---
```

FIG. 3

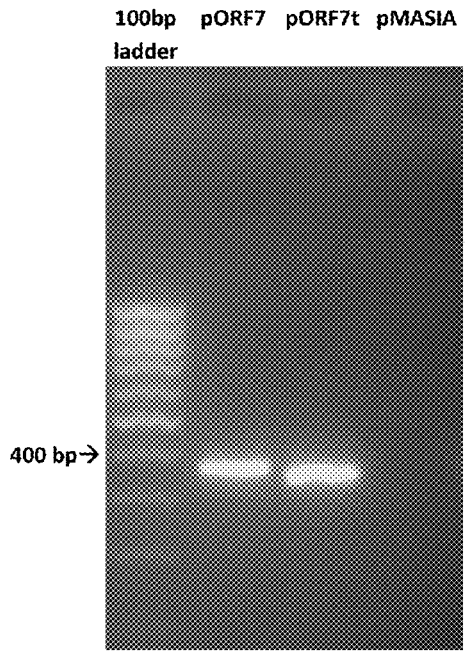

| Plasmid | Size (bp) | NcoI restriction sites | Size of the fragments (bp) |
|---|---|---|---|
| Null | 4283 | 21, 3072, 4181 | 123, 1109, 3051 |
| pORF7 | 4655 | 393, 3444, 4553 | 495, 1109, 3051 |
| pORF7t | 4622 | 360, 3411, 4502 | 463, 1109, 3051 |

FIG. 6
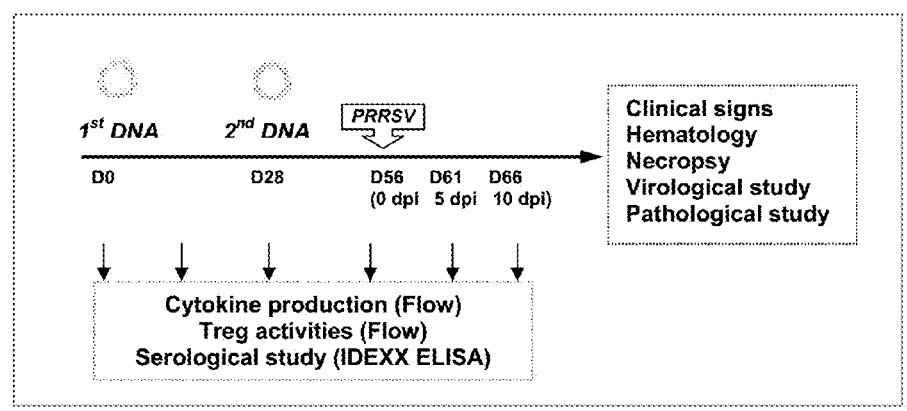
FIG. 7
A.
B.
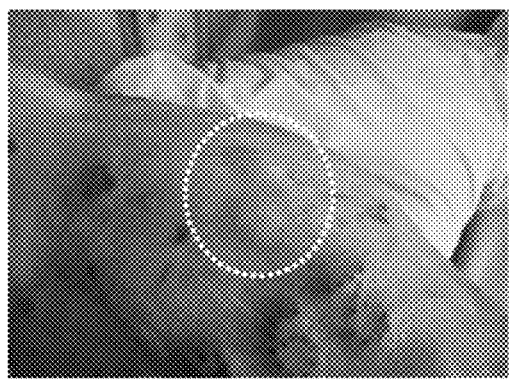

A. Overview of the Experimental Plan

B.

FIG. 12 (1/2)
A
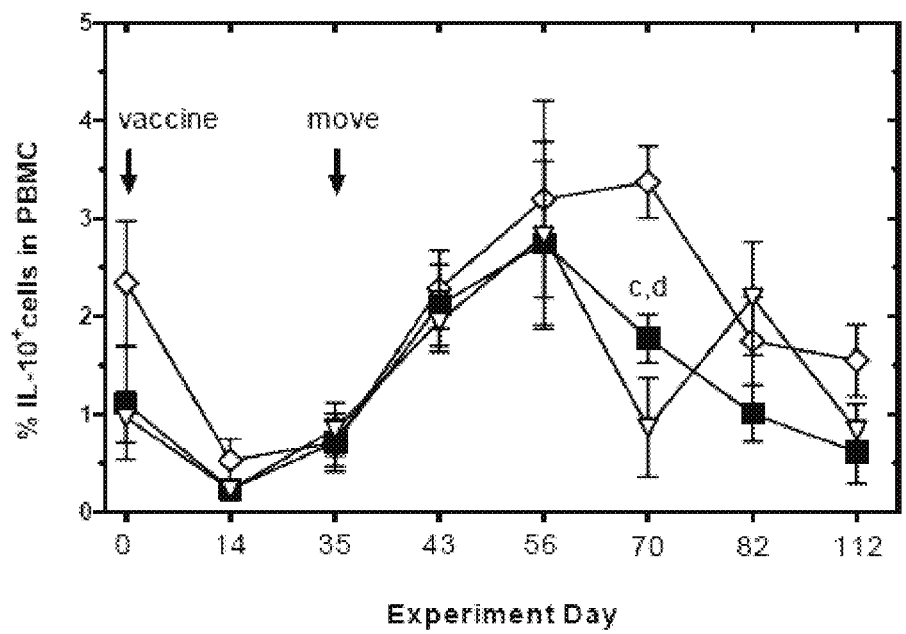
B
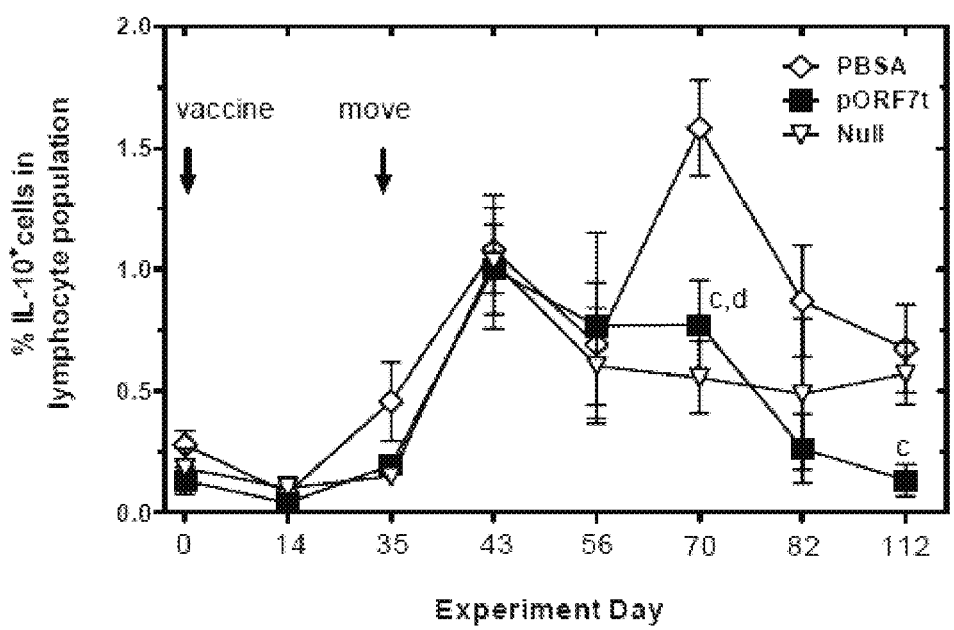

FIG. 12 (2/2)
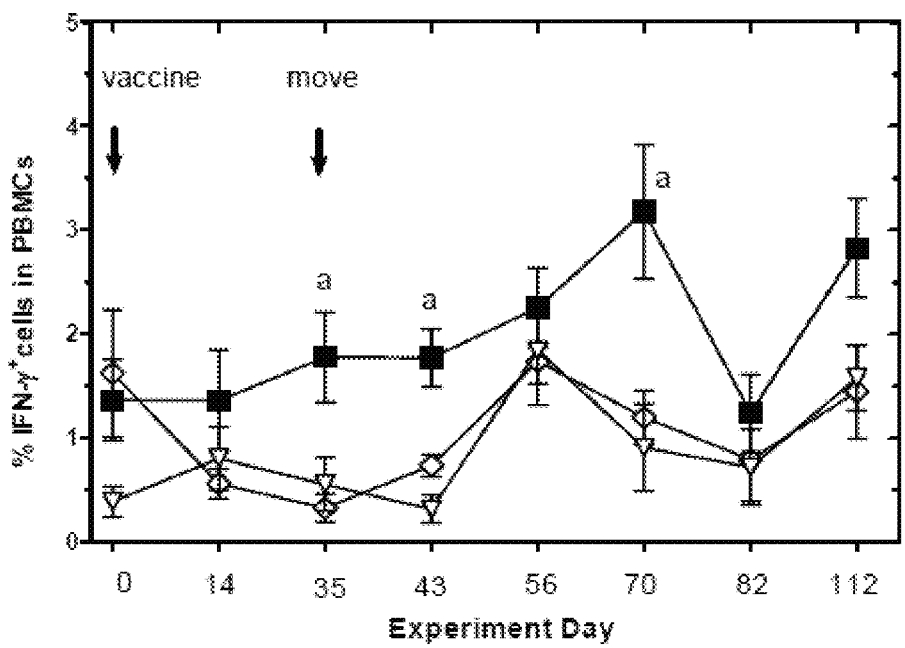
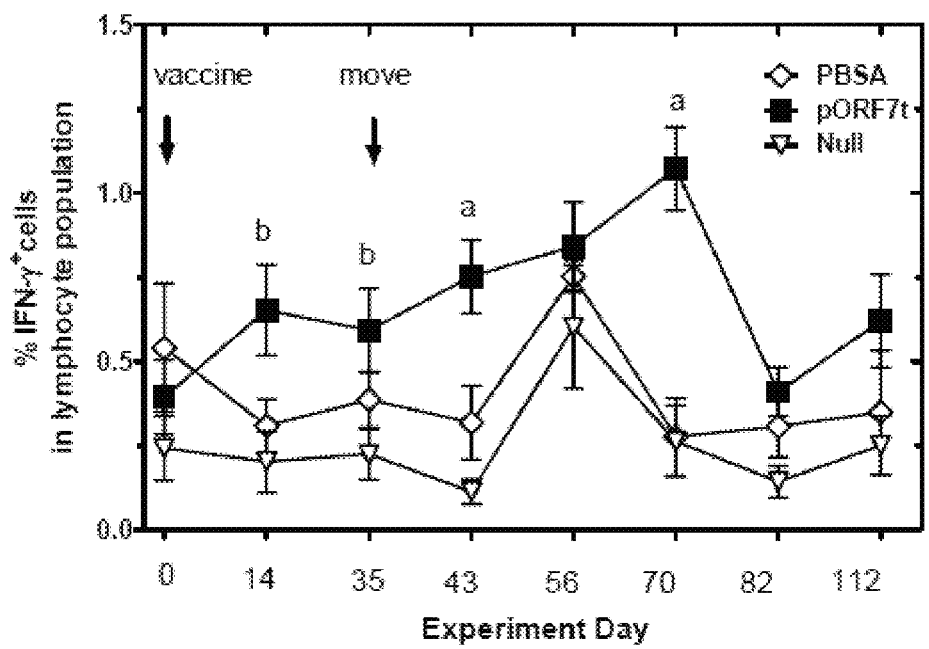

FIG. 13
A.
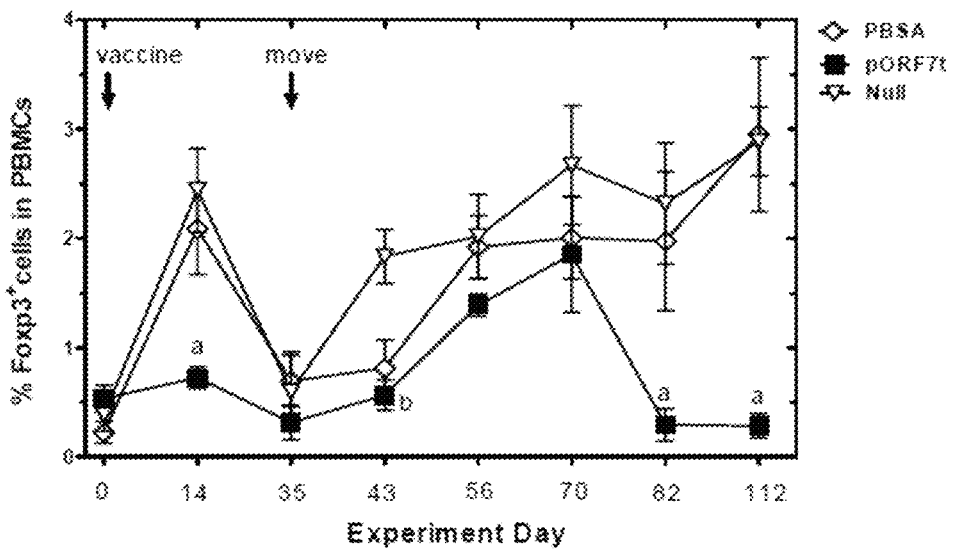
B.
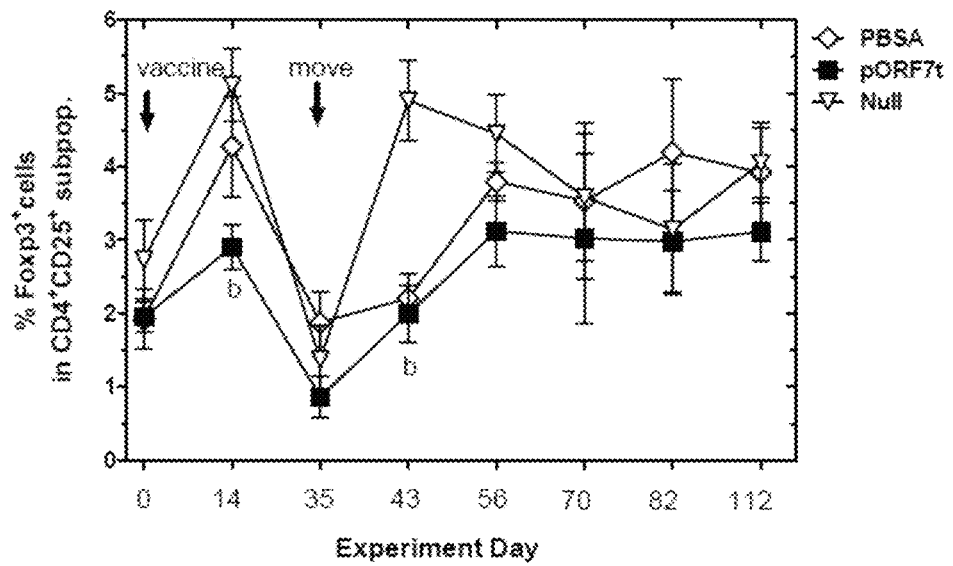

FIG. 14 (1/2)
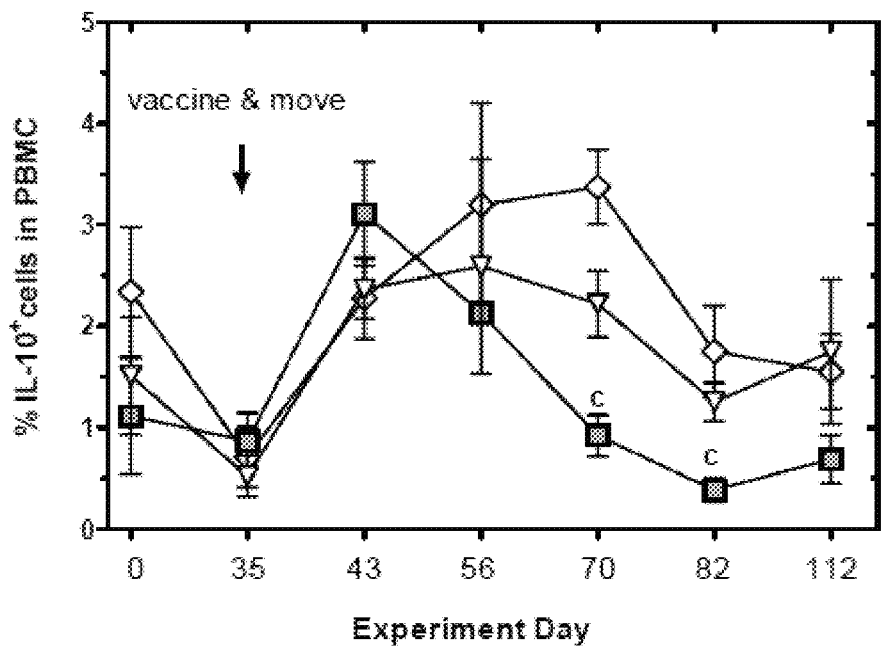
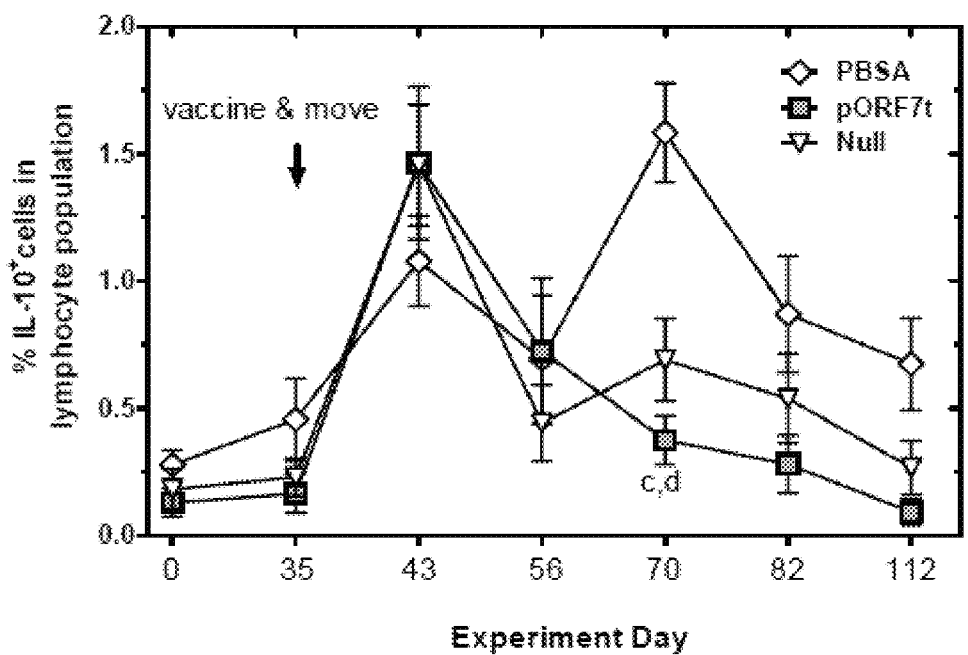

FIG. 14 (2/2)
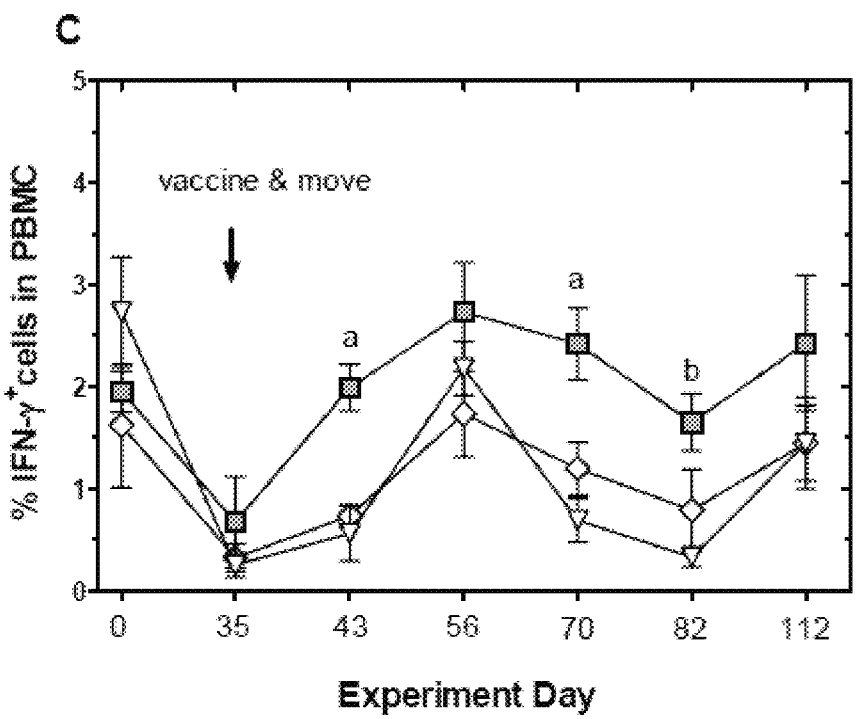
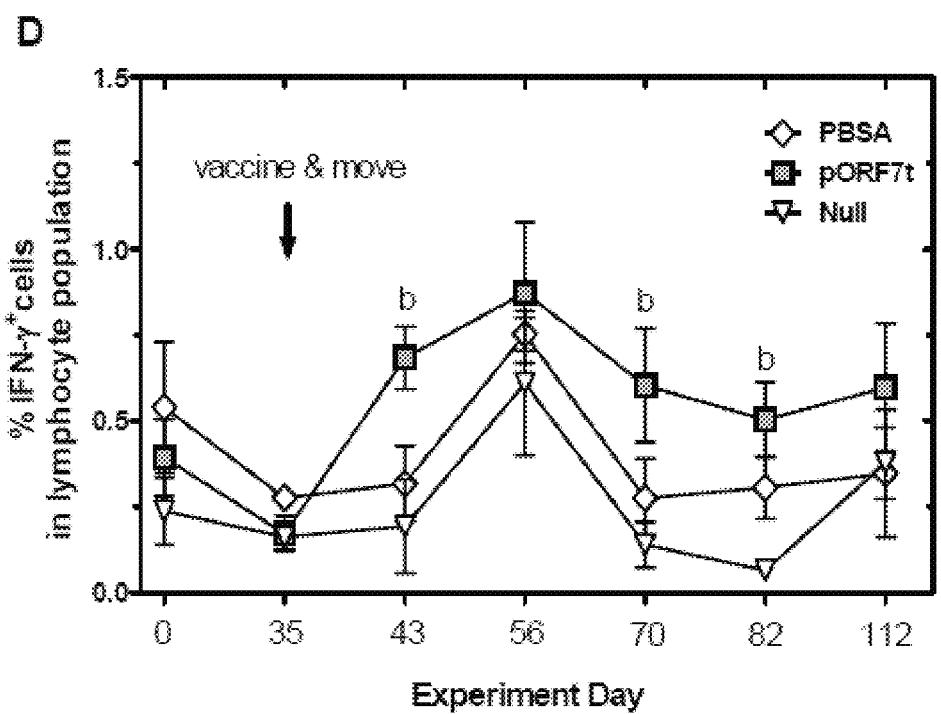

FIG. 15
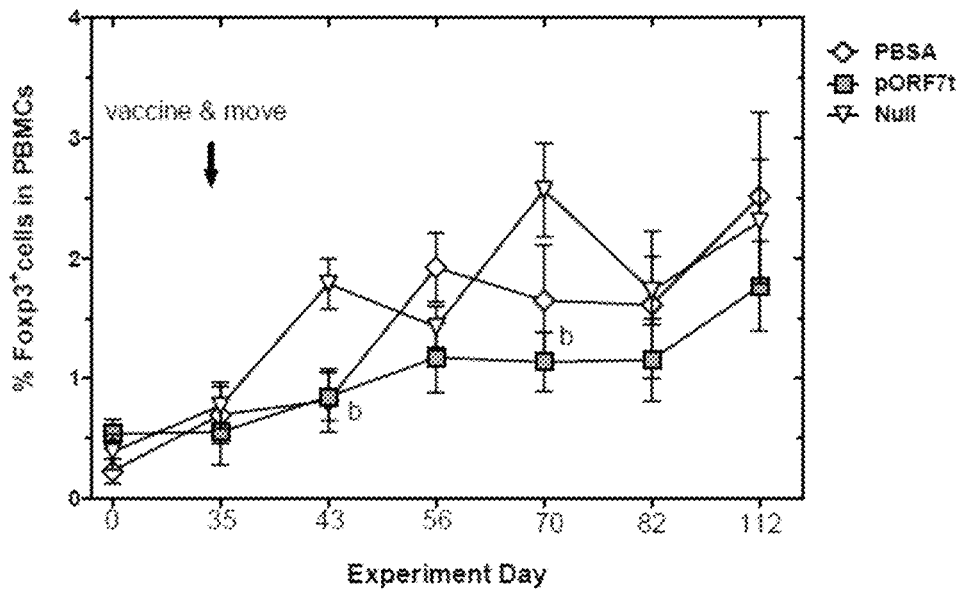
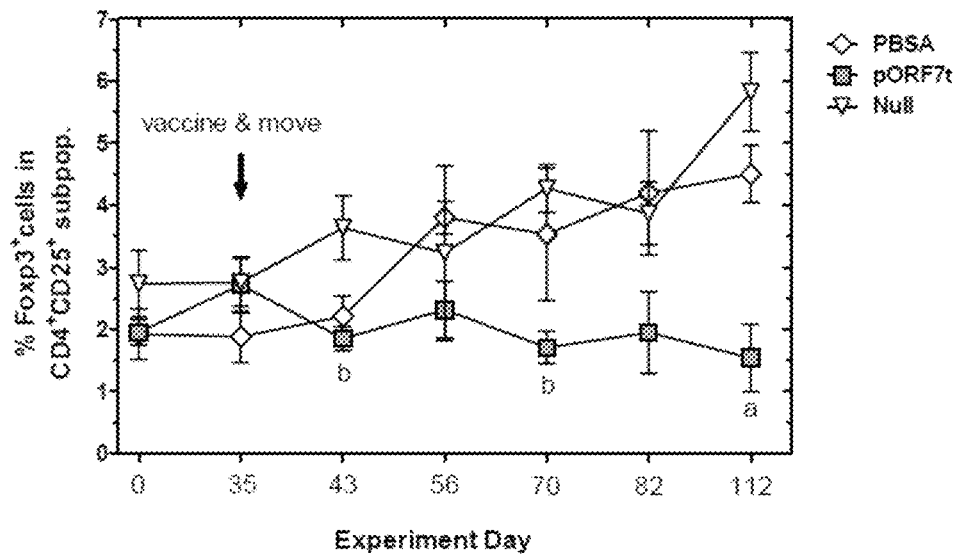

FIG. 21

Sequence Identification Number Descriptions

| Number | Type | Description |
|---|---|---|
| 1 | DNA | PRRSV ORF7 gene |
| 2 | PRT | Translation of PRRSV ORF7 gene |
| 3 | DNA | PRRSV genetically modified truncated ORF7 gene (ORF7t) |
| 4 | PRT | Translation of PRRSV genetically modified truncated ORF7 gene (ORF7t) |
| 5 | DNA | ORF7 US-F primer |
| 6 | DNA | ORF7 US-R primer |
| 7 | DNA | US-11R primer |
| 8 | DNA | pMASIA plasmid |
| 9 | DNA | pORF7 plasmid |
| 10 | DNA | pORF7t plasmid |
| 11 | DNA | pMASIA F primer |
| 12 | DNA | pBAD-ORF7 plasmid |
| 13 | DNA | 01NP1-PRRSV - Genbank accession number Q056373 |
| 14 | PRT | US pMA C2 |
| 15 | PRT | pBAD |
| 16 | PRT | 01NP1.2 |
| 17 | PRT | 01NP1 |
| 18 | DNA | pQE31 |

NEEDLE-FREE ADMINISTRATION OF PRRSV VACCINES

INCORPORATION BY REFERENCE

This application claims priority to provisional application U.S. Ser. No. 61/491,955, filed on Jun. 1, 2011, and incorporated by reference herein in its entirety.

FIELD OF THE INVENTION

The invention provides a method of vaccination of an animal against Porcine Reproductive and Respiratory Syndrome (PRRS).

BACKGROUND OF THE INVENTION

Porcine reproductive and respiratory syndrome virus (PRRSV) belongs to a family of enveloped positive-strand RNA viruses called arteri viruses. Other viruses in this family are the prototype virus, equine arteritis virus (EAV), lactate dehydrogenase-elevating virus (LDV) and simian hemorrhagic fever virus (SHFV) (de Vries et al., 1997 for review). Striking features common to the Coronaviridae and Arteriviridae have recently resulted in their placement in a newly created order, Nidovirales (Pringle, 1996; Cavanagh, 1997; de Vries et al., 1997). The four members of the Arterivirus group, while being similar in genome organization, replication strategy and amino acid sequence of the proteins are also similar in their preference for infection of macrophages, both in vivo and in vitro (Conzelmann et al., 1993; Meulenberg et al, 1993a).

The genome organization of arteriviruses is reviewed in de Vries et al. (1997). The genome RNA is single-stranded, infectious, polyadenylated and 5' capped. The genome of PRRSV is small, at 15,088 bases. Both the EAV and LDV genomes are slightly smaller at 12,700 bases and 14,200 bases, respectively. Complete sequences of EAV, LDV and PRRSV genomes are available (Den Boon et al, 1991; Godeny et al, 1993; Meulenberg et al. 1993a).

The genome contains eight open reading frames (ORFs) that encode, in the following order, the replicase genes (ORFs 1a and 1b), the envelope proteins (ORFs 2 to 6) and the nucleocapsid protein (ORF 7) (Meulenberg et al. 1993a). ORFs 2 to 7 are expressed from six sub-genomic RNAs, which are synthesized during replication (Meng et al., 1994, 1996). These sub-genomic RNAs form a 3' co-terminal nested set and are composed of a common leader, derived from the 5' end of the viral genome (Meulenberg et al. 1993b). Although the RNAs are structurally polycistronic, translation is restricted to the unique 5' sequences not present in the next smaller RNA of the set. Two large overlapping open reading frames (ORFs), designated ORF 1a and ORF 1b, take up more than two thirds of the genome. The second ORF, ORF 1b is only expressed after a translational read-through via a −1 frame shift mediated by a pseudoknot structure (Brierley 1995). The polypeptides encoded by these ORFs are proteolytically cleaved by virus-encoded proteases to yield the proteins involved in RNA synthesis.

ORF 2 encodes a 29-30 kDa N-glycosylated structural protein (GP2 or GS) showing the features of a class 1 integral membrane glycoproteins (Meulenberg and Petersen-den Besten, 1996 using the Ter Huurne strain of Lelystad virus). The ORF 2 protein shows 63% amino acid homology when the American VR-2332 isolate is compared to Lelystad virus (Murtaugh et al., 1995). ORF 3 encodes a N-glycosylated 45-50 kDa minor structural protein designated GP3 (van Nieuwstadt et al., 1996). ORF 4 encodes a 31-35 kDA minor N-glycosylated membrane protein designated GP4 (van Nieuwstadt et al., 1996). ORF 5 encodes GP5 or GL, which is a 25 kDA major envelope glycoprotein (Meulenberg et al., 1995). ORF 6 encodes an 18 kDA class III non-glycosylated integral membrane (M) protein (Meulenberg et al, 1995). ORF 7 encodes a 15 kDa non-glycosylated basic protein. Equine arteritis virus (EAV) genome ORF was designated 2a and codes for an essential 8 kDa structural protein called "E" (Snijder et al, 1999). In PRRSV, the homologous ORF has been designated 2b, the ORF 2 coding for GP2 (see above) being renamed ORF 2a (Snijder et al., 1999).

Two main groups of clinical signs are associated with the occurrence of PRRS although it is now recognized that clinical effects vary greatly among infected herds and in many cases, infection is sub-clinical and productivity is within acceptable parameters. The two groups are: (1) Reproductive signs which include premature births, late-term abortions, piglets born weak and increased numbers of still-births and mummifications (Done and Paton, 1995). (2) Signs of respiratory disease are also important in neonatal pigs with labored breathing and coughing being the most dominant characteristics. The symptoms usually occur in pigs about three weeks of age though all ages are susceptible. In contrast to the reproductive failures, clinically overt respiratory disease is harder to reproduce experimentally (Zimmermann et al. 1997). These clinical signs vary considerably and may be influenced by the virus strain (Halbur et al., 1995), age at infection and differences in genetic susceptibility (Halbur et al., 1992), concurrent infections (Galina et al., 1994), pig density, pig movements and housing systems (Done et al., 1996) and immune status including the presence of low levels of PRRS virus-specific antibodies which may be enhancing (Yoon et al., 1994).

There appear to be three routes of transmission: (1) nose to nose or close contact (Done et al, 1996), (2) aerosols (Le Potier et al, 1995), and (3) spread through urine, feces and semen. Transmission via insemination with contaminated semen is well-documented (Yeager et al., 1993; Albina, 1997). In terms of pathogenesis, the most significant change induced by PRRSV is the severe damage to alveolar macrophages, which are destroyed in huge numbers (reviewed in Done and Paton, 1995; Rossow, 1998). The induction of apoptosis in a large number of mononuclear cells in the lungs and lymph nodes might be an explanation for a dramatic reduction in the number of alveolar macrophages and circulating lymphocytes and monocytes in PRRSV-infected pigs (Sirinarumitr et al., 1998; Sur et al., 1998). Coupled with the destruction of circulating lymphocytes and the destruction of the mucociliary clearance system, this may suppress immunity and render pigs more susceptible to secondary infection. An enhanced rate of bacterial secondary infections has been documented following PRRSV infection (Galina et al, 1994; Done and Paton, 1995; Nakamine et al. 1998). The severity of PRRSV infection may be also increased by bacterial or mycoplasma infection (Thacker et al. 1999). In addition a number of viral infections have been found associated with PRRS (Carlson, 1992; Brun et al., 1992; Halbur et al, 1993; Done et al., 1996; Heinen et al., 1998).

Infection with PRRSV usually induces slow and weak anti-viral immune responses, leading to persistent infection and immunosuppression in the lungs of infected pigs. The reported PRRSV immune evasion strategies include inhibition of innate immune responses, induction systemic immunosuppressive cytokine; IL-10 and porcine Tregs (CD4$^+$ CD25$^+$Foxp3$^+$ lymphocytes) that resulted in generalized immunosuppression during an early phase of infection. The adaptive immunity against PRRSV is often slow and inefficient, with evidence of polyclonal B cell activation and induction of ADE in the following exposure. Applicants have recently generated experimental evidence suggesting that the immunomodulatory properties of the virus may rely on the interaction of the structural protein and the immune cells (S. Suradhat, unpublished observation). In general, PRRSV infection does not kill the infected pigs, but rather causes several health complications related to suboptimal immune function. Several reports demonstrate that the PRRSV-induced immunomodulatory activities could result in secondary immunodeficiency causing persistent infection, secondary complications, and vaccine failure in the infected pigs.

Although, several commercial vaccines are available in the market, the benefit of vaccine-induced immunity in the vaccinated pigs has not been satisfactory. The modified live vaccine (MLV) has proven more efficacious than the inactivated vaccine due to its ability to induce relatively broader immunity. Evidence also suggest a role for cell-mediated immunity in limiting PRRSV infection and spreading within infected pigs. However, induction of specific immunity by MLV has proven to be delayed and inefficient. In addition, the immunity induced by MLV provides only partial protection against heterologous PRRSV infection. In some cases, the use of MLV has raised concerns regarding safety and induction of immunotolerance.

In general, the development of vaccine against viral infection relies on induction of viral-specific protective humoral and cellular-mediated immunity. The development of effective PRRS vaccine has been extensively challenged with the high antigenic variability of the virus (quasispecies) and its ability to control the immune system via several immunomodulatory activities. Therefore, despite of being properly primed prior to infection, the vaccine-induced, PRRSV-specific effector/memory cells might not be able to function well during an early phase of infection. Since PRRSV alone does not kill infected pigs, we hypothesize that if the PRRSV-induced immunomodulatory effects is removed/reduced, the immune system of the infected host should be able to limit/clear viral infection by itself. This will also help minimizing persistent infection and secondary complications in the late stage of infection.

A vaccine that could induce strong cross-reactive, anti-PRRSV cellular immunity should have benefit on reduction of viremia, PRRSV-induced clinical signs, and improving of the general health condition by reducing secondary complications related to PRRSV-induced immunodeficiency. In addition, avoiding of unnecessary B cell activation by the vaccine antigen would be ideal for implementation of the differentiation of infected and vaccinated animals (DIVA) strategies in the farms. It has been proposed to use needle-free injectors in veterinary field (WO-A-98/03659; WO-A-92/15330; WO-A-98/03658; van Rooij et al., Vet. Immunol. Immunopathol., 1998, 66(2), 113-126; U.S. Pat. No. 6,451, 770; Schrijver et al., Vaccine, 1998, 16(2-3), 130-134), but the prior art contains inconsistent and contradictory results (McKercher P. D. et al., Can. J. Comp. Med., 1976, 40, 67-74; Epstein, Hum. Gene Ther., 2002, 13(13), 275-280; Haensler, Vaccine, 1999, 17(7-8), 628-638). Therefore, a skilled person cannot predict whether needle-free delivery will be efficacious for an untested host/vaccine combination.

Citation or identification of any document in this application is not an admission that such document is available as prior art to the present invention.

SUMMARY OF THE INVENTION

The objective of the present invention is to provide a new method of vaccination of an animal of the suidae family, which is efficient, easier and less expensive to use, and which leads to increased safety.

This objective is met by administering a porcine reproductive and respiratory syndrome virus (PRRSV) DNA vaccine with the aid of a liquid jet needle-free injector, ensuring distribution of the vaccine essentially in the dermis and the hypodermis of the animal.

A first object of the present invention is a vaccination method against PRRSV, which may comprise the step of administration essentially in the dermis and the hypodermis of an animal of the suidae family an efficient amount of a PRRSV DNA vaccine using a liquid jet needle-free injector, which administration elicits a safe and protective immune response against PRRSV.

Another object is a vaccination kit or set, which may comprise such a liquid jet needle-free injector and at least one vaccine vial containing a PRRSV DNA vaccine, operatively assembled to perform the administration of the vaccine essentially in the dermis and the hypodermis of an animal of the suidae family and to elicit a safe and protective immune response against PRRSV.

Another object of the invention is the use of a DNA vector which may encode and express at least one PRRSV immunogen and of an acceptable vehicle or diluent, for the preparation of a liquid vaccine designed to be administered essentially in the dermis and the hypodermis of animals of the suidae family using a liquid jet needle-free injector, and resulting in eliciting a safe and protective immune response against PRRSV.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

These and other embodiments are disclosed or are obvious from and encompassed by, the following Detailed Description.

BRIEF DESCRIPTION OF DRAWINGS

The following Detailed Description, given by way of example, and not intended to limit the invention to specific embodiments described, may be understood in conjunction with the accompanying Figures, incorporated herein by reference, in which:

FIG. 1 illustrates the cloning scheme for producing pORF7 (SEQ ID NO:10) and pORF7t (SEQ ID NO:11); included is a map of pBAD-ORF7 (SEQ ID NO:13) and pMASIA (SEQ ID NO:9);

FIG. 2 presents amino acid sequence alignments of nucleocapsid proteins 1) US pMA C2 (SEQ ID NO:15), pBAD (SEQ ID NO:16), 01NP1.2 (SEQ ID NO:17); and 2) 01NP1 (SEQ ID NO:18) and ORF7t (SEQ ID NO:4);

FIG. 3 is an agarose gel image showing presence or absence of PRRSV-nucleocapsid gene (ORF7) PCR amplification products for the of the PRRSV-nucleocapsid gene (ORF7) in porcine PBMC transfected with either pORF7, pORF7t, or pMASIA plasmids;

FIG. 6 presents the PRRSV vaccination study plan, including timeline of events and data collection;

FIG. 7A is an image depicting the intradermal DNA immunization technique;

FIG. 7B is an image depicting the injected sites following intradermal injection;

FIG. 12A is a graph of the numbers of PRRSV-specific IL-10+ cells in the PBMC;

FIG. 12B is a graph of the numbers of PRRSV-specific IL-10+ cells in the lymphocyte population;

FIG. 12C is a graph of the number of PRRSV-specific IFNγ+ cells in the PBMC;

FIG. 12D is a graph of the number of PRRSV-specific IFNγ+ cells in the lymphocyte population; the FIG. 12 data represents mean percentage (±SEM) of the cytokine producing cells, obtained by the percentage of the cytokine producing cells from the PRRSV-cultured cells—the percentage of cytokine producing cells from the cells cultured with mock lysate. "a" indicates statistical difference from other groups, at $p<0.05$. "b" indicates statistical difference between the pORF7t and null plasmid, at $p<0.05$. "c" indicates statistical different between the pORF7t and PBSA, at $p<0.05$. "d" indicates statistical different between the null and PBSA, at $p<0.05$.

FIG. 13A is a graph of the numbers of PRRSV-specific Foxp3+ cells in the PBMC of the experimental pigs;

FIG. 13B is a graph of the numbers of PRRSV-specific Foxp3+ cells in the CD4+CD25+ lymphocyte subpopulation from the PBMC of the experimental pigs; the FIG. 13 data represents mean percentage (±SEM) of the Foxp3+ cells, obtained by the percentage of the Foxp3+ cells from the PRRSV-cultured cells—the percentage of Foxp3+ cells from the cells cultured with mock lysate. ("a" indicates statistical difference from other groups, at $p<0.05$. "b" indicates statistical difference between the pORF7t and null plasmid, at $p<0.05$.)

FIG. 14A is a graph of the numbers of PRRSV-specific IL-10+ cells in the PBMC;

FIG. 14B is a graph of the numbers of PRRSV-specific IL-10+ cells in the lymphocyte population (B);

FIG. 14C is a graph of the number of PRRSV-specific IFNγ+ cells in the PBMC;

FIG. 14D is a graph of the number of PRRSV-specific IFNγ+ cells in the lymphocyte population; pigs were vaccinated with pORF7t, null plasmid, or PBSA on d35, and moved to the finisher unit. The freshly isolated porcine PBMC samples were cultured with 0.1 m.o.i. of US-PRRSV (strain 01NP1), or mock-infected MARC-145 lysate for 48 hrs prior to fluorescent staining and flow cytometric analyses. The data represents mean percentage (±SEM) of the cytokine producing cells, obtained by the percentage of the cytokine producing cells from the PRRSV-cultured cells—the percentage of cytokine producing cells from the cells cultured with mock lysate. ("a" indicates statistical difference from other groups, at $p<0.05$. "b" indicates statistical difference between the pORF7t and null plasmid, at $p<0.05$. "c" indicates statistical different between the pORF7t and PBSA, at $p<0.05$. d indicates statistical different between the null and PBSA, at $p<0.05$);

FIG. 15A is a graph of the numbers of PRRSV-specific Foxp3+ cells in the PBMC of the experimental pigs;

FIG. 15B is a graph of the numbers of PRRSV-specific Foxp3+ cells in the CD4+CD25+ lymphocyte subpopulation from the PBMC of the experimental pigs; the data are mean percentage (±SEM) of the Foxp3+ cells, obtained by the percentage of the Foxp3+ cells from the PRRSV-cultured cells—the percentage of Foxp3+ cells from the cells cultured with mock lysate. (a indicates statistical difference from other groups, at $p<0.05$. b indicates statistical difference between the pORF7t and null plasmid, at $p<0.05$.)

FIG. 21 is a summary table of the sequence identification listing;

DETAILED DESCRIPTION

Figure 4:
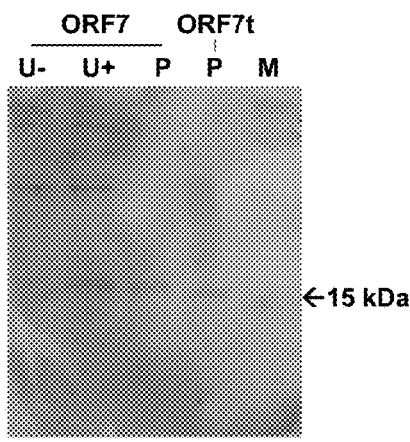
FIG. 4 presents a Western blot analysis of the recombinant proteins produced from the expression vector containing ORF7 or ORF7t gene fragment.

The present invention concerns a vaccination method against PRRSV, comprising the step of administration essentially in the dermis and the hypodermis of an animal of the suidae family an efficient amount of a PRRSV DNA vaccine using a liquid jet needle-free injector, which administration elicits a safe and protective immune response against PRRSV. "Essentially" means that some portion of the vaccine may also be found in the epidermis or in the muscles.

A protective immune response is characterized by a significant reduction of the antigenemia after challenge or by significant neutralizing antibody titers. A safe immune response is characterized by the limitation of the side effects linked to the vaccine administration, notably by a significant reduction or by the absence of local injection site reaction and by a significant reduction or by the absence of symptoms, like anorexia and depression following vaccine administration.

As used herein, the term "pig" refers to an animal of porcine origin, in other words, an animal of the suidae family. The term "boar" refers to an entire male pig over six months of age destined as a sire. The term "gilt" refers to a young female pig who has not produced first litter up to first farrowing. The term "hog" refers to a castrated male pig. The term "piglet" refers to a young pig. The term "porker" refers to a breed of pig breed for good pork meat cuts. The term "stores" refers to a pig which may be about 10-12 weeks old. The term "sow" refers to a female of reproductive age and capability or a female pig after she has had her first litter. The term "weaned piglet" or "weaner" refers to a young pig which may be about 11 to about 24 days of age, about two to three weeks of age, about three to five weeks of age or about five to eight weeks old weeks of age.

As used herein, the term "virulent" means an isolate that retains its ability to be infectious in an animal host.

As used herein, the term "inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with thimerosal or formalin), sonication, radiation, heat or any other convention means sufficient to prevent replication or growth of the organism while maintaining its immunogenicity.

As used herein, the term "immune response" refers to a response elicited in an animal. An immune response may refer to cellular immunity (CMI); humoral immunity or may involve both. The present invention also contemplates a response limited to a part of the immune system. For example, a vaccine composition of the present invention may specifically induce an increased gamma interferon response.

As used herein, the term "antigen" or "immunogen" means a substance that induces a specific immune response in a host animal. The antigen may comprise a whole organism, killed, attenuated or live; a subunit or portion of an organism; a recombinant vector containing a polynucleotide encoding an immunogen, capable of inducing an immune response upon presentation to a host animal; a protein, a polypeptide, a peptide, an epitope, a hapten, or any combination thereof.

As used herein, the term "multivalent" means a vaccine containing more than one antigen from different genera or species of microorganisms (for example, a vaccine comprising antigens from *Pasteurella multocida, Salmonella, Escherichia coli, Haemophilus somnus* and *Clostridium*).

As used herein, the term "adjuvant" means a substance added to a vaccine to increase a vaccine's immunogenicity. The mechanism of how an adjuvant operates is not entirely known. Some adjuvants are believed to enhance the immune response by slowly releasing the antigen, while other adjuvants present the immunogen to the host immune system more efficiently or effectively or stimulate the production of specific cytokines.

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous e.g. intradermal, intramuscular, subcutaneous. Vaccine compositions can be administered alone, or can be co-administered or sequentially administered with other treatments or therapies. The compositions can contain auxiliary substances such as wetting or emulsifying agents, pH buffering agents, adjuvants, or viscosity enhancing additives, preservatives, colors, and the like, depending upon the route of administration and the preparation desired. Standard pharmaceutical texts, such as "Remington's Pharmaceutical Sciences," 1990 may be consulted to prepare suitable preparations, without undue experimentation.

The invention further encompasses at least one PRRSV immunogen contained in a vector molecule or an expression vector and operably linked to a promoter element and optionally to an enhancer. In an embodiment the vector is pMASIA.

In an embodiment, the promoter is the promoter of the cytomegalovirus (CMV) immediate early gene. In another advantageous embodiment, the promoter and/or enhancer elements are oxygen-inducible. Examples of oxygen-inducible promoters and/or enhancers that can be used in the methods of the present invention include, but are not limited to, early growth response-1 (Egr1) promoter (see, e.g., Park et al., J Clin Invest. 2002 August; 110(3):403-1), hypoxia-inducible factor (HIF) inducible enhancers (see e.g., Cuevas et al., Cancer Res. 2003 Oct. 15; 63(20):6877-84) and Mn-superoxide dismutase (Mn-SOD) promoters (see, e.g., Gao et al., Gene. 1996 Oct. 17; 176(1-2):269-70).

In another embodiment, the enhancers and/or promoters include various cell or tissue specific promoters (e.g., muscle, endothelial cell, liver, somatic cell or stem cell), various viral promoters and enhancers and various PRRSV immunogen sequences isogenically specific for each animal species. Examples of muscle-specific promoters and enhancers have been described are known to one of skill in the art (see, e.g., Li et al., Gene Ther. 1999 December; 6(12):2005-11; Li et al., Nat Biotechnol. 1999 March; 17(3):241-5 and Loirat et al., Virology. 1999 Jul. 20; 260(1):74-83; the disclosures of which are incorporated by reference in their entireties).

Promoters and enhancers that may be employed in the present invention include, but are not limited to LTR or the Rous sarcoma virus, TK of HSV-1, early or late promoter of SV40, adenovirus major late (MLP), phosphoglycerate kinase, metallothionein, $\alpha$-1 antitrypsin, albumin, collagenase, elastase I, $\beta$-actin, $\beta$-globin, $\gamma$-globin, $\alpha$-fetoprotein, muscle creatine kinase.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors also included are viral vectors.

The term "recombinant" means a polynucleotide of semi-synthetic or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

The present invention encompasses a vector expressing a PRRSV immunogen or variants or analogues or fragments. Elements for the expression of a PRRSV immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. a PRRSV immunogen, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

Methods for making and/or administering a vector or recombinants or plasmid for expression of gene products of genes either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745, 051; 4,769,331; 4,945,050; 5,494,807; 5,514,375; 5,744, 140; 5,744,141; 5,756,103; 5,762,938; 5,766,599; 5,990, 091; 5,174,993; 5,505,941; 5,338,683; 5,494,807; 5,591, 639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6,312,683; U.S. patent application Ser. No. 920,197, filed Oct. 16, 1986; WO 90/01543; WO91/11525; WO 94/16716; WO 96/39491; WO 98/33510; EP 265785; EP 0 370 573; Andreansky et al., Proc. Natl. Acad. Sci. USA 1996; 93:11313-11318; Ballay et al., EMBO J. 1993; 4:3861-65; Felgner et al., J. Biol. Chem. 1994; 269:2550-2561; Frolov et al., Proc. Natl. Acad. Sci. USA 1996; 93:11371-11377; Graham, Tibtech 1990; 8:85-87; Grunhaus et al., Sem. Virol. 1992; 3:237-52; Ju et al., Diabetologia 1998; 41:736-739; Kitson et al., J. Virol. 1991; 65:3068-3075; McClements et al., Proc. Natl. Acad. Sci. USA 1996; 93:11414-11420; Moss, Proc. Natl. Acad. Sci. USA 1996; 93:11341-11348; Paoletti, Proc. Natl. Acad. Sci. USA 1996; 93:11349-11353; Pennock et al., Mol. Cell. Biol. 1984; 4:399-406; Richardson (Ed), Methods in Molecular Biology 1995; 39, "Baculovirus Expression Protocols," Humana Press Inc.; Smith et al. (1983) Mol. Cell. Biol. 1983; 3:2156-2165; Robertson et al., Proc. Natl. Acad. Sci. USA 1996; 93:11334-11340; Robinson et al., Sem. Immunol. 1997; 9:271; and Roizman, Proc. Natl. Acad. Sci. USA 1996; 93:11307-11312. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., human adenovirus, canine adenovirus), herpesvirus (e.g. canine herpesvirus), baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-PRRSV immunogens, e.g., non-PRRSV immunogens, non-PRRSV immunogens peptides or fragments thereof, cytokines, etc. to be expressed by vector or vectors in, or included in, the compositions of the invention.

The present invention also relates to preparations comprising vectors, such as expression vectors, e.g., therapeutic compositions. The preparations can comprise, consist essentially of, or consist of one or more vectors, e.g., expression vectors, such as in vivo expression vectors, comprising, consisting essentially or consisting of (and advantageously expressing) one or more of PRRSV immunogens. Advantageously, the vector contains and expresses a polynucleotide that includes, consists essentially of, or consists of a coding region encoding one or more PRRSV immunogens a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of a PRRSV immunogen or a fragment thereof.

According to another embodiment, the vector or vectors in the preparation comprise, or consist essentially of, or consist of polynucleotide(s) encoding one or more proteins or fragment(s) thereof of a PRRSV immunogen, the vector or vectors have expression of the polynucleotide(s). The inventive preparation advantageously comprises, consists essentially of, or consists of, at least two vectors comprising, consisting essentially of, or consisting of, and advantageously also expressing, advantageously in vivo under appropriate conditions or suitable conditions or in a suitable host cell, polynucleotides from different PRRSV isolates encoding the same proteins and/or for different proteins, but advantageously for the same proteins. Preparations containing one or more vectors containing, consisting essentially of or consisting of polynucleotides encoding, and advantageously expressing, advantageously in vivo, PRRSV peptide, fusion protein or an epitope thereof.

According to one embodiment of the invention, the expression vector is a DNA vector, in particular an in vivo expression vector.

In one particular embodiment the viral vector is a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807), swinepox, raccoonpox, camelpox, or myxomatosis virus.

According to another embodiment of the invention, the poxvirus vector is a canarypox virus or a fowlpox virus vector, advantageously an attenuated canarypox virus or fowlpox virus. In this regard, is made to the canarypox available from the ATCC under access number VR-111. Attenuated canarypox viruses are described in U.S. Pat. No. 5,756,103 (ALVAC) and WO01/05934. Numerous fowlpox virus vaccination strains are also available, e.g. the DIFTOSEC CT strain marketed by MERIAL and the NOBILIS VARIOLE vaccine marketed by INTERVET; and, reference is also made to U.S. Pat. No. 5,766,599 which pertains to the attenuated fowlpox strain TROVAC.

For information on the method to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and U.S. Pat. No. 5,766,599 inter alia; as to canarypox mention is made of U.S. Pat. No. 5,756,103 inter alia; as to swinepox mention is made of U.S. Pat. No. 5,382,425 inter alia; and, as to raccoonpox, mention is made of WO00/03030 inter alia.

When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters.

Advantageously, the polynucleotide to be expressed is inserted under the control of a specific poxvirus promoter, e.g., the vaccinia promoter 7.5 kDa (Cochran et al., J. Virology, 1985, 54, 30-35), the vaccinia promoter I3L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

In an embodiment the viral vector is an adenovirus, such as a human adenovirus (HAV) or a canine adenovirus (CAV).

In one embodiment the viral vector is a human adenovirus, in particular a serotype 5 adenovirus, rendered incompetent for replication by a deletion in the E1 region of the viral genome, in particular from about nucleotide 459 to about nucleotide 3510 by reference to the sequence of the hAd5 disclosed in Genbank under the accession number M73260 and in the referenced publication J. Chroboczek et al Virol. 1992, 186, 280-285. The deleted adenovirus is propagated in E1-expressing 293 (F. Graham et al J. Gen. Virol. 1977, 36, 59-72) or PER cells, in particular PER.C6 (F. Falloux et al Human Gene Therapy 1998, 9, 1909-1917). The human adenovirus can be deleted in the E3 region, in particular from about nucleotide 28592 to about nucleotide 30470. The deletion in the E1 region can be done in combination with a deletion in the E3 region (see, e.g. J. Shriver et al. Nature, 2002, 415, 331-335, F. Graham et al Methods in Molecular Biology Vol. 7: Gene Transfer and Expression Protocols Edited by E. Murray, The Human Press Inc, 1991, p 109-128; Y. Ilan et al Proc. Natl. Acad. Sci. 1997, 94, 2587-2592; U.S. Pat. No. 6,133,028; U.S. Pat. No. 6,692,956; S. Tripathy et al Proc. Natl. Acad. Sci. 1994, 91, 11557-11561; B. Tapnell Adv. Drug Deliv. Rev. 1993, 12, 185-199; X. Danthinne et al Gene Therapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci (region) eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, preferably a cytomegalovirus immediate-early gene promoter (CMV-IE promoter), in particular the enhancer/promoter region from about nucleotide −734 to about nucleotide +7 in M. Boshart et al Cell 1985, 41, 521-530 or the enhancer/promoter region from the pCI vector from Promega Corp. The CMV-IE promoter is advantageously of murine or human origin. The promoter of the elongation factor 1α can also be used. In one particular embodiment a promoter regulated by hypoxia, e.g. the promoter HRE described in K. Boast et al Human Gene Therapy 1999, 13, 2197-2208), can be used. A muscle specific promoter can also be used (X. Li et al Nat. Biotechnol. 1999, 17, 241-245). Strong promoters are also discussed herein in relation to plasmid vectors. In one embodiment, a splicing sequence can be located downstream of the enhancer/promoter region. For example, the intron 1 isolated from the CMV-IE gene (R. Stenberg et al J. Virol. 1984, 49, 190), the intron isolated from the rabbit or human β-globin gene, in particular the intron 2 from the b-globin gene, the intron isolated from the immunoglobulin gene, a splicing sequence from the SV40 early gene or the chimeric intron sequence isolated from the pCI vector from Promega Corp. comprising the human β-globin donor sequence fused to the mouse immunoglobulin acceptor sequence (from about nucleotide 890 to about nucleotide 1022 in Genbank under the accession number CVU47120). A poly(A) sequence and terminator sequence can be inserted downstream the polynucleotide to be expressed, e.g. a bovine growth hormone gene, in particular from about nucleotide 2339 to about nucleotide 2550 in Genbank under the accession number BOVGHRH, a rabbit β-globin gene or a SV40 late gene polyadenylation signal.

In another embodiment the viral vector is a canine adenovirus, in particular a CAV-2 (see, e.g. L. Fischer et al. Vaccine, 2002, 20, 3485-3497; U.S. Pat. No. 5,529,780; U.S. Pat. No. 5,688,920; PCT Application No. WO95/14102). For CAV, the insertion sites can be in the E3 region and/or in the region located between the E4 region and the right ITR region (see U.S. Pat. No. 6,090,393; U.S. Pat. No. 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another particular embodiment the viral vector is a herpesvirus such as a canine herpesvirus (CHV) or a porcine herpesvirus (FHV). For CHV, the insertion sites may be in particular in the thymidine kinase gene, in the ORF3, or in the UL43 ORF (see U.S. Pat. No. 6,159,477). In one embodiment the polynucleotide to be expressed is inserted under the control of a promoter functional in eukaryotic cells, advantageously a CMV-IE promoter (murine or human). In one particular embodiment a promoter regulated by hypoxia, e.g. the promoter HRE described in K. Boast et al Human Gene Therapy 1999, 13, 2197-2208), can be used. A poly(A) sequence and terminator sequence can be inserted downstream the polynucleotide to be expressed, e.g. bovine growth hormone or a rabbit β-globin gene polyadenylation signal.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke C. et al., Journal of Infectious Diseases, 1997, 175, 91-97; Hartikka J. et al., Human Gene Therapy, 1996, 7, 1205-1217, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705;

6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding the PRRSV immunogen or a variant, analog or fragment thereof, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart M. et al., Cell., 1985, 41, 521-530) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Preferably, the plasmids comprise or consist essentially of other expression control elements. It is particularly advantageous to incorporate stabilizing sequence(s), e.g., intron sequence(s), preferably the first intron of the hCMV-IE (PCT Application N° WO89/01036), the intron II of the rabbit b-globin gene (van Ooyen et al., Science, 1979, 206, 337-344).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit b-globin gene or the poly(A) signal of the SV40 virus.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

Host cells that can be used in the present invention include, but are not limited to, muscle cells, keratinocytes, myoblasts, Chinese Hamster ovary cells (CHO), vero cells, BHK21, sf9 cells, and the like. It is understood to one of skill in the art that conditions for culturing a host cell varies according to the particular gene and that routine experimentation is necessary at times to determine the optimal conditions for culturing an PRRSV depending on the host cell. For example, the vector encoding an PRRSV immunogen can be transformed into myoblasts (which can be obtained from muscle tissue from the animal in need of treatment), and the transformed myoblasts can be transplanted to the animal. In another example, keratinocytes can also be transformed with a vector encoding a PRRSV immunogen and transplanted into the animal, resulting in secretion of a PRRSV immunogen into circulation.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In an advantageous embodiment, the invention provides for the administration of a therapeutically effective amount of a formulation for the delivery and expression of a PRRSV immunogen in a target cell. Determination of the therapeutically effective amount is routine experimentation for one of ordinary skill in the art. In one embodiment, the formulation comprises an expression vector comprising a polynucleotide that expresses a PRRSV immunogen and a pharmaceutically or veterinarily acceptable carrier, vehicle or excipient. In an advantageous embodiment, the pharmaceutically or veterinarily acceptable carrier, vehicle or excipient facilitates transfection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9%

NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

$$R_1-O-CH_2-CH(OR_1)-CH_2-N^+(CH_3)(CH_3)-R_2-X$$

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and advantageously about 1:about 1 and about 1:about 2, e.g., 1:1 and 1:2.

The polymers of acrylic or methacrylic acid are preferably crosslinked, in particular with polyalkenyl ethers of sugars or polyalcohols. These compounds are known under the term carbomer (Pharmeuropa vol. 8, No. 2, June 1996). Persons skilled in the art can also refer to U.S. Pat. No. 2,909,462 describing such acrylic polymers crosslinked with a polyhydroxylated compound having at least 3 hydroxyl groups, preferably not more than 8, the hydrogen atoms of at least three hydroxyls being replaced with unsaturated aliphatic radicals having at least 2 carbon atoms. The preferred radicals are those containing 2 to 4 carbon atoms, e.g. vinyls, allyls and other ethylenically unsaturated groups. The unsaturated radicals may themselves contain other substituents, such as methyl. The products sold under the name Carbopol® (BF Goodrich, Ohio, USA) are particularly appropriate. They are crosslinked with an allyl sucrose or with allylpentaerythritol. Among them, there may be mentioned CARBOPOL® 974P, 934P and 971P.

Among the copolymers of maleic anhydride and of alkenyl derivative, the EMA® copolymers (Monsanto) which are copolymers of maleic anhydride and of ethylene, which are linear or crosslinked, for example crosslinked with divinyl ether, are preferred. Reference may be made to J. Fields et al., Nature, 186: 778-780, Jun. 4, 1960.

The proportions of adjuvant which are useful are well known and readily available to the one skilled in the art. By way of example, the concentration of polymers of acrylic or methacrylic acid or of anhydride maleic and alkenyl copolymers in the final vaccine composition will be from 0.01% to 1.5% W/V, more particularly from 0.05 to 1% W/V, preferably from 0.1 to 0.4% W/V.

Optionally the vaccine used according to the method of the invention may contain a cytokine. The cytokine may be present as a protein or as a gene encoding this cytokine inserted into a recombinant viral vector. The cytokines may be selected among the porcine cytokines, e.g. porcine interleukin 18 (fIL-18) (Taylor S. et al., DNA Seq., 2000, 10(6), 387-394), fIL-16 (Leutenegger C. M. et al., DNA Seq., 1998, 9(1), 59-63), fIL-12 (Fehr D. et al., DNA Seq., 1997, 8(1-2), 77-82; Imamura T. et al., J. Vet. Med. Sci., 2000, 62(10), 1079-1087) and porcine GM-C SF (Granulocyte-Macrophage Colony-Stimulating Factor) (GenBank AF053007).

In a specific embodiment, the pharmaceutical composition is directly administered in vivo, and the encoded product is expressed by the vector in the host. The methods of in vivo delivery a vector encoding a PRRSV immunogen can be modified to deliver the PRRSV immunogen of the present invention to a porcine. The in vivo delivery of a vector encoding the PRRSV immunogen described herein can be accomplished by one of ordinary skill in the art given the teachings of the above-mentioned references.

Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

In the case of therapeutic and/or pharmaceutical compositions based on a plasmid vector, a dose can comprise, consist essentially of or consist of, in general terms, about in 1 mg to about 2000 mg, advantageously about 50 mg to about 1000 mg and more advantageously from about 100 μg to about 800 μg of plasmid expressing a PRRSV immunogen. When the therapeutic and/or pharmaceutical compositions based on a plasmid vector is administered with electroporation the dose of plasmid is generally between about 0.1 μg and 1 mg, advantageously between about 1 μg and 100 μg, advantageously between about 2 μg and 50 μg. The dose volumes can be between about 0.1 and about 2 ml, advantageously between about 0.2 and about 1 ml. These doses and dose volumes are suitable for the treatment of felines and other mammalian target species such as equines and canines.

The therapeutic and/or pharmaceutical composition contains per dose from about $10^4$ to about $10^{11}$, advantageously from about $10^5$ to about $10^{10}$ and more advantageously from about $10^6$ to about $10^9$ viral particles of recombinant adenovirus expressing a PRRSV immunogen. In the case of therapeutic and/or pharmaceutical compositions based on a poxvirus, a dose can be between about $10^2$ pfu and about $10^9$ pfu. The pharmaceutical composition contains per dose from about $10^5$ to $10^9$, advantageously from about $10^6$ to $10^8$ pfu of poxvirus or herpesvirus recombinant expressing a PRRSV immunogen.

The dose volume of compositions for target species that are mammals, e.g., the dose volume of porcine compositions, based on viral vectors, e.g., non-poxvirus-viral-vector-based compositions, is generally between about 0.1 to about 2.0 ml, preferably between about 0.1 to about 1.0 ml, and more preferably between about 0.5 ml to about 1.0 ml.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Biojector or Vitajet apparatus (Bioject, Oregon, USA)). Another approach to administer plasmid compositions is to use electroporation (see, e.g. S. Tollefsen et al. Vaccine, 2002, 20, 3370-3378; S. Tollefsen et al. Scand. J. Immunol., 2003, 57, 229-238; S. Babiuk et al., Vaccine, 2002, 20, 3399-3408; PCT Application No. WO99/01158). In another embodiment, the plasmid is delivered to the animal by gene gun or gold particle bombardment. In an advantageous embodiment, the animal is a vertebrate. In a more advantageous embodiment, the vertebrate is a cat.

Liquid jet needle-free injectors are devices performing injections of a certain amount of liquid under high pressure through a minute orifice. Mechanical specifications of the injector may be adjusted or selected in order to control the depth of penetration into tissues. Administrations of a liquid using a syringe or a needle-free injector end up in a different distribution of the liquid in the tissues. Using a syringe end up in a localized bolus or pool. Using an injector end up in a diffused distribution in the layers of the targeted tissues, as illustrated in WO-A-01/13975.

The depth of penetration is mainly controlled by the liquid pressure. This liquid pressure is depending upon the mechanical specifications of the injector, such as the strength of spring or any other propulsion means and the diameter of the piston and the nozzle orifice. This is readily available to the one skilled in the art.

The depth of injection may be easily determined by the dissection of the tissue at the injection site (corresponding preferably to the location where the vaccine is going to be administered, and the test is advantageously performed on an animal of the same species and age than the population to be vaccinated) after the administration of a colored liquid having preferably the same viscosity than the intended vaccine. This test may be performed directly with the intended vaccine containing further a dye. This test allows the one skilled in the art to adjust the mechanical specifications of an injector.

The needle-free injector may be equipped with a head comprising one or several nozzles. The use of several nozzles allows to increase the dispersion pattern of the vaccine over a larger area. There can be from 1 to 10 nozzles, preferably from 1 to 6.

Several injectors are available in the commerce. The Vitajet™3 (Bioject Inc.) is particularly adapted to the method according to the invention.

It is advantageous to use an injector equipped with means allowing to fit to the injector directly a standard vial or ampoule. In addition, the vaccine vial may comprise several vaccine doses allowing several shots of vaccine and/or vaccination of several animals using the injector and the same vial. Thus, the injector is preferably able to perform successive injections from a same vial.

The invention also relates to a method to stimulate the immune response of a vertebrate. In one embodiment, the vertebrate is a bird, cat, cow, dog, fish, goat, horse, human, mouse, monkey, pig, rat or sheep. In a more advantageous embodiment, the vertebrate is a cat.

In one aspect of the invention, vaccination against PRRSV can be associated with a vaccination against another porcine disease. The vaccine comprises the DNA vector according to the invention and a vaccine component able to protect against other porcine pathogens including, but not solely, *Mycoplasma hyopneumoniae* and PCV2.

The volume of dose injected may be from about 0.1 ml to about 1.0 ml, preferably about 0.1 ml to about 0.8 ml, more preferably from about 0.2 ml to about 0.5 ml, and in a preferred use the volume of dose injected may be 0.25 ml. By definition, the volume of one dose means the total volume of vaccine administered at once to one animal.

The vaccine may contain from about $10^{4.5}$ to about $10^{8.0}$ $TCID_{50}$/dose (50% tissue culture infective dose per dose of vaccine) and preferably from about $10^{5.5}$ to about $10^{6.5}$ $TCID_{50}$/dose.

Optionally, the administration can be repeated, as booster administration, at suitable intervals if necessary or desirable, e.g. about from 2 to about 8 weeks after the first administration, and preferably about from 3 to about 5 weeks after the first administration. A booster administration can also be repeated every year.

Another object of the invention is the use of an efficient amount of a DNA vector encoding and expressing at least one PRRSV immunogen as described above and of an acceptable vehicle or diluent, for the preparation of a liquid DNA vector vaccine designed to be administered essentially in the dermis and the hypodermis of an animal of the suidae family using a liquid jet needle-free injector as described above, and resulting in eliciting a safe and protective immune response against PRRSV.

Another object is a vaccination kit or set, comprising such a liquid jet needle-free injector and at least one vaccine vial containing a PRRSV vaccine based on a DNA vector as described above, operatively assembled to perform the administration of the vaccine to an animal of the suidae family. The distribution of the vaccine is essentially done in the dermis and the hypodermis.

Such vaccination kit or set is able to elicit a safe and protective immune response against PRRSV.

The long-term efficacy and safety of a novel formulation specifically designed to be administered transdermally using the Derma-Vac™ NF Transdermal Vaccinator System is presented in Example 4. Needle-free administration has the potential to address both safety and quality aspects of these objectives as well as to provide an optimized presentation of the vaccine to the immune system (see, e.g., Charreyre C., F. Milward, R. Nordgren and G. Royer, 2005, Demonstration of efficacy in pigs of *Mycoplasma* hyopneumoniae experimental vaccines by an innovative needle-free route, Proceedings of the American Association of Swine Veterinarians).

Additional References:

Albina, E. 1997. Epidemiology of porcine reproductive and respiratory syndrome (PRRS): An overview. Veterinary Microbiology 55: 309-316.

Bautista, E. M., Morrison, R. B., Goyal, S. M., Collins, J. E. and Annelli, J. F. 1993. Seroprevalence of PRRS virus in the United States. Swine Health Prod. 1(6): 4-7.

Bautista, E. M., Suarez P., Molitor T. W. 1999. T cell response to the structural polypeptides of porcine reproductive and respiratory syndrome virus. Arch. Virol. 144: 117-134.

Benfield, D. A., Nelson, E. A., Collins, J. E., Harris, L., Goyal, S. M., Robinson, D., Christianson, W. T., Morrison, R. B., Gorcyca, D. and Chladek, D. 1992. Characterization of swine infertility and respiratory syndrome (SIRS) virus (isolate ATCC VR-2332). J. Vet. Diagn. Invest. 4: 127-133.

Brierley, I. 1995. Ribosomal frameshifting on viral RNAs. J. Gen. Virol. 76: 1885-1892.

Brun A., Vaganay, A., Tardy, M. C., Noe, T., Vandeputte, J., Schirvel, C. and Lacoste, F. 1992. Evaluation of etio logical elements in the "P.R.R.S." in pigs. In Proceedings of the 12*" Congress of the International Pig Veterinary Society, The Hague, Netherlands, 17-20 August, p. 108.

Carlson, J. 1992. Encephalomyocarditis virus (EMCV) as a cause of reproductive and respiratory disease in swine. American Association of Swine Practitioners Newsletter. 4: 23.

Cavanagh, D. 1997. Nidovirales: a new order comprising Coronaviridae and Arteriviridae. Arch Virol. 142 (3): 629-633.

Cho, S. H., Freese, W. R., Yoon, I. J., Trigo, A. V. and Joo, H. S. 1993. Seroprevalence of indirect fluorescent antibody to porcine reproductive and respiratory syndrome virus in selected swine herds. J. Vet. Diagn. Invest. 5: 259-260.

Collins, J. E., Benfield, D. A., Christianson, W. T., Harris, L., Hennings, J. C., Shaw, D. P., Goyal, S. M., McCulloygh, S., Morrisson, R. B., Joo, H. S., Gorcyca, D. and Chladek, D. W. 1992. Isolation of swine infertility and respiratory syndrome virus (isolate ATCC VR-2332) in North America and experimental reproduction of the disease in gnotobiotic pigs. J. Vet. Diagn. Invest. 4: 117-126.

Conzelmann, K. K., Visser, N., van Woensel, P. and Tiel, H. J. 1993. Molecular characterization of porcine reproductive and respiratory syndrome virus, a member of the Arterivirus group. Virology 193: 329-339.

Den Boon, J. A., Snijder, E. J., Chirnside, E. D., de Vries, A. A. F., Horzinek, M. C. and Spaan, W. 1991. Equine arteritis virus is not a togavirus but belongs to the coronavirus superfamily. J. Virol. 65: 2910-2920.

De Vries, A. A. F., Horzinek, M. C, Rottier, P. J. M. and de Groot, R. J. 1997. The genome organization of the Nidovirales: Similarities and differences between Arteri-, Toro-, and Coronaviruses. Seminars in Virology 8: 33-47.

Dewey C E, Wilson S, Buck P, Leyenaar J K. 1999. The reproductive performance of sows after PRRS vaccination depends on stage of gestation. Prev Vet Med 40:233-241.

Done, S. H. and Paton, D. J. 1995. Porcine reproductive and respiratory syndrome: clinical disease, pathology and immunosuppression. Veterinary Record 136: 32-35.

Done, S. H., Paton, D. J. and White, M. E. C. 1996. Porcine Respiratory and Reproductive Syndrome (PRRS): A review, with emphasis on pathological, virological and diagnostic aspects. British Veterinary Journal 152 (2): 153-174.

Drew, T. W., Meulenberg, J. J. M., Sands, J. J. and Paton, D. J. 1995. Production, characterization and reactivity of monoclonal antibodies to porcine reproductive and respiratory syndrome virus. J. Gen. Virol. 76: 1361-1369.

Edbauer, C, R. Weinberg, J. Taylor, A. Rey-Senelonge, J. F. Bouquet, P. Desmettre and E. Paoletti, Virology 179, 901-904 (1990).

Faaberg, K. S. and Plagemann, P. G. W. 1995. The envelope proteins of lactate dehydrogenase-elevating virus and their membrane topography. Virology 212: 512-525.

Faaberg, K. S., Even, C, Palmer, G. A. and Plagemann, P. G. W. 1995. Disulfide bonds between two envelope proteins of lactate dehydrogenase-elevating virus are essential for viral infectivity. J. Virol. 69: 613-617.1. Galina, L., Pijoan, C, Sitjar, M., Christianson, W. T., Rossow, K. and Collins, J. E. 1994. Interaction between *Streptococcus suis* serotype 2 and porcine reproductive and respiratory syndrome virus in specific pathogen-free piglets. Vet. Record. 134: 60-64.

Godeny, E. K., Chen, L., Kumar, S. N., Methven, S. L., Koonin, E. V., and Brinton, M. A. 1993. Complete genomic sequence and phylogenetic analysis of the lactate dehydrogenase elevating virus (LDV). Virology 192: 585-596.

Goebel, S. J., G. P. Johnson, M. E. Perkus, S. W. Davis, J. P. Winslow, E. Paoletti, Virology 179, 247-266, 517-563 (1990).

Gonin P, Mardassi H., Gagnon C A, Massie B., Dea S. 1999. A nonstructural and antigenic glycoprotein is encoded by ORF3 of the IAF-Klop strain of porcine reproductive and respiratory syndrome virus. Arch. Virol. 143:1927-1940.

Gonin P, Pirzadeh B, Gagnon C A, Dea S. 1999. Seroneutralization of porcine reproductive and respiratory syndrome virus correlates with antibody response to the GP5 major envelope glycoprotein. J Vet Diagn Invest 11:20-26.

Gorcyca, D., Schlesinger, K., Chladek, D. and Behan, W. 1995. RespPRRS: a new tool for the prevention and control of PRRS in pigs. In Proceedings of the American Association of Swine Practitioners, pp 1-22

Guo, P., S. Goebel, S. Davis, M. E. Perkus, B. Languet, P. Desmettre, G. Allen, and E. Paoletti, J. Virol. 63, 4189-4198 (1989).

Halbur, P. G., Paul, P. S., Meng, X. and Andrews, J. J. 1992. Comparative pathology of porcine reproductive and respiratory syndrome in SPF pigs. Iowa State University Swine Research Reports, p 137. Cooperative Extension Service, Iowa State University, Ames, Iowa, 50011.

Halbur, P. G., Paul, P. S. and Janke, B. H. 1993. Viral contributors to the porcine respiratory disease complex. In Proceedings of the 24$^{th}$ Annual meeting of the American Association of Swine Practitioners, Kansas City, Mo., USA, pp 343-350.

Halbur, P. G., Paul, P. S., Frey, M. L., Landgraf, J., Eernisse, K., Meng, X.-J., Lum, M. A., Andrews, J. J. and Rathje, J. A. 1995. Comparison of the pathology of two U.S. porcine reproductive and respiratory syndrome virus isolates with the Lelystad virus. Vet. Pathol. 32:648-660.

Heinen E, Herbst W, Schmeer N. 1998. Isolation of a cytopathogenic virus from a case of porcine reproductive and respiratory syndrome (PRRS) and its characterization as parainfluenza virus type 2. Arch Virol 143:2233-2239

Hill, H. 1990. Overview and history of mystery swine disease (swine infertility and respiratory syndrome). In. Proceedings of the Mystery Swine Disease Committee Meeting, Denver, Colo., 1990. Livestock Conservation Institute, Madison, Wis., pp 29-30.

Kwang J, Zuckermann F, Ross G, Yang S, Osorio F, Liu W, Low S. 1999. Antibody and cellular immune responses of swine following immunisation with plasmid DNA encoding the PRRS virus ORF's 4, 5, 6 and 7. Res Vet Sci 67:199-201.

Lager K M, Mengeling W L, Brockmeier S L. 1999. Evaluation of protective immunity in gilts inoculated with the NADC-8 isolate of porcine reproductive and respiratory syndrome virus (PRRSV) and challenge-exposed with an antigenically distinct PRRSV isolate. Am J Vet Res 60:1022-1027.

Le Potier, M. F., Blanquefort, P., Morvan, E. and Albina, E. 1995. Results of a control program for PRRS in the French area 'Pays de Loire'. Proc. of the $2^{nc}$ Int. Symposium on PRRS, Copenhagen, Denmark, 9-10 August, p 34.

Mardassi, H., Mounir, S. and Dea, S. 1995. Molecular analysis of the ORFs 3 to 7 of porcine reproductive and respiratory syndrome virus, Quebec reference strain. Arch. Virol. 140: 1405-1418.

Mardassi, H., Massie, B. and Dea, S. 1996. Intracellular synthesis, processing, and transport of proteins encoded by ORFs 5 to 7 of porcine reproductive and respiratory syndrome. Virology 221: 98-112.

Meng, X.-J., Paul, P. S., Halbur, P. G. and Lunn, M. A. 1995a. Phylogenetic analysis of the putative M (ORF6) and N(ORF7) genes of porcine reproductive and respiratory syndrome virus (PRRSV): implications for the existence of two genotypes of PRRSV in the USA and Europe. Arch. Virol. 140: 745-755. 39. Meng, X.-J., Paul, P. S., Halbur, P. G. and Morozov, I. 1995b. Sequence comparison of open reading frames 2 to 5 of low and high virulence United States isolates of porcine reproductive and respiratory syndrome virus. J. Gen. Virol. 76: 3181-3188.

Meng, X.-J., Paul, P. S., Morozov, I. And Halbur, P. G. 1996. A nested set of six or seven subgenomic mRNAs is formed in cells infected with different isolates of porcine reproductive and respiratory syndrome virus. J. Gen. Virol. 77; 1265-1270.

Mengeling W L, Vorwald A C, Lager K M, Clouser D F, Wesley P J D. 1999a. Identification and clinical assessment of suspected vaccine-related field strains of porcine reproductive and respiratory syndrome virus. Am J Vet Res 60:334-340.

Mengeling W L, Lager K M, Vorwald A C. 1999b. Safety and efficacy of vaccination of pregnant gilts against porcine reproductive and respiratory syndrome. Am J Vet Res 60:796-801.

Mengeling W L, Lager K M, Vorwald A C. 1998. Clinical consequences of exposing pregnant gilts to strains of porcine reproductive and respiratory syndrome (PRRS) virus isolated from field cases of "atypical" PRRS. Am J Vet Res 59:1540-1544.

Meulenberg, J. J. M., Hulst, M. M., de Meijer, E. J., Moonen, P. J. L. M., den Besten, A., de Kluyver, E. P., Wensvoort, G. and Moormann, R J. M. 1993a. Lelystad virus, the causative agent of porcine epidemic abortion and respiratory syndrome (PEARS), is related to LDV and EAV. Virology 192: 62-72.

Meulenberg, J. J. M., de Meijer, E. J. and Moormann, R J. M. 1993b. Subgenomic RNAs of Lelystad virus contain a conserved junction sequence. J. Gen. Virol. 74: 1697-1701.

Meulenberg, J. J. M., den Besten, A. P., De Kluyver, E. P., Moormann, R. J. M., Schaaper, W. M. M. and Wensvoort, G. 1995. Characterization of proteins encoded by ORFs 2 to 7 of Lelystad virus. Virology 206: 155-163.

Meulenberg, J. J. M. and Petersen-Den Besten, P.-D. 1996. Identification and characterization of a sixth structural protein of Lelystad virus: The glycoprotein $GP_2$ encoded by ORF 2 is incorporated in virus particles. Virology 225: 44-51.

Murtaugh, M. P., Elam, M. and Kakach, L. T. 1995 Comparison of the structural protein coding sequences of the VR-2332 and Lelystad virus strains of PRRS virus. Arch. Virol. 140: 1451-1460.

Nakamine M, Kono Y, Abe S, Hoshino C, Shirai J, Ezaki T. 1998. Dual infection with enterotoxigenic *Escherichia coli* and porcine reproductive and respiratory syndrome virus observed in weaning pigs that died suddenly. J Vet Med Sci 60:555-561.

Nelsen C J, Murtaugh M P, Faaberg K S. 1999. Porcine reproductive and respiratory syndrome virus comparison: divergent evolution on two continents. J Virol 73:270-280.

Nelson, E. A., Christopher-Hennings, Drew, T., Wensvoort, G., Collins, G. and Benfield, D. A. 1993. Differentiation of US and European isolates of porcine reproductive and respiratory syndrome virus by monoclonal antibodies. J. Clin. Micro. 31: 3184-3189.

Ohlinger, V., Haas, B., Saalmuller, A., Beyer, J., Teuffert, J., Visser, N. and Weiland, F. 1992. In vivo and in vitro studies on the immunobiology of PRRS. Proc. of American Assoc. Swine Practitioners—$1^{st}$ Int. PRRS Symp., 4(4): 24.

Ohlinger V F. 1995. The respiratory syndrome: studies on PRRSV-replication and immune response. Int. Symp. PRRS 2:12.

Panicali, D. and E. Paoletti, Proc. Natl. Acad. Sci. USA 79, 4927-4931 (1982).

Pirzadeh B, Dea S. 1998a. Immune response in pigs vaccinated with plasmid DNA encoding ORF5 of porcine reproductive and respiratory syndrome virus. J Gen Virol 79:989-999.

Pirzadeh B, Gagnon C A, Dea S. 1998b. Genomic and antigenic variations of porcine reproductive and respiratory syndrome virus major envelope GP5 glycoprotein. Can J Vet Res 62:170-177

Paoletti, E., B. R. Lipinskaks, C. Samsonoff, S. Mercer, and D. Panicali, Proc. Natl. Acad. Sci. U.S.A. 81, 193-197 (1984). 58. Paton, D. J., Brown, I. H., Edwards, S, and Wensvoort, G. 1991. Blue ear disease of pigs. Vet. Rec. 128: 617.

Perkus, M. E., K. Limbach, and E. Paoletti, J. Virol. 63, 3829-3836 (1989).

Piccini, A., M. E. Perkus, and E. Paoletti, In Methods in Enzymology, Vol. 153, eds. Wu, R, and Grossman, L., (Academic Press) pp. 545-563 (1987).

Pirzadeh, B. and Dea, S. 1997. Monoclonal antibodies to the ORF5 product of porcine reproductive and respiratory syndrome virus define linear neutralizing determinants. J. Gen. Virol. 78: 1867-1873.

Plagemann, P. G. W. 1996. Lactate dehydrogenase-elevating virus and related viruses. In "Virology" (B. N. Fields, D. M. Knipe and P. M. Howley, Eds.) 3$^{rd}$ ed., pp 1105-1120. Raven Press, New York.

Plana-Duran J, Bastons M, Urniza A, Vayreda M, Vila X, Mane H. 1997. Efficacy of an inactivated vaccine for prevention of reproductive failure induced by porcine reproductive and respiratory syndrome virus. Vet Microbiol 55:361-370.

Plana Duran, J., Climent, I., Sarraseca, J., Urniza, A., Cortes, E., Vela, C. and Casal, I. 1997. Baculovirus expression of proteins of porcine reproductive and respiratory syndrome virus strain Olot/91. Involvement of ORF3 and ORF5 proteins in protection. Virus Genes 14: 19-29.

Rossow K. D. 1998. Porcine reproductive and respiratory syndrome (review article). Vet Pathol. 35:1-20.

Sirinarumitr T, Zhang Y, Kluge J P, Halbur P G, Paul P S. 1998. A pneumo-virulent United States isolate of porcine reproductive and respiratory syndrome virus induces apoptosis in bystander cells both in vitro and in vivo. J Gen Virol 79:2989-2995.

Snijder E., van Tol H., Pedersen K. W., Raamsman M. J. B., and de Vries A. A. F. 1999. Identification of a novel structural protein of arteri viruses. J. Virol. 73, 6335-6345.

Suarez, P., Diaz-Guerra, M., Prieto, C, Esteban, M., Castro, J. M., Nieto, A. and Ortin, J. 1996. Open reading frame 5 of porcine reproductive and respiratory syndrome virus as a cause of virus-induced apoptosis. J. Virol. 70: 2876-2882. 69. Sur J H, Doster A R, Osorio F A. 1998. Apoptosis induced in vivo during acute infection by porcine reproductive and respiratory syndrome virus. Vet Pathol 35:506-514.

Thacker E L, Halbur P G, Ross R F, Thanawongnuwech R, Thacker B J. 1999. *Mycoplasma* hyopneumoniae potentiation of porcine reproductive and respiratory syndrome virus-induced pneumonia. J Clin Microbiol 37:620-627.

Van Nieuwstadt, A. P., Meulenberg, J. J. M., van Essen-Zandbergen, A., Petersen-den Besten, A., Bende, R. J., Moorman, R J. M. and Wensvoort, G. 1996. Proteins encoded by open reading frames 3 and 4 of the genome of Lelystad virus (Arteriviridae) are structural proteins of the virion. J. Virol. 70: 4767-4772.

van Woensel P A, Liefkens K, Demaret S. 1998a. Effect on viraemia of an American and a European serotype PRRSV vaccine after challenge with European wild-type strains of the virus. Vet Rec 142:510-512. 81. van Woensel P A, Liefkens K, Demaret S. 1998b. European serotype PRRSV vaccine protects against European serotype challenge whereas an American serotype vaccine does not. Adv Exp Med Biol 440:713-718.

Weiland E, Wieczorek-Krohmer M, Kohl D, Conzelmann K K, Weiland F. 1999. Monoclonal antibodies to the GP5 of porcine reproductive and respiratory syndrome virus are more effective in virus neutralization than monoclonal antibodies to the GP4. Vet Microbiol 66:171-186

Wensvoort, G. C., Terpstra, J. M. A., Pol, E. A., ter Laak, M., Bloemraad, E. P., de Kluyver, C, Kragten, C, van Buiten, A., den Besten, F., Wagenaar, J. M., Broekhuysen, P. L. J. M., Moonen, T., Zetstra, E. A., de Boer, H J., Tibben M. F., de Jong, P., van't Veld, G. J. R., Greenland, A., van Gennep, M. T., Voets, J. H. M., Verheyden, J. H. M. and Braamskamp, J. 1991. Mystery swine disease in The Netherlands: the isolation of Lelystad virus. Vet Q. 13: 121-130.

Wensvoort, G., de Kluyver, E. P., Luijtze, E. A., den Besten, A., Harris, L., Collins, J. E., Christianson, J. E. and Chladek, D. 1992. Antigenic comparison of Lelystad virus and swine infertility and respiratory syndrome (SIRS) virus. J. Vet. Diagn. Invest. 4: 134-138.

Yeager, M. J., Prieve, T., Collins, J., Christopher-Hennings, J., Nelson, E. and Benfield, D. 1993. Evidence for the transmission of porcine reproductive and respiratory syndrome (PRRS) virus in boar semen. Swine Health Prod. 1(5): 7-9.

Yoon, K.-J., Zimmermann, J. J., Swenson, S. L., Wills, R. W., Hill, H. T. and Platt, K. B. 1994. Assessment of the biological significance of antibody dependent enhancement (ADE) of porcine epidemic abortion and respiratory syndrome (PEARS) virus infection in passively immunized pigs. Proc. 13^ Int. Pig Vet. Soc. Congress, p 69.

Yoon, K.-J., Zimmerman, J. J., Swenson, S. L., McGinley, M. J., Eernisse, K. A., Brevik, A., Rhinehart, L. L., Frey, M. L., Hill, H. T. and Platt, K. B. 1995. Characterization of the humoral immune response to porcine reproductive and respiratory syndrome (PRRS) virus infection. J. Vet. Diagn. Invest. 7: 305-312. Zimmermann, J. J., Yoon, K.-J., Wills, R. W. and Swenson, S. L. 1997. General Overview of PRRSV: A perspective from the United States. Veterinary Microbiology 55: 187-196.

The invention will now be further described by way of the following non-limiting examples.

EXAMPLE 1

Construction and Characterization of the Plasmids Encoding for Nucleocapsid Gene (ORF7)

The PRRSV ORF7 gene (SEQ ID NO:1) and the genetically modified truncated ORF7 (ORF7t) gene (SEQ ID NO:3), with a stop codon after amino acid 112, were PCR amplified from the vector pBAD-ORF7 (SEQ ID NO:13) containing the nucleocapsid gene (ORF7) of the US-genotype That PRRSV isolate (01NP1), using the primer sets indicated in Table 1.

TABLE 1

PRRSV-ORF7 and truncated ORF7 (ORF7t) gene cloning primers

| Name | Sequence | Target | Amplicon length (bp) | SEQ ID NO |
|---|---|---|---|---|
| ORF7 US-F | 5'-AAAAAAGAATTCATGCCAAATAACAACGGCAAG-3' | 1-21 | 384 | 5 |
| ORF7 US-R | 5' AAAAAAGAATTCTCATGCTGAGGGTGATGCTGTG 3' | 372-351 | | 6 |

TABLE 1-continued

PRRSV-ORF7 and truncated ORF7 (ORF7t) gene cloning primers

| Name | Sequence | Target | Amplicon length (bp) | SEQ ID NO |
|---|---|---|---|---|
| OEF7 US-F | 5' AAAAAAGAATTCATGCCAAATAACAACGGCAAG 3' | 1-21 | 351 | 5 |
| US-11R | 5' AAAAAAGAATTCTCACACAGTATGATGCGTAGGC 3' Stop Codon | 336-318 | | 7 |

Note:
Italic cases indicate the EcoRI restriction sites

The ORF7 and ORF7t fragments were then cut with EcoRI and cloned into the EcoRI cut pMASIA vector (SEQ ID NO:8). The cloned plasmids were transformed into the competent cells, *E. coli* strain JM109. The obtained constructs were referred as pORF7 (SEQ ID NO:9) and pORF7t (SEQ ID NO:10), respectively (FIG. 1). The orientation of the inserted ORF genes was initially confirmed by PCR analysis, using the primer sets indicated in Table 2. The selected plasmids were further subjected to sequence analyses of the ORF7 gene. All of the sequence analyses confirmed the correct insertion of the ORF7 gene, with identical sequences to the original ORF7 sequences from the original vector (pBAD-RF7) and the 01NP1-PRRSV (Genbank, Q056373, SEQ ID NO:13), (FIG. 2).

PAGE, and transferred to the PVDF membrane. The presence of PRRSV protein was determined using porcine anti-PRRSV hyperimmune serum. (U; unpurified protein, P; purified protein, +; with IPTG, −; without IPTG; M; Molecular weight marker).

Figure 5:
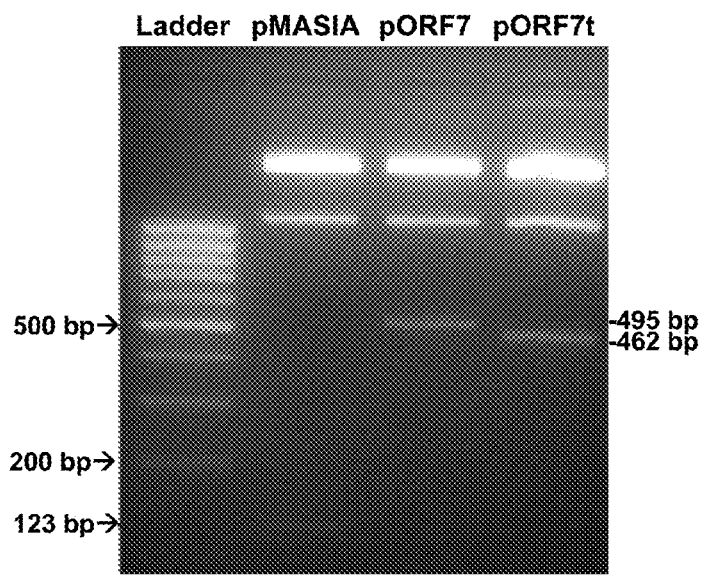
FIG. 5 is an agarose gel image depicting the NcoI restriction analyses of pMASIA, pORF7, and pORF7t.

For preparation of the DNA vaccine, the *E. coli* transformants were propagated and subjected to plasmid purification, using the commercial plasmid purification column (NucleoBond endotoxin free plasmid purification, Macherey-Nagel). The confirmation of the purified plasmids was performed by restriction analyses, using the restriction enzyme NcoI (FIG. 5). The concentration of the plasmid was

TABLE 2

The primers used for analysis of the orientation of the inserted ORF7 genes

| Name | Sequence | Target | Amplicon length (bp) | SEQ ID NO |
|---|---|---|---|---|
| pMASIA F | 5'-CAGTGTAGTCTGAGCAGTACT-3' | 4100-4120 | 564 | 11 |
| ORF7 US-F | 5'-AAAAAAGAATTCATGCCAAATAACAACGGCAAG-3' | 1-21 | | 5 |
| pMASIA F | 5'-CAGTGTAGTCTGAGCAGTACT-3' | 4100-4120 | 564 | 11 |
| ORF7 US-R | 5'-AAAAAAGAATTCTCATGCTGAGGGTGATGCTGTG-3' | 372-351 | | 6 |
| pMASIA F | 5'-CAGTGTAGTCTGAGCAGTACT-3' | 4100-4120 | 531 | 11 |
| US-11R | 5'-AAAAAAGAATTCTCACACAGTATGATGCGTAGGC-3' | 336-318 | | 7 |

The expression of the ORF7 genes by the plasmid constructs, was verified by in vitro transfection of the freshly isolated porcine peripheral blood mononuclear cells (PBMC) with the pORF7 or pORF7t. Briefly, the PBMC were transfected with pORF7 or pORF7t, using Effectene Transfection reagent (Qiagen, Germany), according to the manufacturer's protocol. The cells were further incubated for 48 hrs, in a 5%, CO2 incubator. Following incubation, the PBMC samples were harvested, and subjected for total RNA isolation using the commercial RNA extraction kit (Macherey-Nagel, Germany). Contaminated DNA was removed by addition of DNase I supplied with the kit. The expression of the ORF7 gene in the transfected PBMC was determined by the cDNA synthesis using random hexamers, followed by the PCR reaction, using the previously described primer sets (Table 1). The result confirmed the expression of the ORF7 mRNA from both pORF7 and pORF7t, as shown in FIG. 3.

In addition, when subcloned into an expression vector (pQE31, SEQ ID NO:18), the ORF7 and ORF7t genes could correctly produce the recombinant proteins with a correct molecular weight (approx. 15 kDa), and could be detected using porcine anti-PRRSV hyperimmune serum (FIG. 4). The recombinant proteins were subjected to 15% SDSdetermined by spectrophotometer. The OD260/OD280 ratios obtained from each preparation ranged between 1.625-1.69.

EXAMPLE 2

The Immunomodulatory Effects of the PRRSV DNA Vaccine in the Challenged Model

Experimental Design (FIG. 6).
To determine the immunomodulatory effects of the PRRSV DNA vaccine, four-week-old, PRRSV-seronegative, crossbred pigs (4-6 pigs/group) were immunized with 500 μg of pORF7t or pORF7 diluted in 200 μl Ca2+, Mg2+-free PBS (referred as PBSA), of the plasmids twice at 4 weeks interval (d0, d28). The plasmid was intradermally injected into the skin of both ears (2×50 μl/side), using a tuberculin syringe (FIG. 7). The control groups receiving the same amount of PBS or null plasmid (pMASIA) were also included in the study. Four weeks following the second vaccination (d56), the pigs were intranasally challenged with 5 ml (2.5 ml/nostril) of the virulent PRRSV (01NP1) at the concentration of $10^{5.5}$ TCID$_{50}$/ml. The immunological parameters and clinical signs were monitored every 2 weeks and at 0, 5, and 10 days post infection (dpi). The pigs were sacrificed at 10 dpi and subjected to pathological examination and virological studies.

Virological and Pathological Studies.

Figure 8:
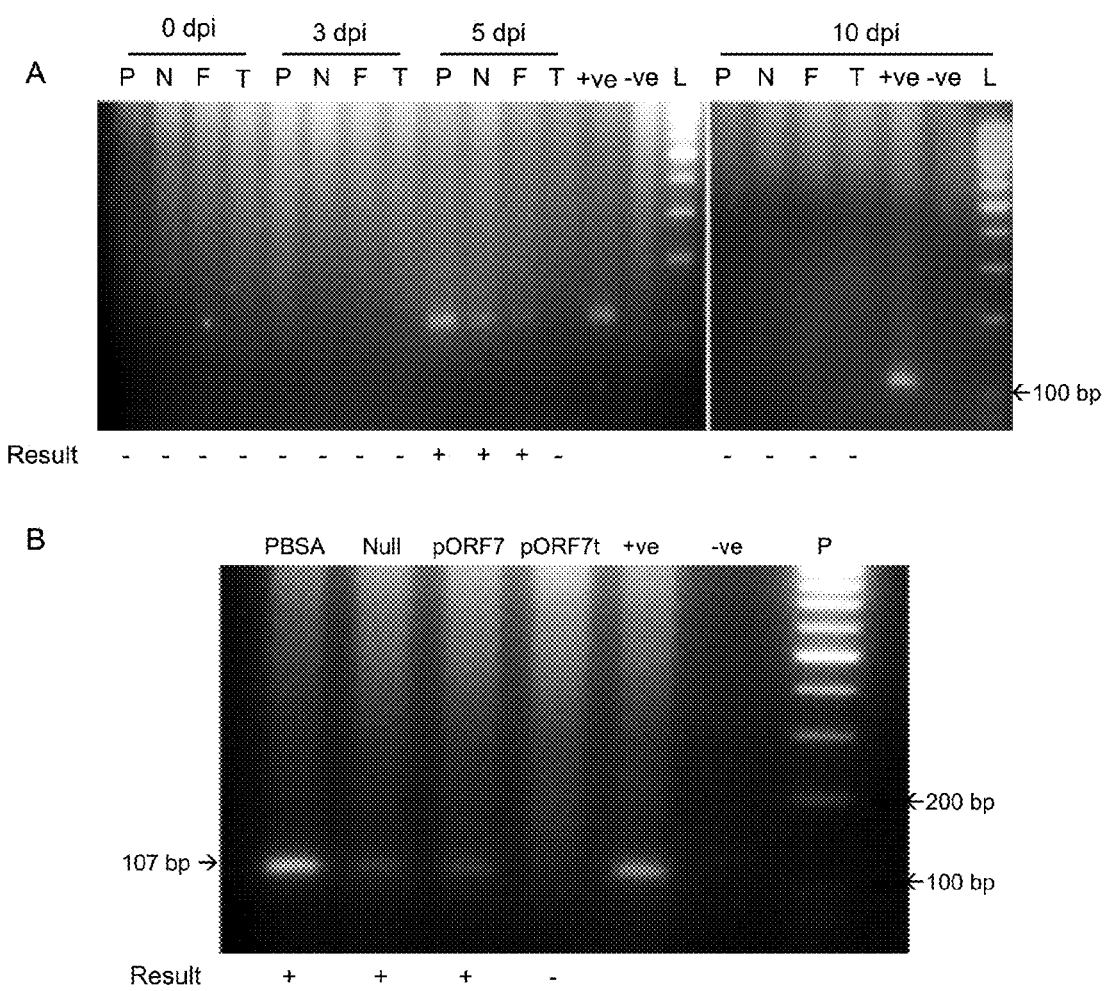
FIG. 8A is a gel image indicating the presence of PRRSV in the pooled serum samples during the experiment from the experimental pigs immunized with PBSA (P), null plasmid (N), pORF7 (F), and pORF7t (T)
FIG. 8B is a gel image indicating the presence of PRRSV in the pooled lung tissue samples at 10 days post infection from the experimental pigs immunized with PBSA (P), null plasmid (N), pORF7 (F), and pORF7t (T)

There were no clinical signs, nor adverse reactions observed following DNA immunization process. Following the challenge, the presence of PRRSV in the pooled samples was initially determined by RT-PCR using the ORF1-specific primer set. PRRSV was detected in the samples of the groups immunized with pORF7, Null plasmid and PBSA, at 5 dpi (serum), and 10 dpi (lung tissues). However, PRRSV was not detected in the group immunized with pORF7t at any time of this study (FIG. 8). In addition, the presence of PRRSV in the lung tissues of individual pigs was assessed by RT-PCR. The presence of PRRSV genome was determined by RT-PCR using the ORF1-specific primer sets, which would give the 107 bp PCR product in the positive sample (Gilbert et al., J Clin Microbiol. 1997. 35:264-7). +ve; positive control (PRRSV-US genotype), −ve; negative control (ddH20), L; 100 bp ladder. Consistent to the results from pooled samples, PRRSV could be detected in all groups except the group immunized with pORF7t (Table 3).

TABLE 3

Vaccination groups and results indicating the presence of PRRSV in the lung tissue samples of the pigs at 10 dpi

| Group | Sample ID | Results | % positive samples |
|---|---|---|---|
| pORF7t | H4811 | − | 0 |
|  | H4831 | − |  |
|  | H4841 | − |  |
|  | H4853 | − |  |
|  | H4849 | − |  |
|  | H4809 | − |  |
| pORF7 | H4843 | + | 33 |
|  | H4875 | + |  |
|  | H4871 | − |  |
|  | H4827 | − |  |
|  | H4823 | − |  |
|  | H4813 | − |  |
| Null plasmid | H4867 | − | 50 |
|  | H4923 | + |  |
|  | H4893 | − |  |
|  | H4859 | + |  |
|  | H4897 | + |  |
|  | H4861 | − |  |
| PBSA | H4863 | + | 50 |
|  | H4865 | − |  |
|  | H4895 | − |  |
|  | H4869 | + |  |

TABLE 4

Percentage of pigs in each group presenting pathological changes in the respiratory tract at 10 dpi.

| Pathological lesions | Experimental group | | | |
|---|---|---|---|---|
|  | PBSA[a] | Null[b] | pORF7[b] | pORF7t[b] |
| Pneumonia | 75.0 | 33.2 | 33.2 | 50.0 |
| Lymphadenopathy (Tracheobronchial Ln.) | 50.0 | 16.6 | 0 | 16.6 |
| Fibrinous pleuritis | 0 | 16.6 | 16.6 | 0 |

[a]n = 4;
[b]n = 6

However, there were no significant differences in the number of experimental pigs with pathological changes in the respiratory tract at 10 dpi (Table 4). The data suggested that immunization with pORF7t could enhance viral clearance in the experimentally challenged pigs.

Study of Humoral Immune Responses.

The PRRSV-specific antibody response was determined by the commercial ELISA test kit (HerdChek PRRS, IDEXX, Germany). It should be pointed out that nucleocapsid protein is the major epitope recognized by the anti-PRRSV antibody determined by IDEXX HerdChek ELISA assay (Plagemann, 2006. J Virol Methods. 134: 99-118). The pigs were PRRSV-seronegative at the beginning of the experiment. The seroconversion was only observed in the group that received pORF7 on the challenge day (1 pig), and at 10 dpi (3 pigs), suggesting the priming of anti-PRRSV antibody response by pORF7 immunization. However, no seroconversion was observed in the pigs immunized with pORF7t or the controls throughout the experiment (Table 5).

TABLE 5

Anti-PRRSV antibody responses in the experimental pigs during the experiment

| Group | Mean S/P ratio (% seroconversion[a]) | | | |
|---|---|---|---|---|
|  | d 0 | d 56 (0 dpi) | d 61 (5 dpi) | d 66 (10 dpi) |
| ORF7t | 0.08 (0) | 0.02 (0) | 0.02 (0) | 0.03 (0) |
| ORF7 | 0.07 (0) | 0.15 (16.6) | 0.04 (0) | 0.46 (50) |
| Null | 0.11 (0) | 0.04 (0) | 0.01 (0) | 0.02 (0) |
| PBSA | 0.06 (0) | 0.03 (0) | 0.02 (0) | 0.01 (0) |

[a]S/P ratio ≥ 0.4 = positive

Study of the Viral-Specific Cytokine Production in the PBMC.

Figure 9:
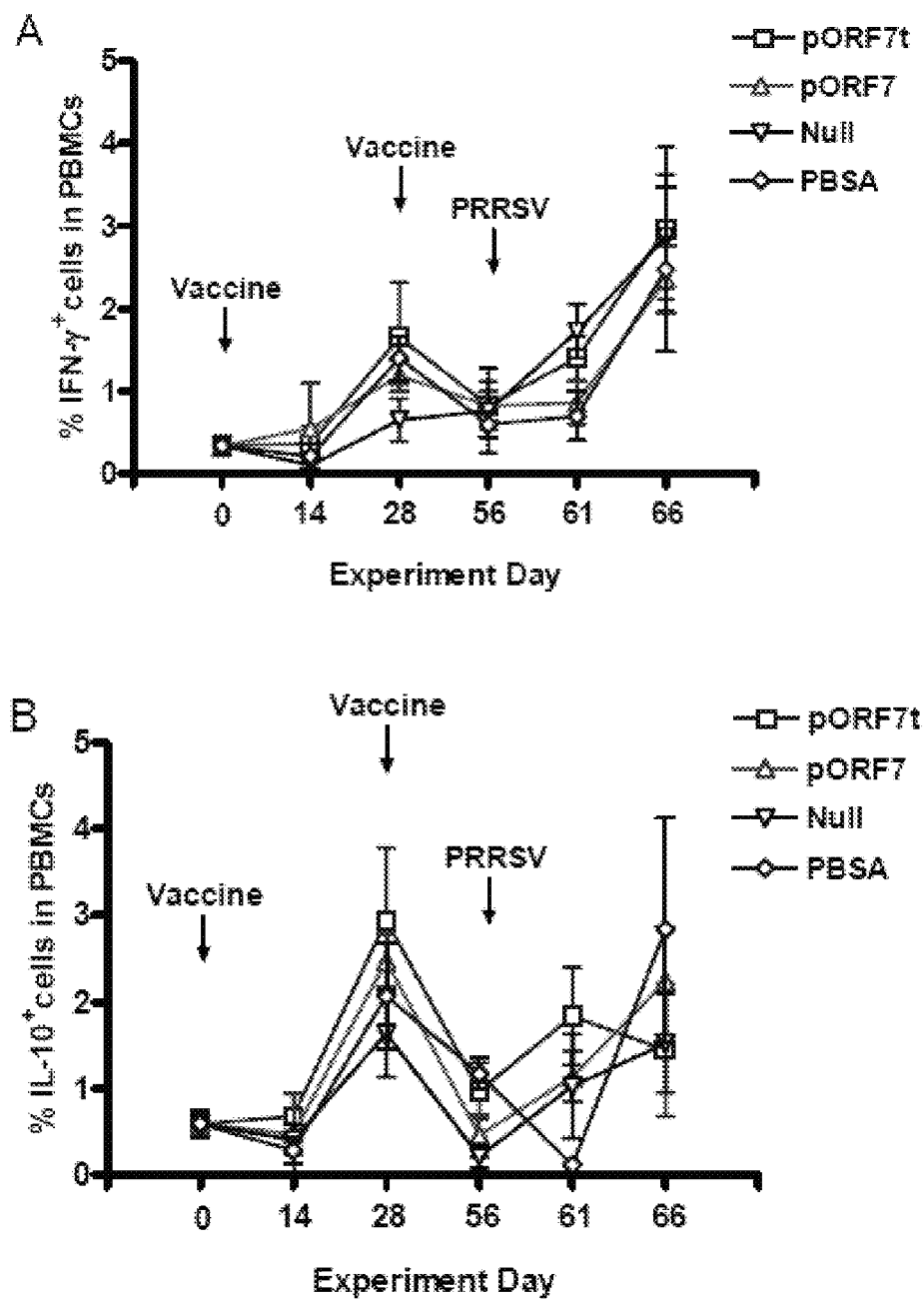
FIG. 9A is a graph of the numbers of PRRSV-specific IFNγ+ in the PBMC.
FIG. 9B is a graph of the numbers of IL-10+ cells in the PBMC.

There were no significant differences in the PRRSV-specific IFNγ and IL-10 producing cells among the groups prior to the challenge. Following the challenge, increased numbers of PRRSV-specific IFNγ and IL-10 producing cells were observed in all groups (FIG. 9). Pigs were immunized with the vaccine indicated in the legend twice on d0 and d28, and received PRRSV inoculation on d56. The freshly isolated porcine PBMCs were cultured in vitro with 0.08 m.o.i. of the virulent US-PRRSV (strain 01NP1), or mock infected MARC-145 lysate for 48 hrs prior to harvesting for fluorescent staining and flow cytometric analyses. The data represents mean percentage (±SEM) of the cytokine-producing cells from the pigs in the same group, which was calculated from % cytokine producing cells obtained from the PRRSV-cultured PBMC–% cytokine-producing cells obtained from the mock-cultured PBMC.

Study of the Viral-Specific CD4+CD25+ and CD4+ CD25+Foxp3+ Cells in the PBMC.

Figure 10:
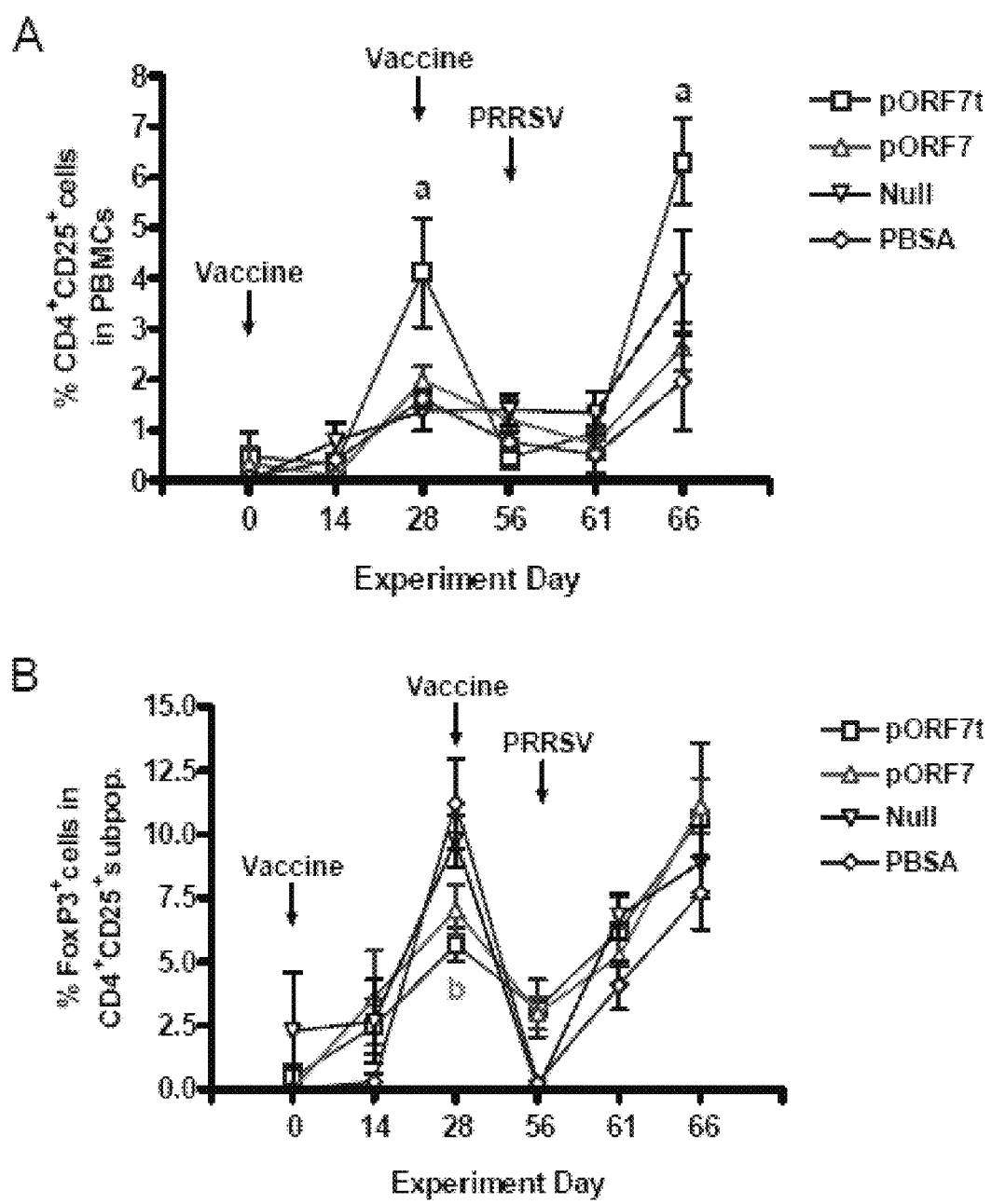
FIG. 10A is a graph of the numbers of PRRSV-specific CD4+CD25+ in the PBMC.
FIG. 10B is a graph of the numbers of CD4+CD25+ Foxp3+ cells (B) in the PBMC.

Following the first immunization, the pigs immunized with pORF7t exhibited significantly higher number of the PRRSV-specific CD4+C25+ cells (activated Th lymphocytes) than the other groups (p<0.05, ANOVA followed by Newman Keuls test), (FIG. 10A). The enhanced number of the CD4+CD25+ was also observed in the pORF7t immunized group following the challenge (d66). Interestingly, the numbers of PRRSV-specific CD4+CD25+Foxp3+ cells (regulatory T cells; Treg) in the group receiving the pORF7t and pORF7 were significantly lower than the control groups (p<0.05, ANOVA followed by Newman Keuls) at d28. Following the viral challenge, all groups exhibited increased numbers of CD4+CD25+Foxp3+ cells in the PBMCs (FIG. 10B). The data represents mean percentage (±SEM) of the lymphocyte subpopulation from the pigs in the same group, which was calculated from % of the lymphocyte subpopulation obtained from the PRRSV-cultured PBMC–% of the lymphocyte subpopulation obtained from the mock-cultured PBMC. "a" indicates significant difference from the other treatments. "b" indicates significant difference between the groups receiving the DNA vaccine (pORF7t or pORF7) and the controls (null or PBSA). Further, the data indicated that the 2 plasmids could modulate the immune responses against PRRSV, by reduction of the viral-specific Treg, and that pORF7t could enhance the numbers of viral-specific responder Th cells in the pigs following immunization and the challenge.

Conclusion.

The data from this challenge experiment indicates that the DNA immunization with plasmid encoding ORF7 (pORF7t or pORF7) could significantly modulate the anti-PRRSV immunity. The pORF7t, but not pORF7, induced higher numbers of the viral-specific responder Th cells and viral clearance following the challenge, without the evidence of priming of anti-PRRSV antibody response. Although pORF7 could prime the pigs for the anti-PRRSV antibody response, the plasmid did not enhance anti-viral immunity or viral clearance in the immunized pigs (Table 6). The result emphasized the important role of anti-PRRSV cell-mediated immunity on the anti-PRRSV immunity. In addition, the data from this experiment suggested the superior immunomodulatory effects of the pORF7t compared to the pORF7, therefore, the plasmid pORF7t was selected for the subsequent experiment.

TABLE 6

Summary of the effects of plasmid immunization on anti-PRRSV immunity

| | IFN- | IL-10 | $CD4^+CD25^+$ lymphocytes | $CD4^+CD25^+$ $FoxP3^+$ cells | Sero- conver- sion | Enhanced viral clearance |
|---|---|---|---|---|---|---|
| Pre-challenge | | | | | | |
| Null | — | — | — | — | — | na[c] |
| pORF7t | — | — | ↑[a] | ↓[b] | — | na |
| pORF7 | — | — | — | ↓[b] | — | na |
| Post-Challenge | | | | | | |
| Null | — | — | — | — | — | — |
| pORF7t | — | — | ↑[a] | — | — | yes |
| pORF7 | — | — | — | — | yes | — |

[a]significant difference from the other treatments (p < 0.05)
[b]significant difference between the groups receiving the DNA vaccine (pORF7t or pORF7) and the controls (null or PBSA), (p < 0.05)
[c]not applicable

EXAMPLE 3

The Immunomodulatory Effects of pORF7t in the Pigs in the Commercial Farm (Long-Term Study)

The objective was to study the immunomodulatory effects of pORF7t in the PRRSV-positive, commercial farm. Specific Aims: 1. To investigate the immunomodulatory effect of the DNA vaccine on the anti-PRRSV immunity, when immunized prior to infection (priming exp.); 2. To investigate the immunomodulatory effects of the DNA vaccine on the anti-PRRSV immunity, when immunized at the time of infection (treatment exp.); 3. To investigate the effect of DNA immunization on the growth and performance of the immunized pigs Experimental Design The selected farm for the long-term study was a PRRSV-positive farm with known PRRSV serological status during the past 2 years. The farm was situated approximately 160 km from Bangkok. It had approximately 3,000 sows, and employed a continuous flow rearing system. Generally, the piglets were weaned at 4 weeks old, and kept at the nursery at the same site (unit 1) until 11 weeks old and subsequently moved to the finisher (unit 2), situated approximately 20 km from the nursery. It is during this time (i.e. 4-11 weeks) that most of the pigs become infected with PRRSV. The pigs were kept at finisher (unit 2) until 26-28 weeks old.

Figure 11:
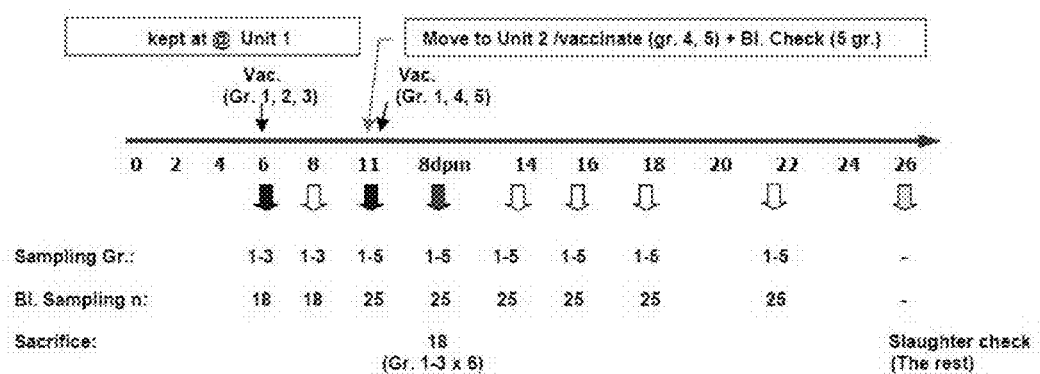
FIG. 11A presents an overview of the experimental plan described in Example 3.
FIG. 11B presents clinical tests performed during the study.

Experimental Pig:

Six week-old, male weanling pigs were randomly grouped into 5 groups (30 pigs/group) according to scheme presented in Table 7. Additional details of the experiment are illustrated in FIG. 11A.

TABLE 7

Details of the experimental groups

| Group | Vaccination Age | No. @ start | Culled @ 8 dpm | Expected No. @ slaughter |
|---|---|---|---|---|
| 1. Control (PBSA) | 6, 11 wk | 30 | 6 | 24 |
| 2. pORF7t-prime | 6 wk | 30 | 6 | 24 |
| 3. Null-prime | 6 wk | 30 | 6 | 24 |
| 4. pRF7t-Tx | 11 wk | 30 | | 30 |
| 5. Null-Tx | 11 wk | 30 | | 30 |

The DNA Priming (DNA-P):

The pigs were intradermally immunized with 500 μg of pORF7t at 6 wks old (d0). The pigs receiving the same amount of null plasmid (pMASIA), or PBSA were included as the controls. At 8 days post moving (8 dpm, d43), the pigs (6/group) were euthanized and subjected for pathological and virological studies—The DNA treatment (DNA-T): The pigs were immunized with 500 μg of pORF7t at the time of moving (wk 11, d35). The control groups included the group immunized with the null plasmid or PBSA.—Blood samples were collected every 2 wks. The numbers of PRRSV-specific Treg, IL-10 and IFNγ producing cells in the PBMC were determined by flow cytometry. Serum samples were collected for determining of the anti-PRRSV antibody and the presence of PRRSV. Clinical signs and performance indexes were monitored until the end of a finishing period (FIG. 11B).

Immunomodulatory Effects of the DNA Vaccine when Immunized Prior to PRRSV Exposure (PRIMING EXPERIMENT)

All groups had comparable levels of cytokine producing cells at the beginning of the experiment. After moving to the finisher (d43), all the groups exhibited significantly increased numbers of PRRSV-specific IL-10+ cells, possibly due to the natural exposure to PRRSV at the finisher. The levels of the numbers of IL-10+ producing cells gradually decreased after d56. Interestingly, the groups receiving either pORF7t or the null plasmid had significantly lower number of PRRSV-specific IL-10+ cells than the control PBSA at d70 (p<0.05, ANOVA followed by Tukey's multiple comparison tests). However, only the group immunized with pORF7t exhibited gradual decreased of the PRRSV-specific IL-10+ cells through the end of the observation period. By d112, the pigs vaccinated with pORF7t had significantly lower number of the IL-10+ lymphocytes than the other groups (p<0.05, ANOVA followed by Tukey's multiple comparison tests), (FIG. 12A, B). Following the DNA vaccination (d14), the pigs receiving pORF7t exhibited significant increase in the number of PRRSV-specific IFNγ+ lymphocytes. The number of the PRRSV-specific IFNγ+ cells remained higher than other groups until d70 (FIG. 12C, D). Pigs were vaccinated with pORF7t, null plasmid, or PBSA on d0, and moved to the finisher unit on d35. The freshly isolated porcine PBMC samples had been cultured with 0.1 m.o.i. of US-PRRSV (strain 01NP1), or mock-infected MARC-145 lysate for 48 hrs prior to fluorescent staining and flow cytometric analyses. All groups had comparable numbers of PRRSV-specific CD4+CD25+ Foxp3+ cells (Treg) at the beginning of the experiment. Following vaccination, the pigs receiving pORF7t exhibited significantly lower numbers of the PRRSV-specific Treg than the other control groups (p<0.05, ANOVA followed by Tukey's multiple comparison tests). Following the movement (d43), the numbers of PRRSV-specific Treg increased in every group, possibly due to the PRRSV exposure. However, the number of the PRRSV-specific Treg in the pORF7t vaccinated group remained lower than the other groups throughout the experiment (FIG. 13A, B). The result from this experiment indicated that the DNA vaccine could modulate the anti-PRRSV immune responses in the pigs, by enhancing the production of viral-specific IFNγ and reducing the viral-specific IL-10 and Treg production in the vaccinated pigs following the viral exposure.

Immunomodulatory Effect of the DNA Vaccine when Immunized at the Time of PRRSV Exposure (Treatment Experiment).

All the pigs exhibited increased PRRSV-specific IL-10+ cells in the PBMC following the movement into the finisher unit (d43). However, the pigs receiving pORF7t exhibited faster reduction of the PRRSV-specific IL-10+ cells and had lower levels of PRRSV-specific IL-10+ cells than the other control groups until the end of the observation period (FIG. 14A, B). Immunization with pORF7t resulted in an enhanced induction of PRRSV-specific IFNγ+ cells. Furthermore, the numbers of the PRRSV-specific IFNγ cells in the pORF7t group remained higher than the other groups throughout the end of the experiments (FIG. 14C, D). Furthermore, the pigs received pORF7t exhibited significantly lower numbers of PRRSV-specific CD4+CD25+ Foxp3+ cells than the control groups throughout the experiment (FIGS. 15A-B). The results suggested that pORF7t could modulate the PRRSV-specific immune responses that should be benefit to the anti-PRRSV immunity.

The Effect of DNA Immunization on Antibody Responses

Figure 16:
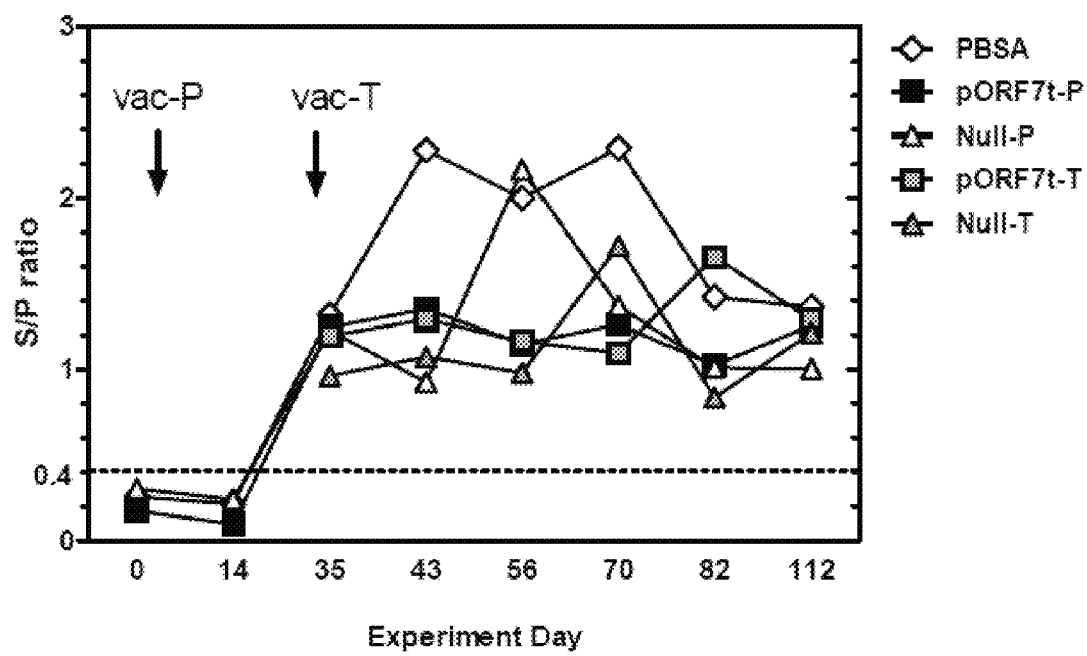
FIG. 16 is a graph of PRRSV-specific antibody responses, as measured by IDEXX ELISA

Some of the pigs contained maternal-derived PRRSV-specific antibody in their serum at the beginning of the experiment. The level of MDA gradually reduced until 8 wks old (d14). However, 80-100% of the pigs in every groups exhibited seroconversion at the time of moving (d35), suggesting that the natural infection actually occurred at the end of the nursery period. There were no significant different in the pattern of antibody responses, measured by ELISA, among the experimental groups (Table 8, FIG. 16).

TABLE 8

PRRSV-specific antibody determined by IDEXX ELISA

Mean S/P ratio[a] (% seropositive pigs[b])

| Group | d0 | d14 | d35 | d43 | d56 | d70 | d82 | d112 |
|---|---|---|---|---|---|---|---|---|
| PBSA | 0.25(33.3) | 0.21(33.3) | 1.31(100) | 2.28(100) | 1.99(80) | 2.29(100) | 1.42(100) | 1.36(100) |
| pORF7t-P | 0.17(16.7) | 0.09(0) | 1.24(100) | 1.35(100) | 1.15(100) | 1.26(80) | 1.02(100) | 1.26(100) |
| Null-P | 0.30(33.3) | 0.24(0) | 1.22(100) | 0.93(100) | 2.16(100) | 1.36(100) | 1.01(80) | 1.00(60) |
| pORF7t-T | nd | nd | 1.19(80) | 1.29(100) | 1.16(100) | 1.09(100) | 1.65(100) | 1.29(100) |
| Null-T | nd | nd | 0.96(80) | 1.07(80) | 0.98(80) | 1.72(80) | 0.83(100) | 1.21(100) |

[a]mean OD values from 5 pigs/group
[b]S/P ratio ≥ 0.4 = seropositive

The Virological Studies.

Figure 17:
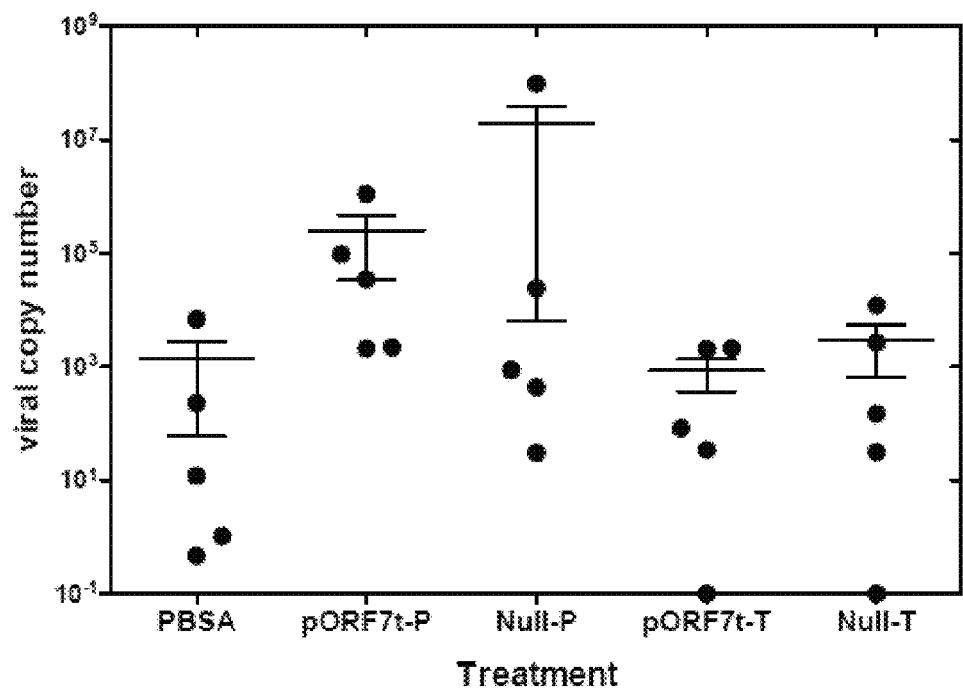
FIG. 17 is a plot of the PRRSV viral load in the serum of the experimental pigs at d43

The virological studies by RT-PCR and quantitative RT-PCR confirmed presence of the US genotype PRRSV in the lung samples of the experimental pigs that were sacrificed at 8 dpm (d43), Table 9. However, there were no different in the number of viral load in the serum at d43 (FIG. 17). The pathological studies of the respiratory tracts at d43 revealed viral infection with secondary complication in the lungs of the pigs.

TABLE 9

The number of experimental pigs with positive PRRSV in the lung at d 43

| Treatment | Positive animal/total examined (%[a]) |
|---|---|
| 1) Control (PBSA) | 3/6 (50) |
| 2) pORF7t-prime | 3/6 (50) |
| 3) Null plasmid | 5/6 (83.33) |

[a]% positive samples from 6 pigs/group

EXAMPLE 4

The Immunomodulatory Effects of PRRSV DNA Vaccine Delivered Using Transdermal Technology Inventors have observed the unexpected and surprising result that significantly improved efficacy was achieved when the inventive plasmids were delivered using transdermal technologies, specifically the DERMAVAC® device. In the above examples, the novel PRRSV-DNA vaccine was developed and tested for its immunoprophylaxis and immunotherapeutic properties against PRRSV. The results indicated that the prototype DNA vaccine, when intradermally immunized into the experimental pigs, was capable of modulating anti-PRRSV immune responses and enhanced viral clearance in the vaccinated-challenged pigs. Since intradermal injection technique was not routinely practiced in pig farms, the inventors explored the potential use of a needle-free device for delivering of the inventive DNA vaccine into pigs. It is contemplated by the inventors that inventive vaccines should additionally demonstrate efficacy in, for example, but not solely, fattening pigs and replacement gilts.

Materials and Methods.

Plasmid Immunization.

Figure 18:
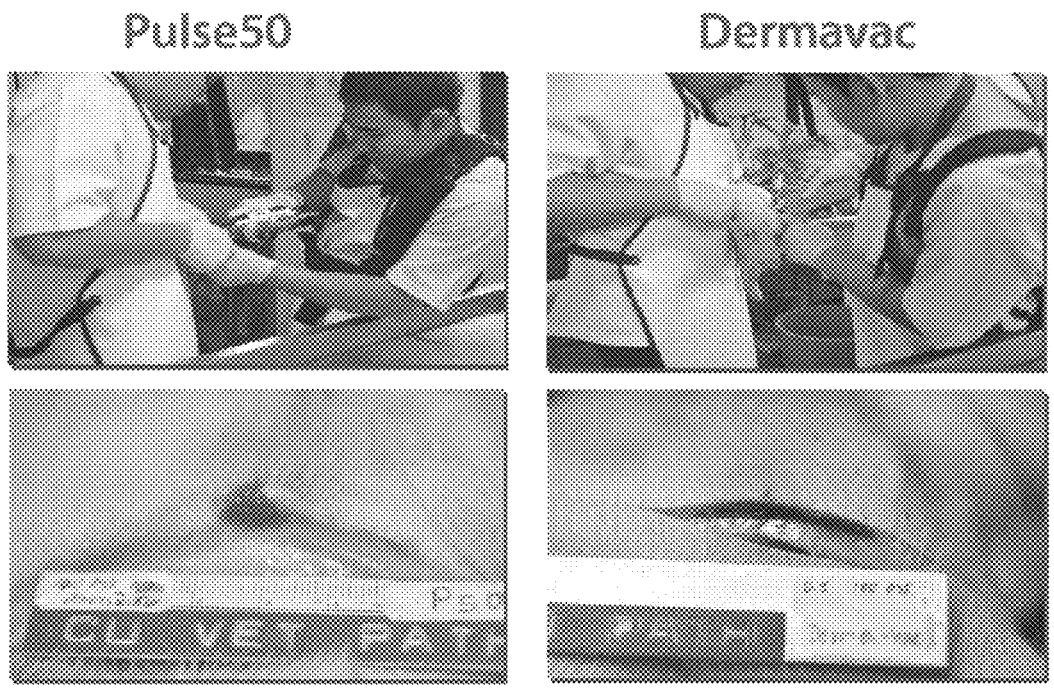
FIG. 18 are images of the needle-free injectors being used on the pigs.

The PRRSV-DNA vaccine (pORF7t) containing the genetically modified ORF7 gene, encoding for the linearized N protein, derived from the US-genotype, That PRRSV isolate (01 NP1), and null plasmid (pMASIA) were used for DNA immunization. The needleless injectors; Pulse50 (Pulse Needle-Free System, USA), and Dermavac (Merial, France) were tested and optimized for intradermal inoculation prior to the animal experiment (FIG. 18). Animal Experiment Four-week-old, crossbred pigs (8 pigs/group) were immunized with 200 µg or 500 µg of the indicated plasmid at day 0 (D0) using conventional intradermal injection, Dermavac or Pulse50 needleless injector. The immunological parameters were monitored every 2 weeks, at day 0, 14, 28, 42 and 56 post immunization. The pigs were kept at the commercial farm throughout the experiment. In vitro activation with PRRSV Freshly isolated porcine peripheral blood mononuclear cells (PBMCs) were cultured in vitro in the presence of the That isolated, US genotype, PRRSV (01 NP1 strain) or the control, MARC-145 infected cell lysate for 48 hours prior to harvesting and fluorescent labelings. The numbers of PRRSV-specific Treg, IL-10, and IFNγ producing cells in different lymphocyte subpopulation were determined by flow cytometry.

Results.

Figure 19:
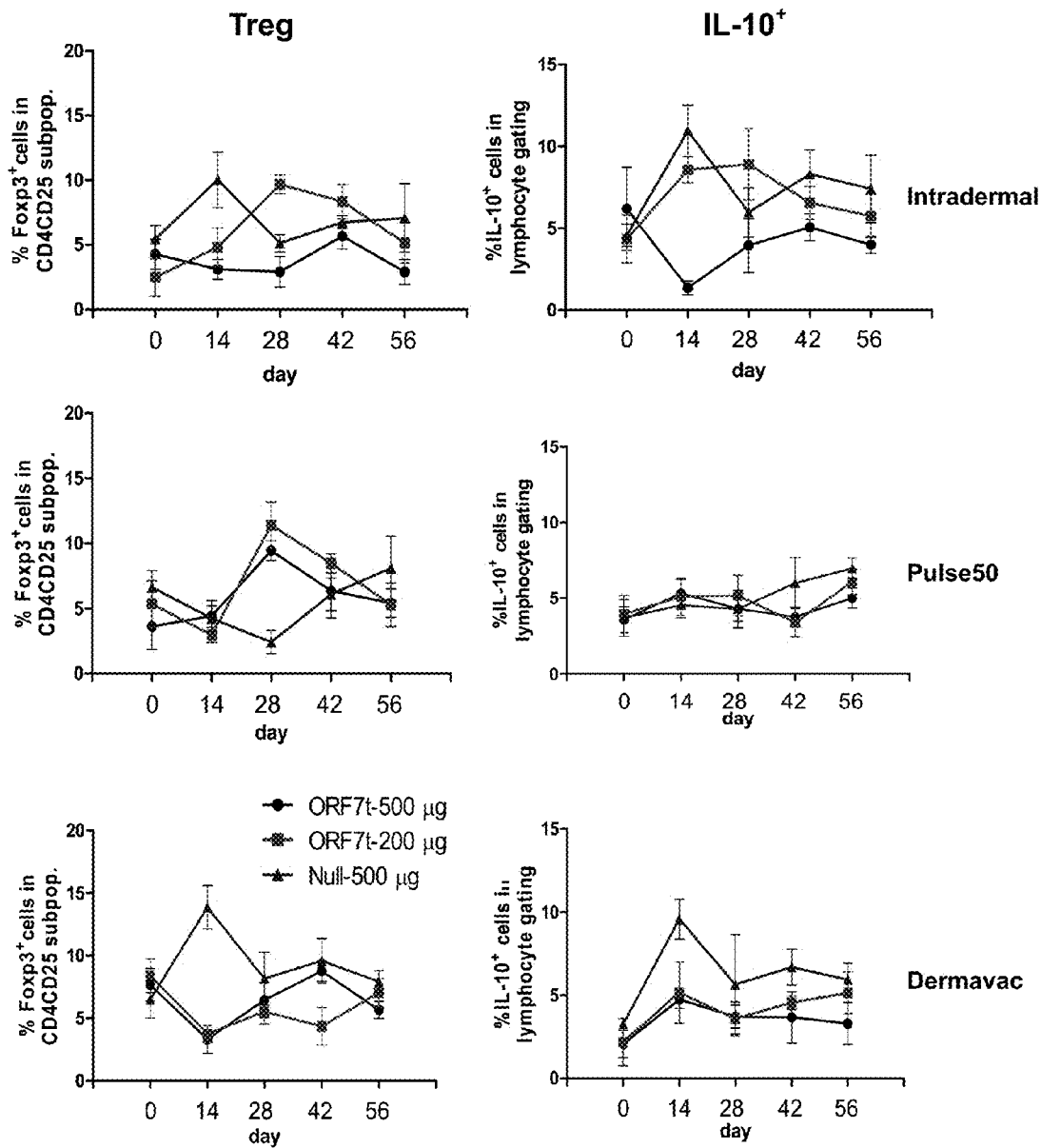
FIG. 19 are graphs depicting numbers of Treg and IL-10+ cells from lymphocyte subpopulations in PBMC, isolated from pigs immunized with ORF7t-500 µg, ORF7t-200 µg, or Null-500 µg via Intradermal, Pulse50, or Dermavac.
Figure 20:
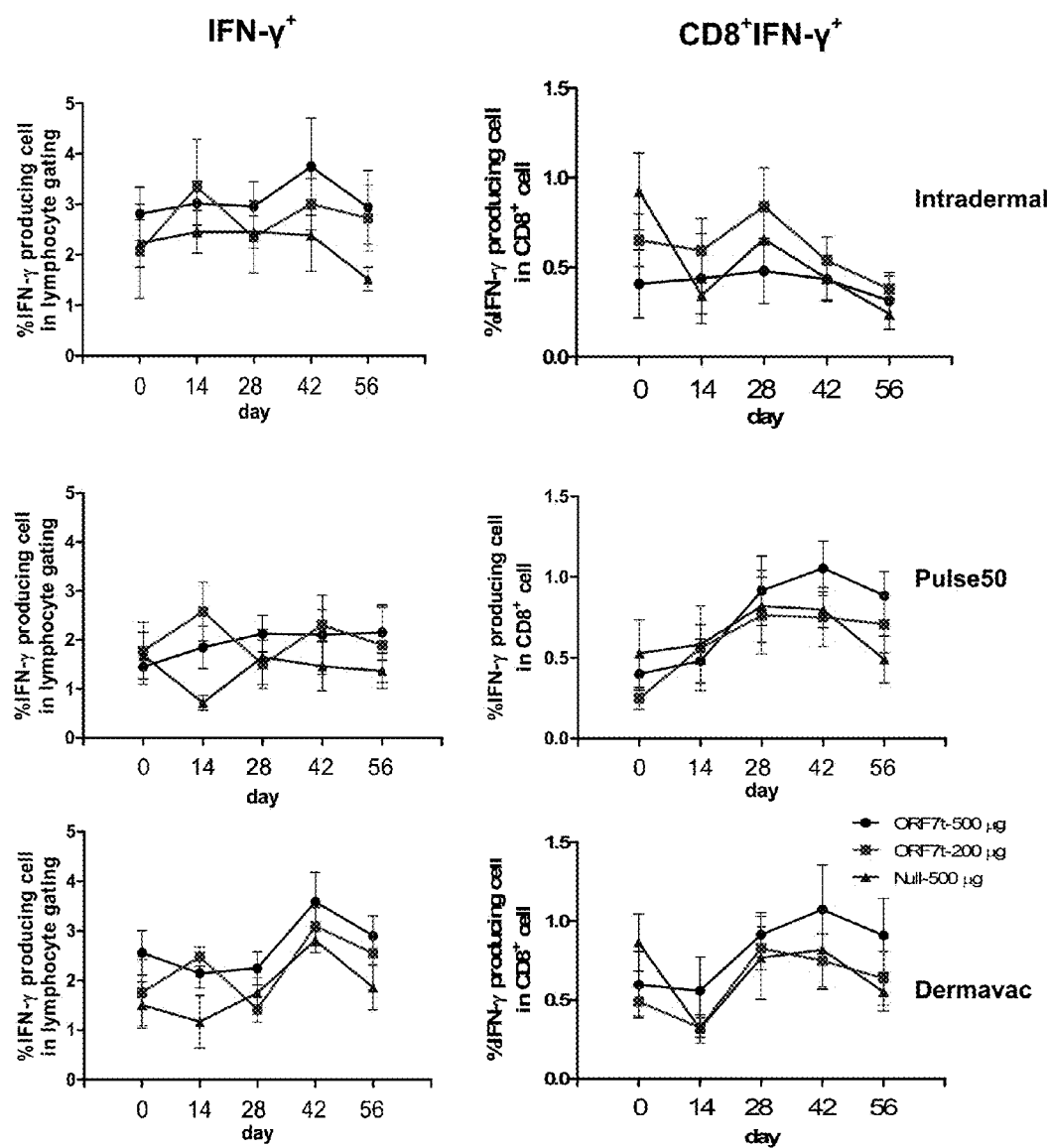
FIG. 20 are graphs depicting numbers of IFNγ+ and CD8+IFNγ+ cells from lymphocyte subpopulations in PBMC, isolated from pigs immunized with ORF7t-500 µg, ORF7t-200 µg, or Null-500 µg via Intradermal, Pulse50, or Dermavac.

Both needleless injectors provided effective DNA immunization in 4-week-old pigs. Following a single plasmid immunization (d0), the pig immunized with Dermavac exhibited significantly better patterns of controlled PRRSV-specific immunoinhibitory parameters (Treg and IL-10), and enhanced PRRSV-specific immunostimulatory parameters (IFNγ production), (FIG. 19). Interestingly, immunization with both injectors, at the dose of 500 µg, could enhance numbers of PRRSV-specific CD8+IFN-γ+ cells, compared to the conventional intradermal injection (FIG. 20).

EXAMPLE 5

PRRSV-DNA Vaccine Challenge Study (PRRSV-Positive Farm)

Objective.

This study was designed to evaluate the efficacy of the prototype DNA vaccine in the fattening pigs raised in PRRSV-positive farm Methods.

Four weeks old pigs from a commercial PRRSV-positive farm were randomly grouped (30 pigs/gr) and immunized twice, at 4 (d0) and 7 (d21) weeks old with DERMAVAC system. Pigs were moved to PRRSV-positive fattening site at 9 weeks old (d35). Group 1 was given PBSA (500 µl/dose); Group 2 received Null plasmid (pMASIA) at 500 µg/500 µl/dose); and Group 3 received the DNA vaccine (pORF7t) at 500 µg/500 µl/dose. Heparinized blood samples were collected (6 pigs/gr) for isolation of the PBMC and analysis of PRRSV-specific IL-10 and IFNγ producing cells and the numbers of PRRSV-specific CD4+CD25+Foxp3+ lymphocytes (Treg) on d0, 21, 35, 49, 84, 112, and 147. Serum samples were collected for determination of PRRSV-specific antibody (IDEXX ELISA) at the same time of whole blood collection. Monitoring of clinical signs and assessing lung score were performed at the slaughter house.

Results.

Figure 22:
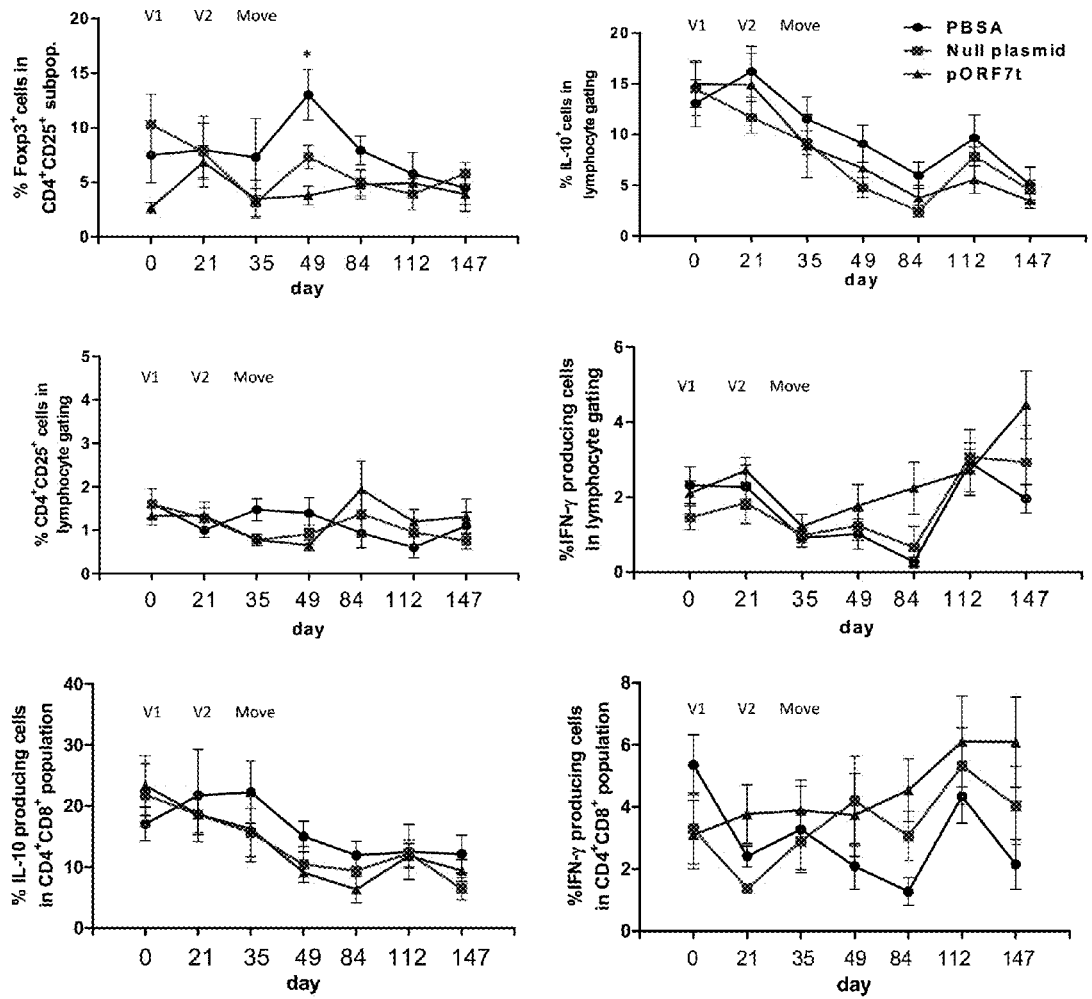
FIG. 22 Numbers of PRRSV-specific CD4+CD25+ FoxP3+ cells (A), IL-10+ cells (B), CD4+CD25+ cells (C) and IFNγ+ cells (D) in a lymphocyte gate, numbers of PRRSV-specific IL-10+ (E), IFNγ+ (F) cells in the CD4+CD8+ lymphocyte subpopulation from pigs raised in the PRRSV-positive production system. Pigs were immunized with PBSA, null plasmid, or pORF7t on d0 (V1) and d21 (V2), and then moved to the fattening site on d35 (Move). The PBMCs were cultured with PRRSV (01NP1) or mock lysate for 48 hr prior to flow cytometric analysis. The data are mean±SEM of the % PRRSV-activated lymphocyte subpopulations, subtracted with background obtained from the cells cultured with MARC-145 lysate. * indicates statistical difference between the DNA vaccinated group and the control groups (p<0.05, one-way ANOVA followed by Tukey multiple comparison test)

No vaccine adverse reaction was observed following DNA immunization. The pigs receiving DNA vaccine tended to have lower numbers of PRRSV-specific CD4+CD25+Foxp3+ Treg than the control groups, particularly after moving to the fattening site. The increases in Treg numbers were observed in both control groups following moving (d49), but not in the DNA vaccinated group (FIG. 22A). There were not statistical differences in the numbers of IL-10 producing cells throughout the experiment.

There was an increase in the numbers of PRRSV-specific CD4+CD25+ lymphocyte (activated effector T cells) in the DNA vaccinated group following moving, (FIG. 22C), consistent with an increase in the numbers of PRRSV-specific IFNγ producing cells. The number of PRRSV-specific IFN-γ producing cells in DNA vaccinated group was significantly higher than the control groups on d84 (FIG. 22D). The number of IFNγ producing memory T cells (CD4+CD8+IFN-γ+ cells) of the DNA vaccinated group remained at a higher level, compared to the controls, through the end of the observatory period (FIG. 22F). It should be noted that the data variation within the study groups was quite high in this experiment. In addition, the immunomodulatory effects of the null plasmid were also observed.

Figure 23:
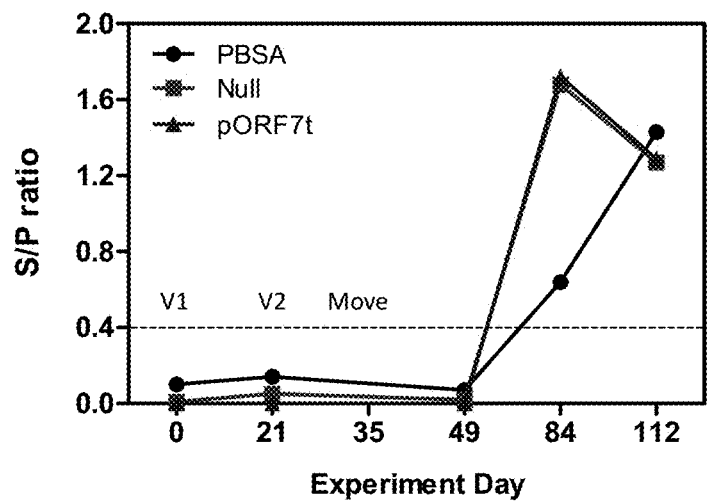
FIG. 23 is a graph showing S/P ratio among control and pORF7t vaccinated pigs.
Figure 24:
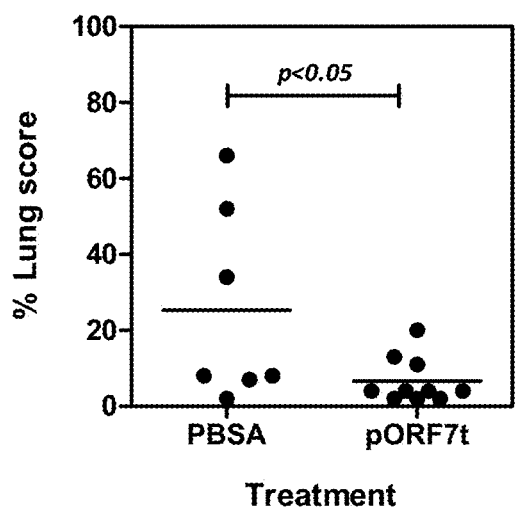
FIG. 24 is a graph of lung scores obtained from the experimental pigs.

On day 84, all groups exhibited PRRSV-seroconversion following moving into the PRRSV-positive fattening site. On dl 12, all pigs were seroconverted with the similar pattern of S/P ratios (FIG. 23). There was no significant difference in clinical sign among the groups during fattening period. Interestingly, the group receiving DNA vaccine exhibited lower lung scores, than the control group (p<0.05, student t-test), (FIG. 24).

Summary.

The DNA vaccine modulated the PRRSV-specific immune responses as shown by enhanced immunostimulatory parameters and reduced immunoinhibitory parameters during the fattening period (Table 10). There were no significant differences in the patterns of anti-PRRSV humoral responses among the experimental groups. In addition, the DNA vaccination pigs exhibited significantly lower lung pathological changes than the control pigs.

TABLE 10

Summary for % seropositive animals

| | % seropositive* (No. of positive/tested animals) | | | | |
|---|---|---|---|---|---|
| Group | d 0 | d 21 | d 49 | d 84 | d 112 |
| PBSA | 0 (0/7) | 0 (0/7) | 0 (0/7) | 57.14 (4/7) | 100 (8/8) |
| Null | 0 (0/7) | 0 (0/7) | 0 (0/7) | 100 (6/6) | 100 (7/7) |
| pORF7t | 0 (0/7) | 0 (0/7) | 0 (0/7) | 100 (6/6) | 100 (8/8) |

*S/P ratio > 0.4

EXAMPLE 6

PRRSV-DNA Vaccine Challenge Study (PRRSV-Negative Farm)

Methods.

Four week-old pigs in a PRRSV-seronegative commercial farm were randomly grouped (30 pigs/gr) and vaccinated at 4 weeks (d0) and 7 weeks old (d21), using Dermavac system. The pigs were all moved to the PRRSV-negative fattening site at approximately 9 weeks old. The treatment groups were as follows: Gr. 1 (PBSA, 500 µl/dose); Gr. 2 (Null plasmid, 500 µg/500 µl/dose); and Gr. 3 (pORF7t DNA vaccine 500 µg/500 µl/dose). Heparinized blood samples were collected (6 pigs/gr) for isolation of the PBMC and analysis of PRRSV-specific IL-10 and IFNγ producing cells and the numbers of PRRSV-specific CD4$^+$CD25$^+$ Foxp3$^+$ lymphocytes (Treg) on d0, 21, 35, 49, and 63. Serum samples were collected for determination of PRRSV-specific antibody (IDEXX ELISA) at the same time of whole blood collection.

Results.

Figure 25:
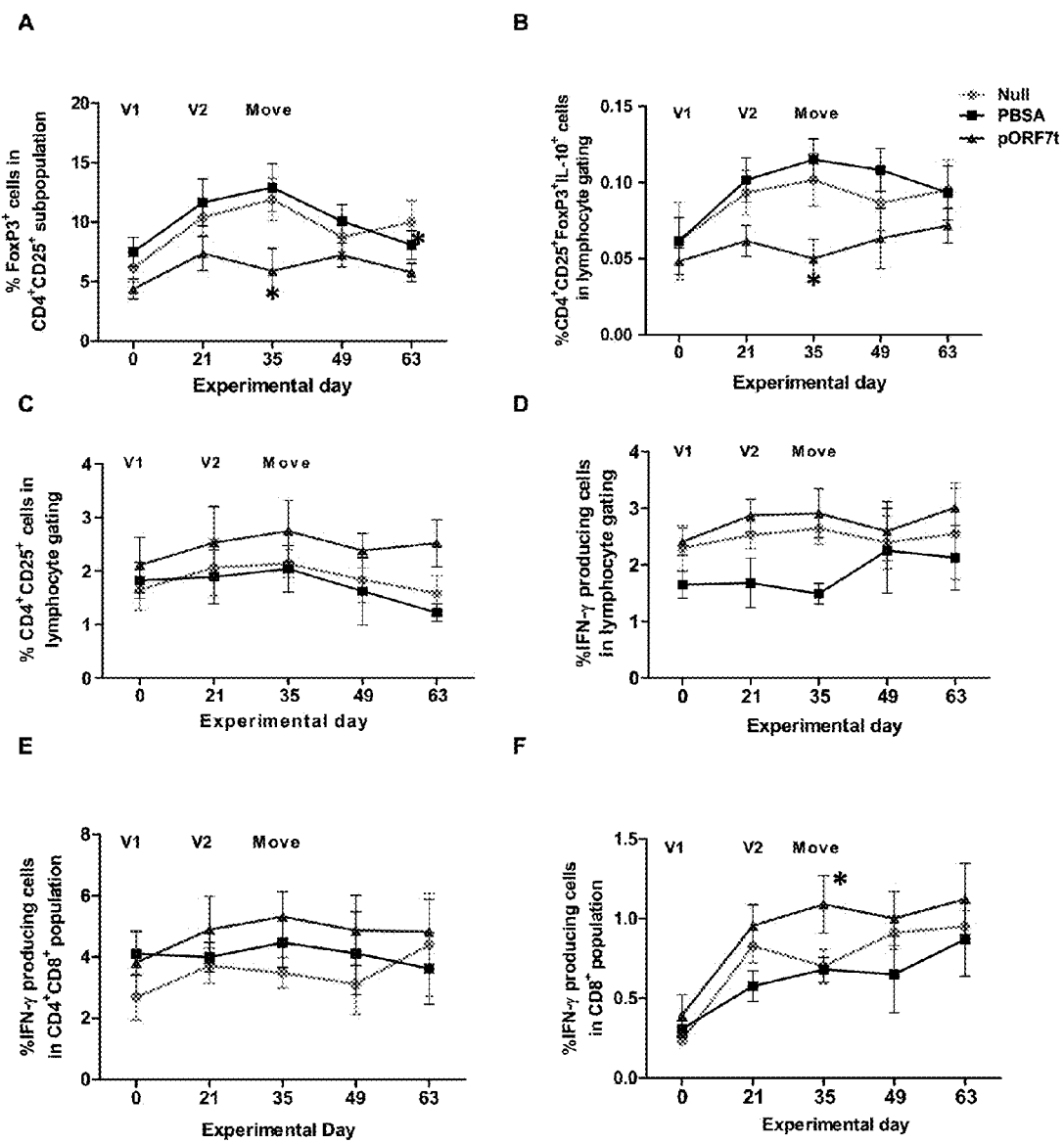
FIG. 25 are graphs indicating numbers of PRRSV-specific CD4+CD25+FoxP3+ cells (A), CD4+CD25+FoxP3+IL-10+ cells (B), CD4+CD25+ cells (C) and IFNγ+ cells (D) in a lymphocyte gate, numbers of PRRSV-specific IFNγ+ cells in CD4+CD8+(E) CD8+ subpopulation from pigs raised in a PRRSV-negative production system—** indicates statistical difference between the DNA vaccinated group and the control groups (p<0.05, one-way ANOVA followed by Tukey multiple comparison)
Figure 26A:
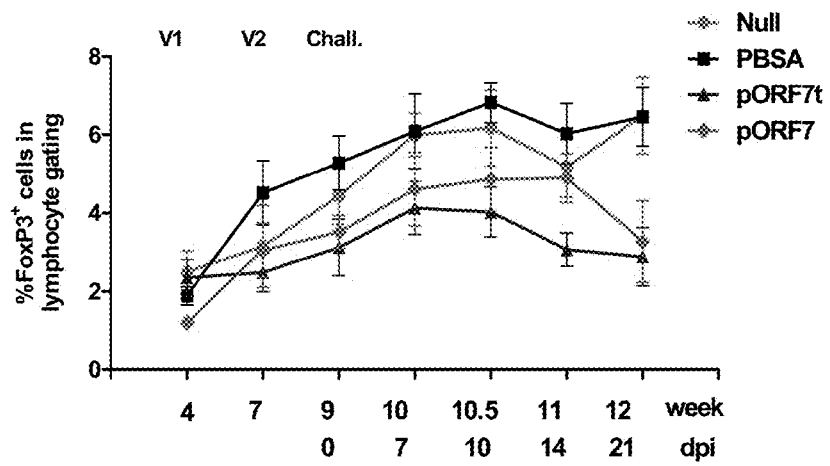
FIG. 26A is a graph showing numbers of FoxP3$^+$ cells from challenged pigs; Pigs were vaccinated with PBSA, null plasmid, or pORF7t on d0 (V1) and d21 (V2), and challenged (Chall.) on d35. The data are mean±SEM of the % PRRSV-activated lymphocyte subpopulations, subtracted with background obtained from the cells cultured with MARC-145 lysate. Mean differences were considered significant if p<0.05, using one-way ANOVA followed by Tukey multiple comparison test (for FIG. 22A, pORF7t and PBSA means were significantly different).
Figure 26B:
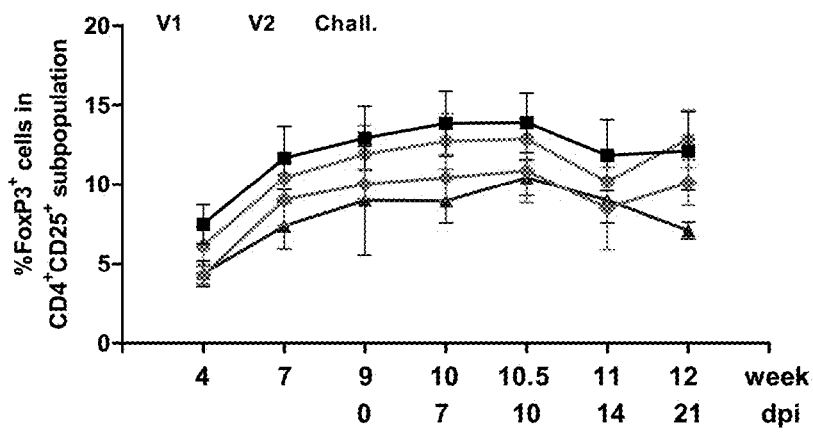
FIG. 26B is a graph showing numbers of CD4$^+$CD25$^+$ FoxP3$^+$ cells from challenged pigs (pORF7t differed significantly from either null plasmid (pMASIA) or PBSA immunized group)
Figure 26C:
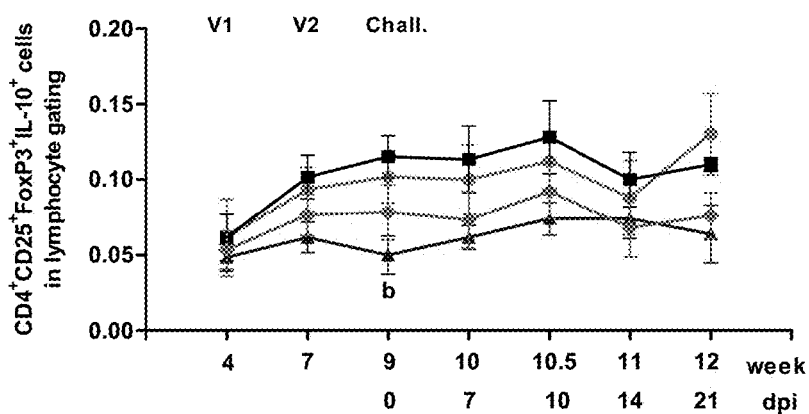
FIG. 26C is a graph showing numbers of CD4$^+$CD25$^+$ FoxP3$^+$IL-10$^+$ cells form challenged pigs (pORF7t and null plasmid differed significantly)
Figure 26D:
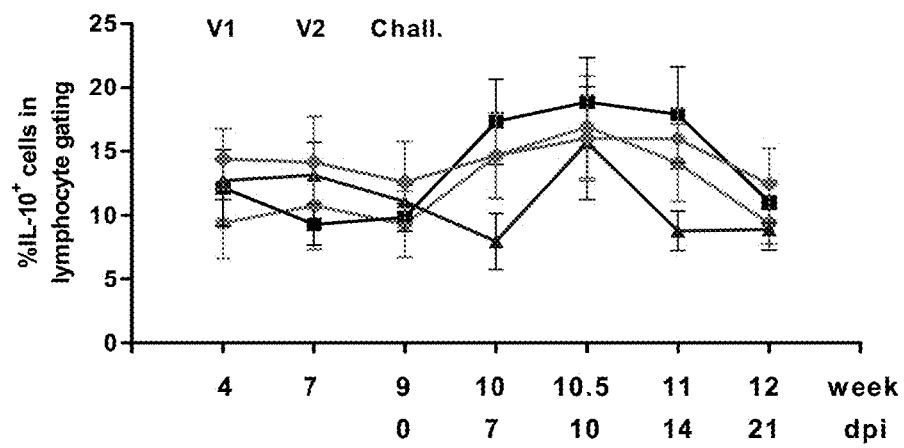
FIG. 26D is a graph showing IL-10$^+$ cells in a lymphocyte gate from challenged pigs.
Figure 27A:
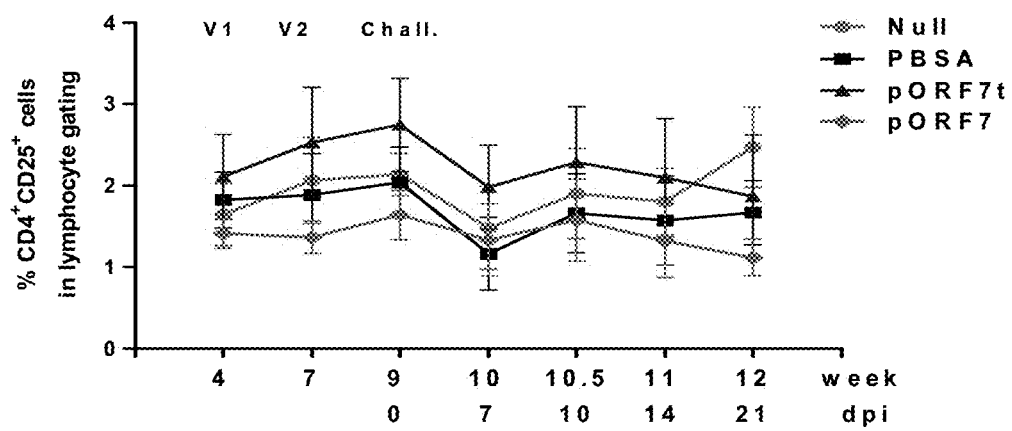
FIG. 27A is a graph showing % CD4$^+$CD25$^+$ cells in a lymphocyte gate; Pigs were vaccinated with PBSA, null plasmid, or pORF7t on d0 (V1) and d21 (V2), and challenged (Chall.) on d35. The data are mean±SEM of the % PRRSV-activated lymphocyte subpopulations, subtracted with background obtained from the cells cultured with MARC-145 lysate.
Figure 27B:
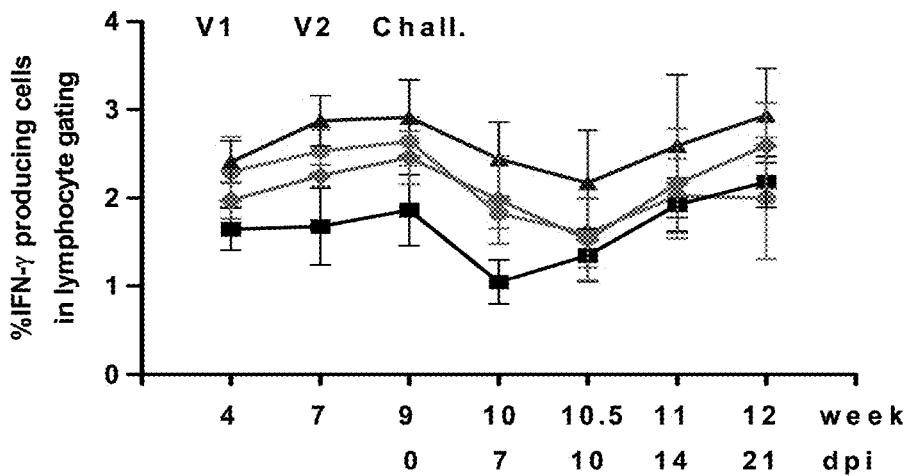
FIG. 27B is a graph showing % IFNγ producing cells in a lymphocyte gate.
Figure 27C:
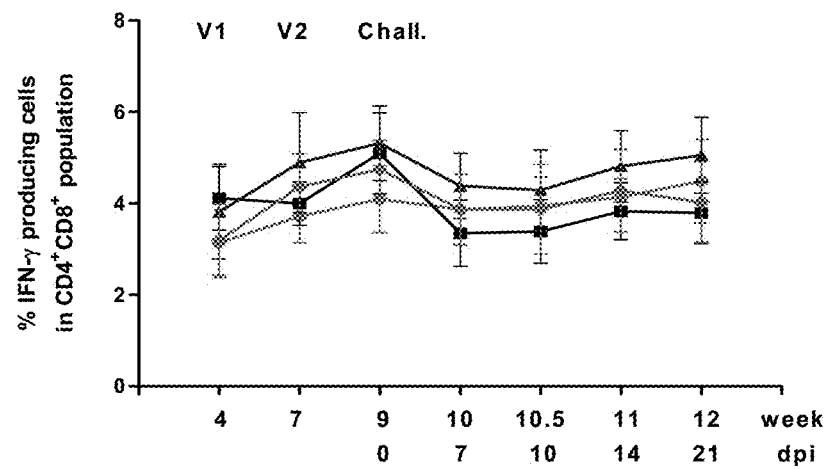
FIG. 27C is a graph showing % IFNγ producing cells in CD4$^+$CD8$^+$ population.
Figure 27D:
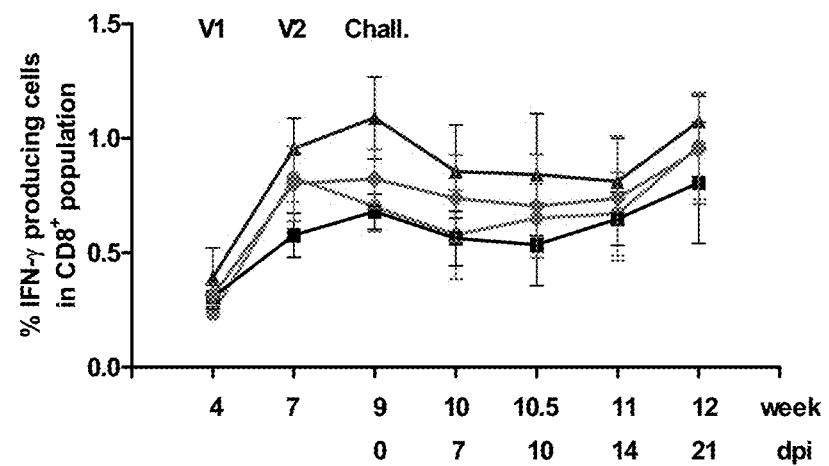
FIG. 27D is a graph showing % IFNγ producing cells in CD8$^+$ population.
Figure 28A:
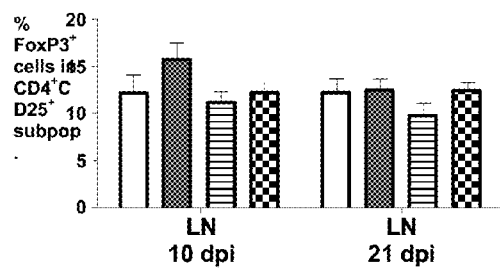
FIG. 28A is a graph showing the levels of viral load in the serum samples; pigs were vaccinated with PBSA, null plasmid, pORF7, or pORF7t on d0 and d21, and challenged with US-PRRSV (strain 01NP1) on d35 (0 dpi). Serum, lung, and tracheobronchial lymph node samples were collected at the indicated days, and subjected for determination of the quantity of PRRSV genome by quantitative RT-PCR (as described by Egli et al., 2001. J. Virol. Methods. 98: 63-75)
Figure 28B:
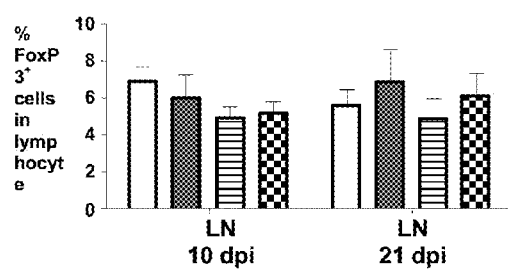
FIG. 28B is a graph showing the levels of viral load in the lungs.
Figure 28C:
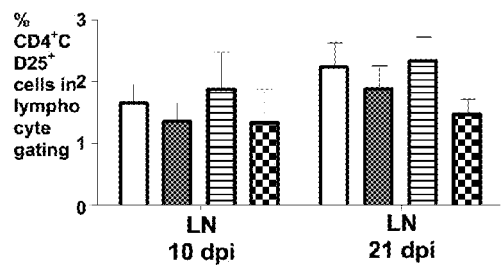
FIG. 28C is a graph showing the level of virus in tracheobronchial lymph nodes.
Figure 28D:
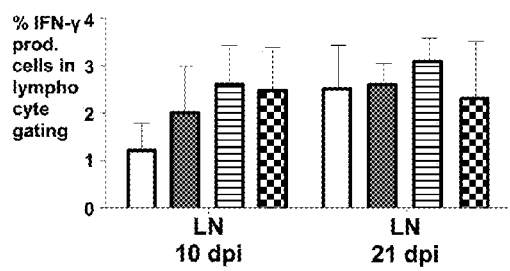
Figure 28E:
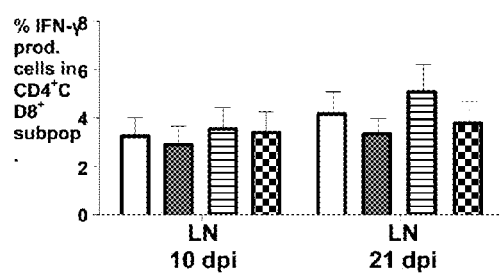
Figure 28F:
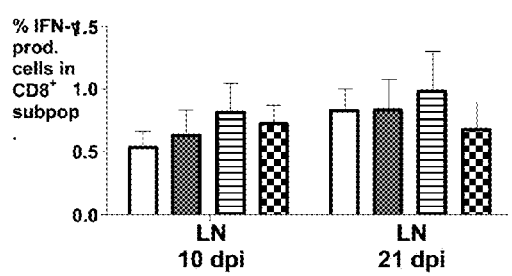

No vaccine adverse reaction was observed throughout the experiment. The immunomodulatory effects of the prototype DNA vaccine were depicted in FIG. 25. Following the second vaccination, the group vaccinated with pORF7t exhibited significantly lower immunoinhibitory parameters than the control groups, and the numbers of PRRSV-specific CD4$^+$CD25$^+$Foxp3$^+$ and CD4$^+$CD25$^+$Foxp3$^+$IL-10$^+$ lymphocytes were lower than the control groups throughout the experiment, especially at day 35 (FIGS. 25A & 25B). In addition, the DNA immunized group tended to have higher numbers of immunostimulatory parameters than the control groups. There were quite high data variations within the experimental groups. However, the group receiving DNA vaccine had significantly higher numbers of PRRSV-specific CD8$^+$IFNγ$^+$ lymphocytes (CTL) than the control groups at d35 (FIG. 25F). In addition, the immunomodulatory effects of the null plasmid were also observed in this study. No seroconverion was observed in the pigs throughout the experiment, and there was no obvious difference in the clinical signs among the groups. In summary, the immunized pigs exhibited significantly better PRRSV-specific cell-mediated immune responses and lower immunoinhibitory parameters, with no evidence of enhance anti-PRRSV antibody response.

EXAMPLE 7

Challenge Study (PRRSV-Seronegative Farm)

Methods.

Four week old pigs in a PRRSV-seronegative farm were randomly grouped (10-12 pigs/gr) and vaccinated at 4 weeks (d0) and 7 weeks old (d21), using Dermavac: Gr. 1 (PBSA, 500 μl/dose); Gr. 2 (Null plasmid, 500 μg/500 μl/dose); Gr. 3 (pORF7t, 500 μg/500 μl/dose); and Gr. 4 (pORF7, 500 μg/500 μl/dose). Prior to the age of 9 weeks old, pigs were moved to the isolation unit, and following acclimatization, the pigs were intranasally challenged with 5 ml (2.5 ml/nostril) of $10^{5.5}$ TCID$_{50}$/ml of the virulent, US genotype PRRSV (strain 01NP1). The clinical signs were monitored following the challenge until the end of the experiment. Pigs (5-6 pigs/gr) were euthanized at 10 days post infection (dpi) and 21 dpi, and subjected for virological and pathological studies. Heparinized blood samples were collected (5 pigs/gr) for isolation of the PBMC and analysis of PRRSV-specific IL-10 and IFNγ producing cells and the numbers of PRRSV-specific CD4$^+$CD25$^+$Foxp3$^+$ lymphocytes (Treg) on the vaccination days (d0, d21) and at 0, 7, 14, and 21 dpi.

Results.

The pORF7t vaccinated group exhibited significantly lower number of the PRRSV-specific Treg, while there were increases in the numbers of the Foxp3$^+$ cells in the control groups throughout the observatory period (FIG. 26). On the challenge day (0 dpi), the numbers of Foxp3$^+$ lymphocytes from the DNA vaccinated group were lower than those of the controls (FIG. 26B-C). Following the challenge the numbers of Foxp3$^+$ cells in the pORF7t vaccinated group remained lower than the control groups throughout the experiment. At the end of the observatory period (21 dpi), the pORF7t vaccinated group had significant lower Treg number than the control groups (FIG. 26A-C). Following the challenge, there were increases in the numbers of IL-10 producing cells in every experimental group. However, the pORF7t vaccinated group exhibited slower increase and faster reduction in the number of IL-10 producing cells (FIG. 26D). The pORF7t vaccinated group tended to have higher immunostimulatory parameters than the control groups. All challenge pigs exhibited clinical signs of PRRSV infection including depression in appetite, fever, swollen eyes, coughing. The pORF7t Group animals exhibited fewer clinical signs, and responded to external stimuli better than the other groups.

Figure 29A:
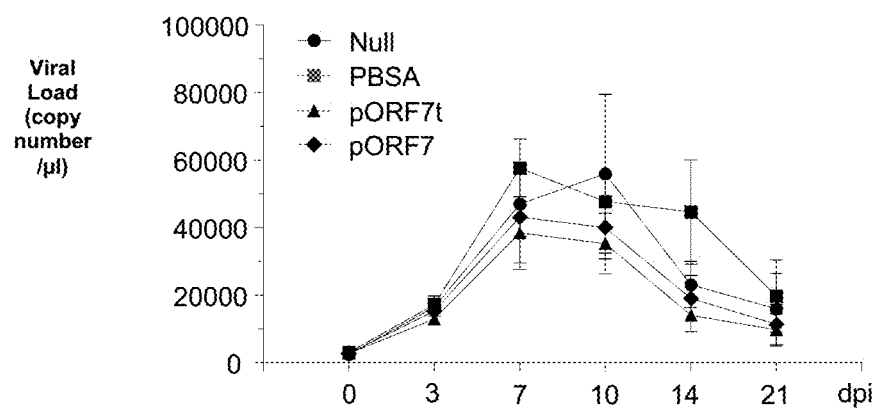
FIG. 29A is a graph of viral load following vaccination.
Figure 29B:
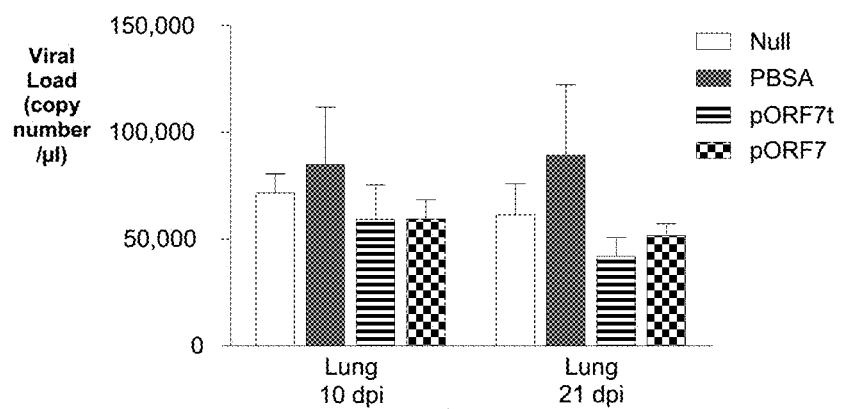
FIG. 29B is a graph of viral load in lung at 10 and 21 dpi.
Figure 29C:
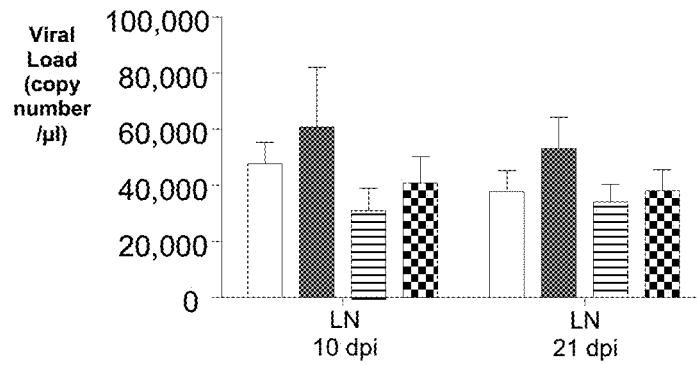
FIG. 29C is a graph of viral load in lymph node at 10 and 21 dpi.

Following the challenge, PRRSV was detected from 3 dpi, peaked at 7-10 dpi and gradually decreased till the end of the experiment (FIG. 29). The pORF7t vaccinated group was less viremic and recovered faster than the control groups (FIG. 29A). There was a trend of lower levels of viral genome in the lungs and tracheobronchial lymph nodes of the DNA vaccinated pigs (FIG. 29B). However, due to high data variation within the group, there was no statistical difference among the experimental groups. PRRSV seroconversion could be detected 2 weeks following the challenge. There were more seroconverted animals in the pORF7t vaccinated group at 21 dpi, however, no significant difference in the levels of S/P ratio was observed among the group. In addition, no PRRSV-specific neutralizing antibody was detected in any group, at 21 dpi.

Pathological studies at 10 dpi revealed the PRRSV induced pathological changes in the lungs from all groups (Table 12). There were more degree of macroscopic pathological changes in the lungs and lymph nodes of the control groups. At 21 dpi, the observed pathological changes were comparable among the groups (Table 13).

Summary.

This study demonstrated that the prototype PRRSV-DNA vaccine could modulate the PRRSV-specific immune responses in the vaccinated-challenged pigs as expected. The reduced number of Treg and enhanced immunostimulatory parameters were observed in the DNA vaccinated group, in particular, following the challenge. At 10 dpi, the pORF7t vaccinated pigs were less viremic, exhibited better clinical signs and less pathological changes than the control groups.

TABLE 11

Percent Seropositive

| Group | % seropositive* (No. of positive/tested animals) | | | |
|---|---|---|---|---|
| | 0 dpi | 7 dpi | 14 dpi | 21 dpi |
| PBSA | 0 (0/5) | 0 (0/5) | 0 (0/5) | 40 (2/5) |
| Null | 0 (0/5) | 0 (0/5) | 0 (0/5) | 0 (0/5) |
| pORF7t | 0 (0/5) | 0 (0/5) | 20 (1/5) | 60 (3/5) |

*positive: S/P ratio > 0.4

TABLE 12

Pathological findings in vaccinated-challenged pigs at 10 dpi
Macroscopic findings

| Pig No | Treatment group | Necropsy date (DPI) | Lung Score | Pleuritis | Remarks |
|---|---|---|---|---|---|
| A1 | Null | 10 | 0 | Neg | — |
| A6 | Null | 10 | 1% | Neg | cranioventral pneumonia |
| A20 | Null | 10 | 0 | Neg | superficial inguinal lymph node enlargement 1.5 times |
| A29 | Null | 10 | 3% | Neg | cranioventral pneumonia |
| A30 | Null | 10 | 0 | Neg | — |
| A40 | Null | 10 | 0 | Neg | — |
| B17 | PBSA | 10 | 0 | Neg | interstitial pneumonia and subcapsular hemorrhage at mediasternal lymph node |
| B30 | PBSA | 10 | 0 | Neg | interstitial pneumonia and superficial inguinal lymph node enlargement 1.5 times |
| B35 | PBSA | 10 | 0 | Neg | — |
| B37 | PBSA | 10 | 0 | Neg | mild Interstitial pneumonia and superficial inguinal lymph node enlargement and edema |
| B39 | PBSA | 10 | 14% | Neg | cranioventral pneumonia and superficial inguinal lymph node enlargement 1.5 times |
| D8 | pORF7t | 10 | 0 | Neg | — |
| D17 | pORF7t | 10 | 0 | Neg | superficial inguinal lymph node enlargement 2 times |
| D21 | pORF7t | 10 | 0 | Neg | — |
| D24 | pORF7t | 10 | 0 | Neg | — |
| D34 | pORF7t | 10 | 0 | Neg | — |

| Pig No. | Treatment group | Necropsy date (DPI) | M. hyo lesion | PRRSV lesion | Pathological Dx |
|---|---|---|---|---|---|
| A1 | Null | 10 | 1 | 1 | mild multifocal bronchointerstitial pneumonia |
| A6 | Null | 10 | 1 | 1 | mild multifocal bronchointerstitial pneumonia |
| A20 | Null | 10 | 1 | 1 | mild multifocal bronchointerstitial pneumonia |
| A29 | Null | 10 | 0 | 2 | mild multifocal interstitial pneumonia |
| A30 | Null | 10 | 1 | 1 | mild interstitial pneumonia with mild congestion |
| A40 | Null | 10 | 1 | 1 | mild multifocal bronchointerstitial pneumonia |
| B17 | PBSA | 10 | 1 | 1 | mild multifocal bronchointerstitial pneumonia |
| B35 | PBSA | 10 | 1 | 1 | mild interstitial pneumonia |
| B37 | PBSA | 10 | 1 | 1 | mild multifocal bronchointerstitial pneumonia |
| B39 | PBSA | 10 | 2 | 2 | moderate multifocal bronchointerstitial pneumonia |
| D8 | pORF7t | 10 | 1 | 2 | moderate diffuse interstitial pneumonia |
| D17 | pORF7t | 10 | 1 | 2 | moderate multifocal bronchointerstitial pneumonia |
| D21 | pORF7t | 10 | 0 | 1 | mild multifocal interstitial pneumonia |
| D24 | pORF7t | 10 | 1 | 2 | moderate diffuse interstitial pneumonia |
| D34 | pORF7t | 10 | 1 | 2 | moderate multifocal bronchointerstitial pneumonia |

PRRS lesion score
0: no lesion
1: mild interstitial pneumonia
2: moderate multifocal interstitial pneumonia
3: severe multifocal interstitial pneumonia
M hyo lesion score
0: no lesion
1: mild degree
2: moderate degree
3: severe degree

TABLE 13

Pathological findings in vaccinated-challenged pigs at 21 dpi
Microscopic findings (no macroscopic signs noted)

| Pig No. | Treatment group | Necropsy date (DPI) | M hyo lesion | PRRSV lesion | Pathological Dx |
|---|---|---|---|---|---|
| A9 | Null | 21 | 1 | 2 | moderate multifocal bronchointerstitial pneumonia |
| A18 | Null | 21 | 1 | 2 | mild multifocal bronchointerstitial pneumonia |
| A19 | Null | 21 | 1 | 2 | moderate multifocal bronchointerstitial pneumonia |
| A22 | Null | 21 | 3 | 2 | severe multifocal bronchointerstitial pneumonia |
| A36 | Null | 21 | 1 | 2 | moderate multifocal bronchointerstitial pneumonia |
| B1 | PBSA | 21 | 1 | 2 | moderate multifocal bronchointerstitial pneumonia |
| B6 | PBSA | 21 | 1 | 2 | mild multifocal bronchointerstitial pneumonia |
| B13 | PBSA | 21 | 1 | 2 | moderate multifocal bronchointerstitial pneumonia |
| B15 | PBSA | 21 | 1 | 1 | mild multifocal bronchointerstitial pneumonia |

TABLE 13-continued

Pathological findings in vaccinated-challenged pigs at 21 dpi
Microscopic findings (no macroscopic signs noted)

| Pig No. | Treatment group | Necropsy date (DPI) | M hyo lesion | PRRSV lesion | Pathological Dx |
|---|---|---|---|---|---|
| B23 | PBSA | 21 | 1 | 2 | moderate multifocal bronchointerstitial pneumonia |
| D4 | pORF7t | 21 | 2 | 2 | moderate multifocal bronchointerstitial pneumonia |
| D16 | pORF7t | 21 | 2 | 1 | moderate multifocal bronchointerstitial pneumonia |
| D28 | pORF7t | 21 | 1 | 1 | mild multifocal bronchointerstitial pneumonia |
| D36 | pORF7t | 21 | 2 | 2 | moderate multifocal bronchointerstitial pneumonia |
| D37 | pORF7t | 21 | 1 | 2 | moderate multifocal bronchointerstitial pneumonia |

PRRS lesion score
0: no lesion
1: mild interstitial pneumonia
2: moderate multifocal interstitial pneumonia
3: severe multifocal interstitial pneumonia
M hyo lesion score
0: no lesion
1: mild degree
2: moderate degree
3: severe degree

EXAMPLE 8

Vaccine Efficacy in Replacement Gilts in the PRRSV-Positive Farm

Methods.

Nineteen week old, replacement gilts from a PRRSV-negative commercial farm were randomly grouped (30 pigs/gr) and immunized twice, at 20 (d0) and 23 (d21) weeks old with Dermavac system. Pigs were moved to PRRSV-positive production site at 9 weeks old (d35). The immunization groups were as followed; Gr. 1 PBSA (500 µl/dose); Gr. 2 Null plasmid (pMASIA, 500 µg/500 µl/dose); Gr. 3 DNA vaccine (pORF7t, 500 µg/500 µl/dose. At 25 weeks old, the gilts were moved to PRRSV-positive farm where they would be exposed to the local PRRSV strain during the acclimatization in the recipient farm. The recipient farm has low level of losses from PRDC and PRRSV. Heparinized blood samples were collected (6 pigs/gr) for isolation of the PBMC and analysis of PRRSV-specific IL-10 and IFNγ producing cells and the numbers of PRRSV-specific CD4$^+$CD25$^+$Foxp3$^+$ lymphocytes (Treg) on d0, 21, 35, 42, 49, 56, 70, and 98. Methods were generally performed as in previous example.

Results.

No evidence of vaccine adverse reaction was observed in the vaccinated gilts. Following vaccination, the vaccinated gilts exhibited a tendency of reduced PRRSV-specific CD4$^+$CD25$^+$Foxp3$^+$ Treg and IL-10 producing cells, and enhanced PRRSV-specific memory effector T cells and IFNγ producing cells, compared to the controls throughout the experiment. The DNA-vaccinated gilts contained significantly lower numbers of PRRSV-specific CD4$^+$CD25$^+$Foxp3$^+$ lymphocyte (Treg), and higher numbers of PRRSV-specific IFNγ producing cells than the pigs received PBSA on the day they were moved to the positive production site. It should be noted that there was quite high data variation within the experimental groups.

Prior to moving, the baseline levels of PRRSV genome in all groups were comparable, but following the move, PRRSV infection became apparent in all groups, as indicated by increases in PRRSV viral loads in the serum. The viremic stages were observed from 3 days post moving (dpm), peaked around 10-14 dpm, and lasted approximately 2 weeks. The pORF7t vaccinated gilts tended to have slower increases in viral loads and lower copy numbers of detected PRRSV genome in their serum samples.

Summary.

The pORF7t DNA vaccine exhibited immunomodulatory activities as in previous studies. Following PRRSV exposure in the farm, there was a trend of lower level of PRRSV viremia, and less culling in the DNA vaccinated gilts, as compared to controls.

TABLE 14

Reproductive performances of the experimental replacement gilts

| Group | Gilt No. | Mating batch | Number of piglets | | | | | |
|---|---|---|---|---|---|---|---|---|
| | | | Born | Dead | Mummified | Congenital anomaly | Weak | Crushed by sow | Alive |
| PBSA | | | | | | | | | 78 |
| 1 | 5056 | M 16 | 13 | | | | | | 13 |
| 2 | 5363 | M 21 | 20 | | | | | | 20 |
| 3 | 5312 | M 15 | 14 | | 1 | | | | 13 |
| 4 | 5220 | M 17 | 13 | 1 | | | | | 12 |
| 5 | 4951 | M 16 | 10 | | | | | | 10 |
| 6 | 5273 | Culled 10/4 | | | | | | | |
| 7 | 5245 | M 17 | 10 | | | | | | 10 |
| Null | | | | | | | | | 38 |
| 1 | 5071 | Culled 20/8 | | | | | | | |
| 2 | 5293 | M26 | in gestation* | | | | | | |

TABLE 14-continued

Reproductive performances of the experimental replacement gilts

| Group | Gilt No. | Mating batch | Number of piglets Born | Dead | Mummified | Congenital anomaly | Weak | Crushed by sow | Alive |
|---|---|---|---|---|---|---|---|---|---|
| 3 | 5054 | M17 | 15 | 1 | | | | 2 | 12 |
| 4 | 5248 | M12 | 9 | | | | | | 9 |
| 5 | 5083 | Culled 3/7 | | | | | | | |
| 6 | 5131 | M 18 | 5 | | | | | | 5 |
| 7 | 4987 | M 12 | 12 | | | | | | 12 |
| pORF7t | | | | | | | | | 64 |
| 1 | 5077 | M18 | 16 | | 7 | | | | 9 |
| 2 | 5159 | M18 | 7 | | | | | | 7 |
| 3 | 4978 | M22 | 11 | | | | | | 11 |
| 4 | 5152 | M18 | 14 | | | | | | 14 |
| 5 | 5062 | M18 | 12 | | | | | | 12 |
| 6 | 4952 | M12 | 12 | 1 | | | | | 11 |
| 7 | 5368 | Dead 7/1 (during acclimatization) | | | | | | | |

*at the end of observation period. This gilt required more than two mating cycles to be productive.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of eliciting in a suidae animal a protective immune response against porcine reproductive and respiratory syndrome virus (PRRSV), said method consisting of transdermally administering to the suidae animal as a weaner by liquid jet needle-free injector a single dose of a vaccine; said vaccine comprising an effective amount of a non-viral DNA plasmid vector; said non-viral DNA plasmid vector encoding, and when so administered there is expression in vivo in the suidae animal of, a single truncated PRRSV ORF7 protein, consisting of the sequence as set forth in SEQ ID NO: 4 in an effective amount to provide the suidae animal protection from subsequent challenge with a virulent PRRSV, thereby eliciting the protective immune response.

2. The method of claim 1, wherein the vaccine further comprises the adjuvant TS6, administered with the non-viral DNA plasmid vector.

3. The method of claim 1 or 2, wherein the weaner suidae animal is a weaned piglet from about 11 to about 24 days of age.

4. The method of claim 1 or 2, wherein the non-viral DNA plasmid vector includes nucleotides that encode the single truncated PRRSV ORF7 protein and have a sequence that has at least 90% identity to the sequence as set forth in SEQ ID NO:3.

5. The method of claim 4, wherein the nucleotides that encode the single truncated PRRSV ORF7 protein have the sequence as set forth in SEQ ID NO:3.

6. The method of claim 1 or 2, wherein the vaccine comprises from 100 ng to 500 µg of the non-viral DNA plasmid vector.

* * * * *

SEQUENCE LISTING

```
<160> NUMBER OF SEQ ID NOS: 18

<210> SEQ ID NO 1
<211> LENGTH: 372
<212> TYPE: DNA
<213> ORGANISM: Artificial Sequence
<220> FEATURE:
<223> OTHER INFORMATION: PRRSV ORF7

<400> SEQUENCE: 1
atgccaaata acaacggcaa gcagcagaag agaaagaagg gggatggcca gccagtcaat      60
cagctgtgcc agatgctggg taagatcatc gctcagcaaa accagtccag aggcaaggga     120
ccgggaaaga aaaataagaa gaaaaacccg gagaagcccc attttcctct agcgactgaa     180
gatgatgtca gacatcactt tacccctagt gagcggcaat tgtgtctgtc gtcaatccag     240
accgccttta atcaaggcgc tgggacttgc accctgtcag attcagggag gataagttac     300
actgtggagt ttagtttgcc tacgcatcat actgtgcgcc tgatccgcgt cacagcatca     360
ccctcagcat ga                                                         372

<210> SEQ ID NO 2
<211> LENGTH: 123
<212> TYPE: PRT
<213> ORGANISM: Artificial Sequence
<220> FEATURE:
<223> OTHER INFORMATION: PRRSV ORF7 translation

<400> SEQUENCE: 2

Met Pro Asn Asn Asn Gly Lys Gln Gln Lys Arg Lys Lys Gly Asp Gly
1               5                   10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60
```

```
His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
            115                 120
```

<210> SEQ ID NO 3
<211> LENGTH: 339
<212> TYPE: DNA
<213> ORGANISM: Artificial Sequence
<220> FEATURE:
<223> OTHER INFORMATION: PRRSV modified truncated ORF7 (ORF

```
<211> LENGTH: 34
<212> TYPE: DNA
<213> ORGANISM: Artificial Sequence
<220> FEATURE:
<223> OTHER INFORMATION: ORF7 US-R primer

<400> SEQUENCE: 6
aaaaaagaat tctcatgctg agggtgatgc tgtg                                 34

<210> SEQ ID NO 7
<211> LENGTH: 34
<212> TYPE: DNA
<213> ORGANISM: Artificial Sequence
<220> FEATURE:
<223> OTHER INFORMATION: US-11R primer

<400> SEQUENCE: 7
aaaaaagaat tctcacacag tatgatgcgt aggc                                 34

<210> SEQ ID NO 8
<211> LENGTH: 4283
<212> TYPE: DNA
<213> ORGANISM: Artificial Sequence
<220> FEATURE:
<223> OTHER INFORMATION: pMASIA plasmid

<400> SEQUENCE: 8
gaattcgagc tcccgggtac catggcatgc atcgatagat ctcgagtcta gactagagct     60
cgctgatcag cctcgactgt gccttctagt tgccagccat ctgttgtttg cccctccccc    120
gtgccttcct tgaccctgga aggtgccact cccactgtcc tttcctaata aaatgaggaa    180
attgcatcgc attgtctgag taggtgtcat tctattctgg ggggtggggt ggggcaggac    240
agcaaggggg aggattggga agacaatagc aggcatgctg gggaaggcct cggactagtg    300
gcgtaatcat ggtcatagct gtttcctgtg tgaaattgtt atccgctcac aattccacac    360
aacatacgag ccgcggaagc ataaagtgta agcctggggg tgcctaatga gtgagctaac    420
tcacattaat tgcgttgcgc tcactgcccg ctttccagtc gggaaacctg tcgtgccagc    480
tgcattaatg aatcggccaa cgcgcgggga gaggcggttt gcgtattggg cgctcttccg    540
cttcctcgct cactgactcg ctgcgctcgg tcgttcggct gcggcgagcg gtatcagctc    600
actcaaaggc ggtaatacgg ttatccacag aatcagggga taacgcagga agaacatgt    660 gagcaaaagg ccagcaaaag gccaggaacc gtaaaaaggc cgcgttgctg gcgtttttcc    720
ataggctccg ccccccctgac gagcatcaca aaaatcgacg ctcaagtcag aggtggcgaa    780
acccgacagg actataaaga taccaggcgt ttccccctgg aagctccctc gtgcgctctc    840
ctgttccgac cctgccgctt accggatacc tgtccgcctt ctcccttcg ggaagcgtgg    900 cgctttctca tagctcacgc tgtaggtatc tcagttcggt gtaggtcgtt cgctccaagc    960
tgggctgtgt gcacgaaccc cccgttcagc ccgaccgctg cgccttatcc ggtaactatc   1020
gtcttgagtc aacccggta agacacgact tatcgccact ggcagcagcc actggtaaca   1080
ggattagcag agcgaggtat gtaggcggtg ctacagagtt cttgaagtgg tggcctaact   1140
acggctacac tagaagaaca gtatttggta tctgcgctct gctgaagcca gttaccttcg   1200
gaaaaagagt tggtagctct tgatccggca acaaaccac cgctggtagc ggtggttttt   1260
ttgtttgcaa gcagcagatt acgcgcagaa aaaaaggatc tcaagaagat cctttgatct   1320
tttctacggg gtctgacgct cagtggaacg aaaactcacg ttaagggatt ttggtcatga   1380
gctgtcgttg tgtcgtcaag tcagcgtaat gctctgccag tgttacaacc aattaaccaa   1440
```

```
ttctgattag aaaaactcat cgagcatcaa atgaaactgc aatttattca tatcaggatt    1500
atcaatacca tatttttgaa aaagtcgttt ctgtaatgaa ggagaaaact caccaaggca    1560
gttccatagg atggcaagat cctggtatcg atctgcgatt ccaactcgtc caacatcaat    1620
acaacctatt aatttcccct cgtcaaaaat aaggttatca agtgagaaat caccatgagt    1680
gacgactgaa tctggtgaga atggcaaaag tttatgcatt tctttccaga cttgttcaac    1740
aggccagcca ttacgctcgt catcaaaatc actcgcatca accaaaccat tattcattcg    1800
tgattgcgcc tgagcgagac gaaatacgcg atcgctgtta aaaggacaat tacaaacagg    1860
aatcgaatgc aaacgtctca ggaacactgc cagcgcatca acaatatttt cacctgaatc    1920
aggatattct tctaatacct ggaatgctgt ttttccaggg atcgcagtgg tgagtaacca    1980
tgcatcatca ggagtacgta taaaatgctt gatggtggga agaggcataa attctgtcag    2040
ccagtttagt ctgaccatct catctgtaac atcattggca acgctacctt gccatgttt     2100 cagaaacaac tctggcgcat ctggcttccc atacaagcga tagattgtcg cacctgattg    2160
ccctacatta tcgcgagccc atttataccc atataaatca gcatccatgt tggaatttaa    2220
tcgtggcctc gacgtttccc gttgaatatg gctcataaca ccccttgtat tactgtttat    2280
gtaagcagac agttttattg ttcatgatga tatattttta tcttgtgcaa tgtaacatca    2340
gagattttga gacacaacgt ggctttcccc ccccccccca tgacattaac ctataaaaat    2400
aggcgtatca cgaggcccta ttttaaattc gaaagtactg gacctgttaa cacgccattc    2460
gccattcagg ctgcgcaact gttgggaagg gcgatcggtg cgggcctctt cgctattacg    2520
ccagctggcg aaagggggat gtgctgcaag gcgattaagt tgggtaacgc cagggttttc    2580
ccagtcacga cgttgtaaaa cgacggccag tgaattgtaa tacgactcac tatagggcga    2640
attggggatc gatccactag ttctagatcc gatgtacggg ccagatatac gcgttgacat    2700
tgattattga ctagttatta atagtaatca attacgggt cattagttca tagcccatat    2760
atggagttcc gcgttacata acttacggta atggcccgc ctggctgacc gcccaacgac    2820
ccccgcccat tgacgtcaat aatgacgtat gttcccatag taacgccaat agggactttc    2880
cattgacgtc aatgggtgga gtatttacgg taaactgccc acttggcagt acatcaagtg    2940
tatcatatgc caagtacgcc ccctattgac gtcaatgacg gtaaatggcc cgcctggcat    3000
tatgcccagt acatgacctt atgggacttt cctacttggc agtacatcta cgtattagtc    3060
atcgctatta ccatggtgat gcggttttgg cagtacatca atgggcgtgg atagcggttt    3120
gactcacggg gatttccaag tctccacccc attgacgtca atgggagttt gttttggcac    3180
caaaatcaac gggactttcc aaaatgtcgt aacaactccg ccccattgac gcaaatgggc    3240
ggtaggcgtg tacggtggga ggtctatata agcagagctc tctggctaac tagagaaccc    3300
actgcttact ggcttatcga aattgcggcc gggaacggtg cattggaacg cggattcccc    3360
gtgccaagag tgacgtaagt accgcctata gactctatag gcacacccct ttggctctta    3420
tgcatgctat actgtttttg gcttggggcc tatacacccc cgctccttat gctataggtg    3480
atggtatagc ttagcctata ggtgtgggtt attgaccatt attgaccact cccctattgg    3540
tgacgatact ttccattact aatccataac atggctcttt gccacaacta tctctattgg    3600
ctatatgcca atactctgtc cttcagagac tgacacggac tctgtatttt tacaggatgg    3660
ggtcccattt attatttaca aattcacata tacaacaacg ccgtccccg tgcccgcagt    3720 ttttattaaa catagcgtgg gatctccacg cgaatctcgg gtacgtgttc cggacatggg    3780
```

-continued

| | |
|---|---|
| ctcttctccg gtagcggcgg agcttccaca tccgagccct ggscccatgc ctccagcggc | 3840 |
| tcatggtcgc tcggcagctc cttgctccta acagtggagg ccagacttag gcacagcaca | 3900 |
| atgcccacca ccaccagtgt gccgcacaag gccgtggcgg tagggtatgt gtctgaaaat | 3960 |
| gagctcggag attgggctcg caccgtgacg cagatggaag acttaaggca gcggcagaag | 4020 |
| aagatgcagg cagctgagtt gttgtattct gataagagtc agaggtaact cccgttgcgg | 4080 |
| ttctgttaac ggtggagggc agtgtagtct gagcagtact cgttgctgcc gcgcgcgcca | 4140 |
| ccagacataa tagctgacag actaacagac tgttcctttc catgggtctt ttctgcagtc | 4200 |
| accgtcgtcg acacgtgtga tcagatgact ctctagacca ggcgcctgga tccatatgac | 4260 |
| gtcgacgcgt ctgcagaagc ttc | 4283 |

<210> SEQ ID NO 9
<211> LENGTH: 4655
<212> TYPE: DNA
<213> ORGANISM: Artificial Sequence
<220> FEATURE:
<223> OTHER INFORMATION: pORF7 plasmid

<400> SEQUENCE: 9

| | |
|---|---|
| gaattcatgc caaataacaa cggcaagcag cagaagagaa agaaggggga tggccagcca | 60 |
| gtcaatcagc tgtgccagat gctgggtaag atcatcgctc agcaaaacca gtccagaggc | 120 |
| aagggaccgg gaaagaaaaa taagaagaaa aacccggaga agccccattt tcctctagcg | 180 |
| actgaagatg atgtcagaca tcactttacc cctagtgagc ggcaattgtg tctgtcgtca | 240 |
| atccagaccg cctttaatca aggcgctggg acttgcaccc tgtcagattc agggaggata | 300 |
| agttacactg tggagtttag tttgcctacg catcatactg tgcgcctgat ccgcgtcaca | 360 |
| gcatcaccct cagcgtgaga gctcccgggt accatggcat gcatcgatag atctcgagtc | 420 |
| tagactagag ctcgctgatc agcctcgact gtgccttcta gttgccagcc atctgttgtt | 480 |
| tgcccctccc ccgtgccttc cttgaccctg gaaggtgcca ctcccactgt cctttcctaa | 540 |
| taaaatgagg aaattgcatc gcattgtctg agtaggtgtc attctattct ggggggtggg | 600 |
| gtggggcagg acagcaaggg ggaggattgg gaagacaata gcaggcatgc tggggaaggc | 660 |
| ctcggactag tggcgtaatc atggtcatag ctgtttcctg tgtgaaattg ttatccgctc | 720 |
| acaattccac acaacatacg agccgcgaa gcataaagtg taaagcctgg ggtgcctaat | 780 |
| gagtgagcta actcacatta attgcgttgc gctcactgcc cgctttccag tcgggaaacc | 840 |
| tgtcgtgcca gctgcattaa tgaatcggcc aacgcgcggg gagaggcggt ttgcgtattg | 900 |
| ggcgctcttc cgcttcctcg ctcactgact cgctgcgctc ggtcgttcgg ctgcggcgag | 960 |
| cggtatcagc tcactcaaag gcggtaatac ggttatccac agaatcaggg gataacgcag | 1020 |
| gaaagaacat gtgagcaaaa ggccagcaaa aggccaggaa ccgtaaaaag gccgcgttgc | 1080 |
| tggcgttttt ccataggctc cgcccccctg acgagcatca aaaaatcga cgctcaagtc | 1140 |
| agaggtggcg aaacccgaca ggactataaa gataccaggc gtttccccct ggaagctccc | 1200 |
| tcgtgcgctc tcctgttccg accctgccgc ttaccggata cctgtccgcc tttctccctt | 1260 |
| cgggaagcgt ggcgctttct catagctcac gctgtaggta tctcagttcg gtgtaggtcg | 1320 |
| ttcgctccaa gctgggctgt gtgcacgaac cccccgttca gcccgaccgc tgcgccttat | 1380 |
| ccggtaacta tcgtcttgag tccaacccgg taagacacga cttatcgcca ctggcagcag | 1440 |
| ccactggtaa caggattagc agagcgaggt atgtaggcgg tgctacagag ttcttgaagt | 1500 |
| ggtggcctaa ctacggctac actagaagaa cagtatttgg tatctgcgct ctgctgaagc | 1560 |

```
cagttacctt cggaaaaaga gttggtagct cttgatccgg caaacaaacc accgctggta   1620
gcggtggttt ttttgtttgc aagcagcaga ttacgcgcag aaaaaagga tctcaagaag   1680 atcctttgat cttttctacg gggtctgacg ctcagtggaa cgaaaactca cgttaaggga   1740
ttttggtcat gagctgtcgt tgtgtcgtca agtcagcgta atgctctgcc agtgttacaa   1800
ccaattaacc aattctgatt agaaaaactc atcgagcatc aaatgaaact gcaatttatt   1860
catatcagga ttatcaatac catatttttg aaaaagtcgt ttctgtaatg aaggagaaaa   1920
ctcaccaagg cagttccata ggatggcaag atcctggtat cgatctgcga ttccaactcg   1980
tccaacatca atacaaccta ttaatttccc ctcgtcaaaa ataaggttat caagtgagaa   2040
atcaccatga gtgacgactg aatctggtga aatggcaaa agtttatgca tttctttcca   2100
gacttgttca acaggccagc cattacgctc gtcatcaaaa tcactcgcat caaccaaacc   2160
attattcatt cgtgattgcg cctgagcgag acgaaatacg cgatcgctgt taaaaggaca   2220
attacaaaca ggaatcgaat gcaaacgtct caggaacact gccagcgcat caacaatatt   2280
ttcacctgaa tcaggatatt cttctaatac ctggaatgct gttttttccag ggatcgcagt   2340 ggtgagtaac catgcatcat caggagtacg tataaaatgc ttgatggtgg gaagaggcat   2400
aaattctgtc agccagttta gtctgaccat ctcatctgta acatcattgg caacgctacc   2460
tttgccatgt ttcagaaaca actctggcgc atctggcttc ccatacaagc gatagattgt   2520
cgcacctgat tgccctacat tatcgcgagc ccatttatac ccatataaat cagcatccat   2580
gttgaatttt aatcgtggcc tcgacgtttc ccgttgaata tggctcataa cacccccttgt   2640 attactgttt atgtaagcag acagttttat tgttcatgat gatatatttt tatcttgtgc   2700
aatgtaacat cagagatttt gagacacaac gtggctttcc ccccccccc catgacatta   2760 acctataaaa ataggcgtat cacgaggccc tattttaaat tcgaaagtac tggacctgtt   2820
aacacgccat tcgccattca ggctgcgcaa ctgttgggaa gggcgatcgg tgcgggcctc   2880
ttcgctatta cgccagctgg cgaaaggggg atgtgctgca aggcgattaa gttgggtaac   2940
gccagggttt tcccagtcac gacgttgtaa aacgacggcc agtgaattgt aatacgactc   3000
actatagggc gaattgggga tcgatccact agttctagat ccgatgtacg gccagatat   3060 acgcgttgac attgattatt gactagttat taatagtaat caattacggg gtcattagtt   3120
catagcccat atatggagtt ccgcgttaca taacttacgg taaatggccc gcctggctga   3180
ccgcccaacg accccgccc attgacgtca ataatgacgt atgttcccat agtaacgcca   3240
atagggactt tccattgacg tcaatgggtg gagtatttac ggtaaactgc ccacttggca   3300
gtacatcaag tgtatcatat gccaagtacg cccctattg acgtcaatga cggtaaatgg   3360
cccgcctggc attatgccca gtacatgacc ttatgggact ttcctacttg gcagtacatc   3420
tacgtattag tcatcgctat taccatggtg atgcggtttt ggcagtacat caatgggcgt   3480
ggatagcggt ttgactcacg gggatttcca agtctccacc ccattgacgt caatgggagt   3540
ttgttttggc accaaaatca acgggacttt ccaaaatgtc gtaacaactc cgccccattg   3600
acgcaaatgg gcggtaggcg tgtacggtgg gaggtctata taagcagagc tctctggcta   3660
actagagaac ccactgctta ctggcttatc gaaattgcgg ccgggaacgg tgcattggaa   3720
cgcggattcc ccgtgccaag agtgacgtaa gtaccgccta tagactctat aggcacaccc   3780
ctttggctct tatgcatgct atactgtttt tggcttgggg cctatacacc cccgctcctt   3840
atgctatagg tgatggtata gcttagccta taggtgtggg ttattgacca ttattgacca   3900
```

| | |
|---|---:|
| ctcccctatt ggtgacgata ctttccatta ctaatccata acatggctct ttgccacaac | 3960 |
| tatctctatt ggctatatgc caatactctg tccttcagag actgacacgg actctgtatt | 4020 |
| tttacaggat ggggtcccat ttattattta caaattcaca tatacaacaa cgccgtcccc | 4080 |
| cgtgcccgca gtttttatta aacatagcgt gggatctcca cgcgaatctc gggtacgtgt | 4140 |
| tccggacatg ggctcttctc cggtagcggc ggagcttcca catccgagcc ctggscccat | 4200 |
| gcctccagcg gctcatggtc gctcggcagc tccttgctcc taacagtgga ggccagactt | 4260 |
| aggcacagca caatgcccac caccaccagt gtgccgcaca aggccgtggc ggtagggtat | 4320 |
| gtgtctgaaa atgagctcgg agattgggct cgcaccgtga cgcagatgga agacttaagg | 4380 |
| cagcggcaga agaagatgca ggcagctgag ttgttgtatt ctgataagag tcagaggtaa | 4440 |
| ctcccgttgc ggttctgtta acggtggagg cagtgtagt ctgagcagta ctcgttgctg | 4500 |
| ccgcgcgcgc caccagacat aatagctgac agactaacag actgttcctt tccatgggtc | 4560 |
| ttttctgcag tcaccgtcgt cgacacgtgt gatcagatga ctctctagac caggcgcctg | 4620 |
| gatccatatg acgtcgacgc gtctgcagaa gcttc | 4655 |

<210> SEQ ID NO 10
<211> LENGTH: 4622
<212> TYPE: DNA
<213> ORGANISM: Artificial Sequence
<220> FEATURE:
<223> OTHER INFORMATION: pORF7t plasmid

<400> SEQUENCE: 10

| | |
|---|---:|
| gaattcatgc caaataacaa cggcaagcag cagaagagaa agaagggga tggccagcca | 60 |
| gtcaatcagc tgtgccagat gctgggtaag atcatcgctc agcaaaacca gtccagaggc | 120 |
| aagggaccgg gaaagaaaaa taagaagaaa aacccggaga agccccatttt cctctagcg | 180 |
| actgaagatg atgtcagaca tcactttacc cctagtgagc ggcaattgtg tctgtcgtca | 240 |
| atccagaccg cctttaatca aggcgctggg acttgcaccc tgtcagattc agggaggata | 300 |
| agttacactg tggagtttag tttgcctacg catcatactg tgtgagagct cccgggtacc | 360 |
| atggcatgca tcgatagatc tcgagtctag actagagctc gctgatcagc ctcgactgtg | 420 |
| ccttctagtt gccagccatc tgttgtttgc ccctcccccg tgccttcctt gaccctggaa | 480 |
| ggtgccactc ccactgtcct ttcctaataa aatgaggaaa ttgcatcgca ttgtctgagt | 540 |
| aggtgtcatt ctattctggg gggtggggtg ggcaggaca gcaaggggga ggattgggaa | 600 |
| gacaatagca ggcatgctgg ggaaggcctc ggactagtgg cgtaatcatg gtcatagctg | 660 |
| tttcctgtgt gaaattgtta tccgctcaca attccacaca atatacgagc cgcggaagca | 720 |
| taaagtgtaa agcctggggt gcctaatgag tgagctaact cacattaatt gcgttgcgct | 780 |
| cactgcccgc tttccagtcg ggaaacctgt cgtgccagct gcattaatga atcggccaac | 840 |
| gcgcggggag aggcggtttg cgtattgggc gctcttccgc ttcctcgctc actgactcgc | 900 |
| tgcgctcggt cgttcggctg cggcgagcgg tatcagctca ctcaaaggcg gtaatacggt | 960 |
| tatccacaga atcaggggat aacgcaggaa agaacatgtg agcaaaaggc cagcaaaagg | 1020 |
| ccaggaaccg taaaaaggcc gcgttgctgg cgttttttcca taggctccgc ccccctgacg | 1080 |
| agcatcacaa aaatcgacgc tcaagtcaga ggtggcgaaa cccgacagga ctataaagat | 1140 |
| accaggcgtt tccccctgga agctccctcg tgcgctctcc tgttccgacc ctgccgctta | 1200 |
| ccggatacct gtccgccttt ctcccttcgg aagcgtggc gctttctcat agctcacgct | 1260 |
| gtaggtatct cagttcggtg taggtcgttc gctccaagct gggctgtgtg cacgaacccc | 1320 |

```
ccgttcagcc cgaccgctgc gccttatccg gtaactatcg tcttgagtcc aacccggtaa    1380
gacacgactt atcgccactg gcagcagcca ctggtaacag gattagcaga gcgaggtatg    1440
taggcggtgc tacagagttc ttgaagtggt ggcctaacta cggctacact agaagaacag    1500
tatttggtat ctgcgctctg ctgaagccag ttaccttcgg aaaaagagtt ggtagctctt    1560
gatccggcaa acaaaccacc gctggtagcg gtggttttt tgtttgcaag cagcagatta     1620
cgcgcagaaa aaaggatct caagaagatc ctttgatctt ttctacgggg tctgacgctc      1680
agtggaacga aaactcacgt taagggattt tggtcatgag ctgtcgttgt gtcgtcaagt    1740
cagcgtaatg ctctgccagt gttacaacca attaaccaat tctgattaga aaaactcatc    1800
gagcatcaaa tgaaactgca atttattcat atcaggatta tcaataccat attttttgaaa   1860 aagtcgtttc tgtaatgaag gagaaaactc accaaggcag ttccatagga tggcaagatc    1920
ctggtatcga tctgcgattc caactcgtcc aacatcaata caacctatta atttcccctc    1980
gtcaaaaata aggttatcaa gtgagaaatc accatgagtg acgactgaat ctggtgagaa    2040
tggcaaaagt ttatgcattt cttttccagac ttgttcaaca ggccagccat tacgctcgtc    2100
atcaaaatca ctcgcatcaa ccaaaccatt attcattcgt gattgcgcct gagcgagacg    2160
aaatacgcga tcgctgttaa aaggacaatt acaaacagga atcgaatgca aacgtctcag    2220
gaacactgcc agcgcatcaa caatattttc acctgaatca ggatattctt ctaatacctg    2280
gaatgctgtt tttccaggga tcgcagtggt gagtaaccat gcatcatcag gagtacgtat    2340
aaaatgcttg atggtgggaa gaggcataaa ttctgtcagc cagtttagtc tgaccatctc    2400
atctgtaaca tcattggcaa cgctacctt tgccatgttt cagaaacaact ctggcgcatc    2460 tggcttccca tacaagcgat agattgtcgc acctgattgc cctacattat cgcgagccca    2520
tttataccca tataaatcag catccatgtt ggaatttaat cgtggcctcg acgtttcccg    2580
ttgaatatgg ctcataacac cccttgtatt actgtttatg taagcagaca gttttattgt    2640
tcatgatgat atatttttat cttgtgcaat gtaacatcag agattttgag acacaacgtg    2700
gctttccccc ccccccccat gacattaacc tataaaaata ggcgtatcac gaggccctat    2760
tttaaattcg aaagtactgg acctgttaac acgccattcg ccattcaggc tgcgcaactg    2820
ttgggaaggg cgatcggtgc gggcctcttc gctattacgc cagctggcga aggggggatg    2880
tgctgcaagg cgattaagtt gggtaacgcc agggttttcc cagtcacgac gttgtaaaac    2940
gacggccagt gaattgtaat acgactcact atagggcgaa ttggggatcg atccactagt    3000
tctagatccg atgtacgggc cagatatacg cgttgacatt gattattgac tagttattaa    3060
tagtaatcaa ttacggggtc attagttcat agcccatata tggagttccg cgttacataa    3120
cttacggtaa atggcccgcc tggctgaccg cccaacgacc cccgcccatt gacgtcaata    3180
atgacgtatg ttcccatagt aacgccaata gggactttcc attgacgtca atgggtggag    3240
tatttacggt aaactgccca cttggcagta catcaagtgt atcatatgcc aagtacgccc    3300
cctattgacg tcaatgacgg taaatggccc gcctggcatt atgcccagta catgacctta    3360
tgggactttc ctacttggca gtacatctac gtattagtca tcgctattac catggtgatg    3420
cggttttggc agtacatcaa tgggcgtgga tagcggtttg actcacgggg atttccaagt    3480
ctccacccca ttgacgtcaa tgggagtttg ttttggcacc aaaatcaacg ggactttcca    3540
aaatgtcgta acaactccgc cccattgacg caaatgggcg gtaggcgtgt acggtgggag    3600
gtctatataa gcagagctct ctggctaact agagaaccca ctgcttactg gcttatcgaa    3660
```

| | | | | |
|---|---|---|---|---|
| attgcggccg | ggaacggtgc | attggaacgc | ggattccccg | tgccaagagt gacgtaagta | 3720 |
| ccgcctatag | actctatagg | cacaccccct | tggctcttat | gcatgctata ctgttttgg | 3780 |
| cttgggcct | atacacccc | gctccttatg | ctataggtga | tggtatagct tagcctatag | 3840 |
| gtgtgggtta | ttgaccatta | ttgaccactc | ccctattggt | gacgatactt tccattacta | 3900 |
| atccataaca | tggctctttg | ccacaactat | ctctattggc | tatatgccaa tactctgtcc | 3960 |
| ttcagagact | gacacggact | ctgtattttt | acaggatggg | gtcccattta ttatttacaa | 4020 |
| attcacatat | acaacaacgc | cgtcccccgt | gcccgcagtt | tttattaaac atagcgtggg | 4080 |
| atctccacgc | gaatctcggg | tacgtgttcc | ggacatgggc | tcttctccgg tagcggcgga | 4140 |
| gcttccacat | ccgagccctg | gscccatgcc | tccagcggct | catggtcgct cggcagctcc | 4200 |
| ttgctcctaa | cagtggaggc | cagacttagg | cacagcacaa | tgcccaccac caccagtgtg | 4260 |
| ccgcacaagg | ccgtggcggt | agggtatgtg | tctgaaaatg | agctcggaga ttgggctcgc | 4320 |
| accgtgacgc | agatgaaga | cttaaggcag | cggcagaaga | agatgcaggc agctgagttg | 4380 |
| ttgtattctg | ataagagtca | gaggtaactc | ccgttgcggt | tctgttaacg gtggagggca | 4440 |
| gtgtagtctg | agcagtactc | gttgctgccg | cgcgcgccac | cagacataat agctgacaga | 4500 |
| ctaacagact | gttcctttcc | atgggtcttt | tctgcagtca | ccgtcgtcga cacgtgtgat | 4560 |
| cagatgactc | tctagaccag | gcgcctggat | ccatatgacg | tcgacgcgtc tgcagaagct | 4620 |
| tc | | | | | 4622 |

<210> SEQ ID NO 11
<211> LENGTH: 21
<212> TYPE: DNA
<213> ORGANISM: Artificial Sequence
<220> FEATURE:
<223> OTHER INFORMATION: pMASIA F primer

<400> SEQUENCE: 11
cagtgtagtc tgagcagtac t         21

<210> SEQ ID NO 12
<211> LENGTH: 4840
<212> TYPE: DNA
<213> ORGANISM: Artificial Sequence
<220> FEATURE:
<223> OTHER INFORMATION: pBAD-ORF7 plasmid

<400> SEQUENCE: 12

| | | | | |
|---|---|---|---|---|
| aagaaaccaa | ttgtccatat | tgcatcagac | attgccgtca | ctgcgtcttt tactggctct | 60 |
| tctcgctaac | caaaccggta | accccgctta | ttaaaagcat | tctgtaacaa agcgggacca | 120 |
| aagccatgac | aaaaacgcgt | aacaaaagtg | tctataatca | cggcagaaaa gtccacattg | 180 |
| attatttgca | cggcgtcaca | ctttgctatg | ccatagcatt | tttatccata agattagcgg | 240 |
| atcctacctg | acgctttta | tcgcaactct | ctactgtttc | tccatacccg ttttttggg | 300 |
| ctagaaataa | ttttgtttaa | ctttaagaag | gagatataca | tacccatggg atctgataaa | 360 |
| attattcatc | tgactgatga | ttcttttgat | actgatgtac | ttaaggcaga tggtgcaatc | 420 |
| ctggttgatt | tctgggcaca | ctggtgcggt | ccgtgcaaaa | tgatcgctcc gattctggat | 480 |
| gaaatcgctg | acgaatatca | gggcaaactg | accgttgcaa | aactgaacat cgatcacaac | 540 |
| ccgggcactg | cgccgaaata | tggcatccgt | ggtatcccga | ctctgctgct gttcaaaaac | 600 |
| ggtgaagtgg | cggcaaccaa | agtgggtgca | ctgtctaaag | gtcagttgaa agagttcctc | 660 |
| gacgctaacc | tggccggctc | tggatccggt | gatgacgatg | acaagctggg aattgatccc | 720 |

```
ttcaccatgc caaataacaa cggcaagcag cagaagagaa agaaggggga tggccagcca    780
gtcaatcagc tgtgccagat gctgggtaag atcatcgctc agcaaaacca gtccagaggc    840
aagggaccgg gaaagaaaaa taagaagaaa aacccggaga agccccattt tcctctagcg    900
actgaagatg atgtcagaca tcactttacc cctagtgagc ggcaattgtg tctgtcgtca    960
atccagaccg cctttaatca aggcgctggg acttgcaccc tgtcagattc agggaggata   1020
agttacactg tggagtttag tttgcctacg catcatactg tgcgcctgat ccgcgtcaca   1080
gcatcaccct cagcgaaggg cgagctcaag cttgaaggta agcctatccc taaccctctc   1140
ctcggtctcg attctacgcg taccggtcat catcaccatc accattgagt taaacggtc    1200
tccagcttgg ctgttttggc ggatgagaga agattttcag cctgatacag attaaatcag   1260
aacgcagaag cggtctgata aaacagaatt tgcctggcgg cagtagcgcg gtggtcccac   1320
ctgaccccat gccgaactca gaagtgaaac gccgtagcgc cgatggtagt gtggggtctc   1380
cccatgcgag agtagggaac tgccaggcat caaataaaac gaaaggctca gtcgaaagac   1440
tgggcctttc gttttatctg ttgtttgtcg gtgaacgctc tcctgagtag gacaaatccg   1500
ccgggagcgg atttgaacgt tgcgaagcaa cggcccggag ggtggcgggc aggacgcccg   1560
ccataaactg ccaggcatca aattaagcag aaggccatcc tgacggatgg cctttttgcg   1620
tttctacaaa ctcttttgtt tattttttcta aatacattca aatatgtatc cgctcatgag   1680
acaataaccc tgataaatgc ttcaataata ttgaaaaagg aagagtatga gtattcaaca   1740
tttccgtgtc gcccttattc ccttttttgc ggcattttgc cttcctgttt ttgctcaccc   1800
agaaacgctg gtgaaagtaa agatgctga agatcagttg ggtgcacgag tgggttacat   1860
cgaactggat ctcaacagcg gtaagatcct tgagagtttt cgccccgaag aacgttttcc   1920
aatgatgagc acttttaaag ttctgctatg tggcgcggta ttatcccgtg ttgacgccgg   1980
gcaagagcaa ctcggtcgcc gcatacacta ttctcagaat gacttggttg agtactcacc   2040
agtcacagaa aagcatctta cggatggcat gacagtaaga gaattatgca gtgctgccat   2100
aaccatgagt gataacactg cggccaactt acttctgaca acgatcggag gaccgaagga   2160
gctaaccgct ttttttgcaca acatggggga tcatgtaact cgccttgatc gttgggaacc   2220
ggagctgaat gaagccatac caaacgacga gcgtgacacc acgatgcctg tagcaatggc   2280
aacaacgttg cgcaaactat taactggcga actacttact ctagcttccc ggcaacaatt   2340
aatagactgg atggaggcgg ataaagttgc aggaccactt ctgcgctcgg cccttccggc   2400
tggctggttt attgctgata atctggagc cggtgagcgt gggtctcgcg gtatcattgc    2460
agcactgggg ccagatggta agccctcccg tatcgtagtt atctacacga cggggagtca   2520
ggcaactatg gatgaacgaa atagacagat cgctgagata ggtgcctcac tgattaagca   2580
ttggtaactg tcagaccaag tttactcata tactttag attgatttaa aacttcattt    2640
ttaatttaaa aggatctagg tgaagatcct ttttgataat ctcatgacca aaatccctta    2700
acgtgagttt tcgttccact gagcgtcaga ccccgtagaa aagatcaaag gatcttcttg    2760
agatcctttt tttctgcgcg taatctgctg cttgcaaaca aaaaaaccac cgctaccagc    2820
ggtggtttgt ttgccggatc aagagctacc aactctttt ccgaaggtaa ctggcttcag    2880
cagagcgcag ataccaaata ctgtccttct agtgtagccg tagttaggcc accacttcaa    2940
gaactctgta gcaccgccta catacctcgc tctgctaatc ctgttaccag tggctgctgc    3000
cagtggcgat aagtcgtgtc ttaccgggtt ggactcaaga cgatagttac cggataaggc    3060
```

```
gcagcggtcg ggctgaacgg ggggttcgtg cacacagccc agcttggagc gaacgaccta    3120
caccgaactg agatacctac agcgtgagct atgagaaagc gccacgcttc ccgaagggag    3180
aaaggcggac aggtatccgg taagcggcag ggtcggaaca ggagagcgca cgagggagct    3240
tccaggggga aacgcctggt atctttatag tcctgtcggg tttcgccacc tctgacttga    3300
gcgtcgattt ttgtgatgct cgtcaggggg cggagccta tggaaaaacg ccagcaacgc     3360 ggcctttta cggttcctgg cctttgtgtt gccttttgct cacatgttct ttcctgcgtt      3420
atcccctgat tctgtggata accgtattac cgcctttgag tgagctgata ccgctcgccg    3480
cagccgaacg accgagcgca gcgagtcagt gagcgaggaa gcggaagagc gcctgatgcg    3540
gtattttctc cttacgcatc tgtgcggtat ttcacaccgc atatggtgca ctctcagtac    3600
aatctgctct gatgccgcat agttaagcca gtatacactc cgctatcgct acgtgactgg    3660
gtcatggctg cgccccgaca cccgccaaca cccgctgacg cgccctgacg gcttgtctg     3720 ctcccggcat ccgcttacag acaagctgtg accgtctccg ggagctgcat gtgtcagagg    3780
ttttcaccgt catcaccgaa acgcgcgagg cagcagatca attcgcgcgc gaaggcgaag    3840
cggcatgcat aatgtgcctg tcaaatggac gaagcaggga ttctgcaaac cctatgctac    3900
tccgtcaagc cgtcaattgt ctgattcgtt accaattatg acaacttgac ggctacatca    3960
ttcacttttt cttcacaacc ggcacggaac tcgctcgggc tggccccggt gcatttttta    4020
aatacccgcg agaaatagag ttgatcgtca aaaccaacat tgcgaccgac ggtggcgata    4080
ggcatccggg tggtgctcaa aagcagcttc gcctggctga tacgttggtc ctcgcgccag    4140
cttaagacgc taatccctaa ctgctggcgg aaaagatgtg acagacgcga cggcgacaag    4200
caaacatgct gtgcgacgct ggcgatatca aaattgctgt ctgccaggtg atcgctgatg    4260
tactgacaag cctcgcgtac ccgattatcc atcggtggat ggagcgactc gttaatcgct    4320
tccatgcgcc gcagtaacaa ttgctcaagc agatttatcg ccagcagctc cgaatagcgc    4380
ccttcccctt gccggcgtt aatgatttgc ccaaacaggt cgctgaaatg cggctggtgc     4440
gcttcatccg ggcgaaagaa ccccgtattg gcaaatattg acggccagtt aagccattca    4500
tgccagtagg cgcgcggacg aaagtaaacc cactggtgat accattcgcg agcctccgga    4560
tgacgaccgt agtgatgaat ctctcctggc gggaacagca aaatatcacc cggtcggcaa    4620
acaaattctc gtccctgatt tttcaccacc ccctgaccgc gaatggtgag attgagaata    4680
taacctttca ttcccagcgg tcggtcgata aaaaaatcga gataaccgtt ggcctcaatc    4740
ggcgttaaac ccgccaccag atgggcatta acgagtatc ccggcagcag gggatcattt      4800
tgcgcttcag ccatactttt catactcccg ccattcagag                           4840
```

<210> SEQ ID NO 13
<211> LENGTH: 15412
<212> TYPE: DNA
<213> ORGANISM: Artificial Sequence
<220> FEATURE:
<223> OTHER INFORMATION: 01NP1-PRRSV - Genbank accession number
      Q056373 - illustrated in FIG. 2

<400> SEQUENCE: 13

```
atgacgtata ggtgttggct ctatgccttg gcatttgtat tgtcgggagc tgtgaccatt      60
ggcacagccc aaaacttgct gcacagaaac acccttctgt gatagcctcc ttcaggggag    120
cttagggttt gtccctagca ccttgcttcc ggagttgcac tgctttacgg tctctccacc    180
cctttaacca tgtctgggat acttgatcgg tgcacgtgta cccccaatgc cagggtgttt    240
```

-continued

```
atggcggagg gccaagtcta ctgcacacga tgcctcagtg cacggtctct ccttcccctg    300
aacctccaag tttctgagct cggggtgcta ggcctattct acaggcccga agagccactc    360
cggtggacgt tgccacgtgc attccccact gttgagtgct ccccgccgg ggcctgctgg     420 cttcctgcaa tctttccaat cgcacgaatg accagtggaa acctgaactt ccaacaaaga    480
atggtacggg tcgcagctga gctttacaga gccggccagc tcacccctgc agtcttgaag    540
gctctacaag tttatgaacg gggttgccgc tggtacccca ttgttggacc tgtccctgga    600
gtggccgttt cgccaattc cctacatgtg agtgataaac ctttcccggg agcaactcac     660
gtgttgacca acctgccgct cccgcagaga cccaagcctg aagacttttg ccccttttgag   720 tgtgctatgg ctactgtcta tgacattggt catgacgccg tcatgtatgt ggccgaaagg    780
aaaatctcct gggcccctcg tggcggggat gaagtgaaat ttgaagctgt ccccggggag    840
ttgaagttga ttgcgaaccg gctccgcacc tccttcccgc cccaccacac agtggacatg    900
tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctacag cggaggctgc aagttaatgg tctccgagca   1140
gtaactgacc taaacggacc tatcgtcgta cagtacttct tcgttaagga gagttggatc   1200
cgccatttga actggcgggg agaacccagc tactctgggt ttgaggacct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg tgcttgtac tagcgccaag    1680 tacgtactta agctggaagg tgagcattgg actgtcactg tgaccctgg gatgtccct     1740 tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttcttgc ccgtcacagc    1980 ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca atcttgaag aatgcttggc caggcttgag    2160
aaagcgcgcc cgcacgcgt aatcgacacc ttctttgatt gggatgttgt gctccctggg    2220
gttgaggcgg caacccagac gatcaagctg ccccaggtca accagtgtcg tgctctggtc   2280
cctgttgtga ctcaaaagtc cttggacaac aactcggtcc cctgaccgc cttttcactg    2340 gctaactact actaccgtgc gcaaggtgac gaagttcgtc accgtgaaag actaaccgcc   2400
gtgctctcca gttggaaaa ggttgttcga gaagaatatg gctcatgcc aaccgagcct     2460 ggtccacggc ccacactgcc acgcgggctc gacgaactca agcccagat ggaggaggac    2520 ttgctgaaac tggctaacgc ccagacgact tcggacatga tggcctgggc agtcgagcag   2580
gttgacctaa aaacttgggt caagaactac ccgcggtgga caccaccacc ccctccgcca   2640
```

```
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agccccttttg atctcccgac cccacctgag    2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccaga acgagcccct ggatttgtct    3060
gcttcctcac agactgaata tgaggcctct cccccagcac cgccgcagag cggggggcgtt    3120
ctgggagtag aggggcatga agctgaggaa accctgagtg aaatctcgga catgtcgggt    3180
aacattaaac ctgcgtccgt gtcatcaagc agctccttgt ccagcgtgag aatcacacgc    3240
ccaaaatact cagctcaagc catcatcgac tcggcgggc cctgcagtgg gcatctccaa    3300
gaggtaaagg aaacatgcct tagtgtcatg cgcgaggcat gtgatgcgac taagcttgat    3360
gaccctgcta cgcaggaatg gctttctcgc atgtgggatc gggtggacat gctgacttgg    3420
cgcaacacgt ctgtttacca ggcgatttgc accttagatg gcaggttaaa gttcctccca    3480
aaaatgatac tcgagacacc gccgccctat ccgtgtgagt ttgtgatgat gcctcacacg    3540
cctgcacctt ccgtaggtgc ggagagcgac cttaccattg gctcagttgc tactgaagat    3600
gttccacgca tcctcgagaa aatagaaaat gtcggcgaga tggccaacca gggacccttg    3660
gccttctccg aggataaacc ggtagatgac caacttgtca cgaccccccg gatatcgtcg    3720
cggaggcctg acgagagcac atcagctccg tccgcaggca caggtggcgc cggctctttt    3780
accgatttgc cgccttcaga tggcgcggat gcggacgggg gggggccgtt tcggacggta    3840
aaaagaaaag ctgaaaggct cttttgaccaa ctgagccgtc aggtttttga cctcgtctcc    3900
catctccctg ttttcttctc acgccttttc taccctggcg gtggttattc tccgggtgat    3960
tggggttttg cagcttttac tctattgtgc ctcttttttat gttacagtta cccagccttt    4020
ggtattgctc ccctcttggg tgtgttttct gggtcttctc ggcgcgttcg aatgggggtt    4080
tttggctgct ggttggcttt tgctgttggt ctgttcaagc ctgtgtccga cccagtcggc    4140
gctgcttgtg agtttgactc gccagagtgt agaaacatcc ttcattcttt tgagcttctc    4200
aaaccttggg accctgttcg cagccttgtt gtgggcccg tcggtctcgg tcttgccatt    4260
cttggcaggt tactgggcgg ggcacgctgc atctggcact ttttgcttag gcttggcatt    4320
gttgcagact gtatcttggc tggagcttac gtgcttctc aaggtaggtg taaaaagtgc    4380
tggggatctt gtataagaac tgctcctaat gaggtcgctt ttaacgtgtt cctttcaca    4440
cgtgcgacca ggtcgtcact tatcgacctg tgcgatcggt tttgtgcgcc aaaaggaatg    4500
gacccccattt ttctcgccac tgggtggcgc gggtgctggg ccggccgaag ccccattgag    4560
caaccctctg aaaaacccat cgcgtttgcc caattggatg aaaagaagat tacggctagg    4620
actgtggtcg cccagcctta tgaccccaac caagccgtaa agtgcttgcg ggtattgcag    4680
gcgggtgggg cgatggtggc taaggcggtc ccaaaagtgg tcaaggtttc cgctgttcca    4740
ttccgagccc ccttctttcc cactggagtg aaagttgacc ctgattgcag ggtcgtggtt    4800
gaccctgaca cttttcactgc agctctccgg tctggctact ccaccacaaa cctcgtcctt    4860
ggtgtagggg actttgcccca gctgaatgga ttaaaaatca ggcaaatttc caagccttca    4920
gggggaggcc cacatctcat ggctgccctg catgttgcct gctcgatggc tctgcacatg    4980
```

```
cttgctggga tttatgtgac tgcggtgggt tcttgcggca ccggcaccaa cgacccgtgg    5040
tgcgctaacc cgtttgccgt ccctggctac ggacctggct ctctctgcac gtccagattg    5100
tgcatttacc aacacggcct taccctgccc ttgacagcac ttgtggcggg attcggtatt    5160
caagaaattg ccttggtcgt tttgattttt gtttccatcg gaggcatggc tcataggttg    5220
agctgtaagg ctgacatgct gtgtgttttg cttgcaattg ccagctatgt ttgggtacct    5280
cttacctggt tgctttgtgt gtttccttgc tggttgcgct gttttctttt gcacccctc     5340 accatcctat ggttggtgtt tttcttgatt tctgtgaata tgccttcagg aatcttggcc    5400
atggtgttgt tggtttctct ttggcttctt ggtcgttata ctaatgttgc tggccttgtc    5460
accccctacg acattcatca ttacaccagt ggccccgcg gtgttgccgc cttggctacc      5520
gcaccagatg ggacctactt ggccgctgtc cgccgcgctg cgttgactgg ccgcaccatg    5580
ctgtttaccc cgtcccagct tgggtctctt cttgagggtg ctttcagaac tcgaaagccc    5640
tcactgaaca ccgtcaatgt gatcgggtcc tccatgggct ctggcggggt gtttaccatc    5700
gacgggaaag tcaagtgcgt aactgccgca catgtcctta cgggcaattc agctcgggtt    5760
tccggggtcg gcttcaatca aatgcttgac tttgacgtaa agggagattt cgctatagct    5820
gattgcccga attggcaagg ggctgccccc aagacccaat tctgcacgga tggatggact    5880
ggccgtgcct attggctaac atcctctggc gtcgaacccg gcgtcattgg aaaaggattc    5940
gccttctgct tcaccgcatg tggcgattcc gggtccccag tgatcaccga ggccggtgag    6000
cttgtcggcg ttcacacggg atcgaataaa caaggggggg gcattgttac gcgcccctca    6060
ggccagtttt gtaatgtggc acccatcaag ctaagcgaat taagtgaatt ctttgctggg    6120
cctaaggtcc cgctcggtga tgtgaaggtc ggcagccaca taattaaaga cataagcgag    6180
gtgccttcag atctttgtgc cttgcttgct gccaaacctg aactggaagg aggcctctcc    6240
accgtccaac ttctttgtgt gtttttttctc ctgtggagaa tgatgggaca tgcctggacg    6300 ccccttggttg ctgtgagttt ctttattttg aatgaggttc tcccagccgt cctggtccgg    6360
agtgttttct cctttggaat gtttgtgctc tcctggctca cgccatggtc tgcgcaagtt    6420
ctgatgatca ggcttctaac agcagctctt aacaggaaca gatggtcact tgccttttttc    6480 agcctcggtg cagtgaccgg ttttgtcgca gatcttgcgg ccactcaggg gcatccgttg    6540
caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
aagtaccgtg gcctgcacca tatccttgtt ggcgatggag tgttctctgc ggctttcttc    6720
ttgagatact tgccgagggg aaagttgagg gaagggtgt cgcaatcctg cggaatgaat     6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactggccca gttggtgcag    6960
gttgataaag ttcgaggtac tttggccaaa cttgaagctt tgctgatac cgtggcacct      7020 caactctcgc ccggtgacat tgttgtcgct ctccgccaca cgcctgtggg cagtatcttc    7080
gacctaaagg ttggtatcac caagcatacc ctccaagcca ttgagaccag agtccttgct    7140
gggtccaaaa tgaccgtggc gcgcgtcgtc gacccgaccc ccacgccccc acccgcaccc    7200
gtgcccatcc ccctcccacc gaaagttctg gagaatggcc ccaacgcttg ggggatgag     7260 gaccgtttga ataagaagaa gaggcgcagg atggaagccc tcggcatcta tgttatgggc    7320
gggaaaaagt accagaaatt ttgggacaag aattccggtg atgtgtttta tgaggaggtc    7380
```

```
cataataaca cagatgagtg ggagtgtctc agagttggcg accctgccga ctttgaccct    7440
gagaagggaa ctctgtgtgg acatgtcacc attgaaaaca aggcttacca tgtttacacc    7500
tccccatctg gtaagaagtt cttggtcccc gtcaacccag agaatggaag agttcaatgg    7560
gaagctgcaa agctttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccagcg acttgacccg ctgtggtcgc ggcggcttgg    7740
ttgttactga acagcggta aaaatagtca aatttcacaa ccggaccttc accctgggac    7800
ctgtgaattt aaaagtggcc agtgaggttg agctaaaaga cgcggttgag cacaaccaac    7860
acccggttgc gagaccgatc gatggtggag ttgtgctcct gcgttccgcg gttccttcgc    7920
ttatagacgt cttgatctcc ggtgctgatg catctcccaa gttacttgcc catcacgggc    7980
cgggaaacac tgggatcgat ggcacgctct gggattttga gtccgaagcc actaaagagg    8040
aagtcgcact cagtgcgcaa ataatacagg cttgtgacat taggcgcggc gacgctcctg    8100
aaattggtct cccttacaag ctgcaccctg ttaggggtaa ccctgagcgg gtgaaaggag    8160
ttctgcagaa tacaaggttt ggagacatac cttacaaaac ccccagtgac actggaagcc    8220
cagtgcacgc ggctgcctgc cttacgccca acgccactcc ggtgactgat gggcgctccg    8280
tcttggccac gaccatgccc cccgggtttg agtgtatatgt accgaccata ccagcgtctg    8340
tccttgatta ccttgactct aggcctgact gccctaaact gctgacagag cacggctgca    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc accccttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaaaga    8820
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcaccccat ggccttctgt tcttacaaga ccagctaaag tttgaggaca    9180
tgctcaaggt tcaaccctg atcgtctatt cggacgacct cgtgctgtat gccgagtctc    9240
ccaccatgcc aaactatcac tggtgggttg aacatctgaa tttgatgctg gggtttcaga    9300
cggacccaaa aagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg gacagctgtg    9480
cttgtttgga gtatgatcct gaatggtttg aagaacttgt agttggaata gcgcagtgcg    9540
cccgcaagga cggctacagc tttcccggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
```

-continued

```
gtccagtcac aatctggtgt ggccatccag cgggttctgg ttcttgtagt gagtgcaaat    9780
cccctgtagg gaaaggcaca agcccttag acgaggtgct ggaacaagtc ccgtataagc     9840
ccccacggac cgttatcatg catgtggagc agggtctcac cccccttgat ccaggtagat    9900
accaaactcg ccgcggatta gtctctgtca ggcgtggaat taggggaaat gaagttgaac    9960
taccagacgg tgattatgct agcaccgcct tgctccctac ctgcaaagag atcaacatgg    10020
tcgctgtcgc ttccaatgta ttgcgcagca ggttcatcat cggcccaccc ggtgctggga    10080
aaacatactg gctccttcaa caggtccagg atggtgatgt tatttacaca ccaactcacc    10140
agaccatgct tgacatgatt agggctttgg ggacgtgccg gttcaacgtc ccggcaggca    10200
caacgctgca attccccgtc ccctcccgca ccggtccgtg ggttcgcatc ctagccggcg    10260
gttggtgtcc tggcaagaat tccttcctag atgaagcagc gtattgcaat caccttgatg    10320
ttttgaggct tcttagtaaa actaccctca cctgtctagg agacttcaag caactccacc    10380
cagtgggttt tgattctcat tgctatgttt ttgacatcat gcctcaaact caactgaaga    10440
ccatctggag gtttggacag aatatctgtg atgccattca gccagattac agggacaaac    10500
tcatgtccat ggtcaacaca acccgtgtga cccacgtgga aaaacctgtc aggtatgggc    10560
aggtcctcac cccctaccac agggaccgag aggacgacgc catcactatt gactccagtc    10620
aaggcgccac attcgatgtg gttacattgc atttgcccac taaagattca ctcaacaggc    10680
aaagagccct tgttgccatc accagggcaa gacacgctat ctttgtgtat gacccacaca    10740
ggcagctgca gggcttgttt gatcttcctg caaaaggcac accgtcaac ctcgcagtgc     10800
accgcgacgg gcagctgatc gtgctggata gaaataacaa agaatgcacg gttgctcagg    10860
ctctaggcaa cggggataaa tttagggcca cagataagcg tgttgtagat tctctccgcg    10920
ccatttgtgc tgatctagaa gggtcgagct ctccgctccc caaggtcgca cacaacttgg    10980
gattttattt ctcacctgat ttaacacagt ttgctaaact cccagtagaa cttgcacctc    11040
actgccccgt ggtgacaacc cagaacaatg aaaagtggcc agatcggctg gttgccagcc    11100
ttcgccctat ccataaatac agccgcgcgt gcatcggtgc cggctatatg gtgggccctt    11160
cggtgtttct aggcactcct ggggtcgtgt catactatct cacaaaattt gttaagggcg    11220
aggctcaatt gcttccggag acggttttca gcaccggccg aattgaggta gactgccggg    11280
aatatcttga tgatcgggag cgagaagttg ctgcgtccct cccacacgct ttcattggcg    11340
acgtcaaagg cactaccgtt ggaggatgtc atcatgtcac ctccagatac ctcccgcgcg    11400
tccttcccaa ggaatcagtt gcggtagtcg gggtttcaag ccccgaaaa gccgcgaaag     11460
cattgtgcac actgacagat gtgtacctcc cagatcttga agcctatctc cacccggaga    11520
cccagtccaa gtgctggaaa atgatgttgg acttcaaaga agttgacta atggtctgga     11580
aagacaaaac agcctatttc caacttgaag gtcgctattt cacctggtat cagcttgcca    11640
gctatgcctc gtacatccgt gttcctgtca actctacggt gtacttggac ccctgcatgg    11700
gccccgccct ttgcaacagg agagtcgtcg ggtccaccca ctgggggct gacctcgcgg     11760
tcaccccctta tgattacggc gctaaaatta tcctgtctag cgcgtaccat ggtgaaatgc    11820
cccccgata caaattctg gcgtgcgcgg agttctcgtt ggatgaccca gttaagtaca      11880
aacatacctg ggggtttgaa tcggatacag cgtatctgta tgagttcacc gggaacggtg    11940
aggactggga ggattacaat gatgcgtttc gtgcgcgcca ggaagggaaa attttacaagg   12000
ccactgccac cagcttgaag ttttattttc ccccgggccc tgtcattgaa ccaactttag    12060
gcctgaattg aaatgaaatg gggtccatgc aaagcctttt ttacaaaatt ggccaacttt    12120
```

```
ttgtggatgc tttcacggag ttcttggtgt ccattgttga tatcattata tttttggcca  12180
ttttgtttgg cttcaccatc gccggttggc tggtggtctt ttgcatcaga ttggtttgct  12240
ccgcgatact ccgtacgcgc tctgccattc actctgagca attacagaag atcttatgag  12300
gcctttcttt cccagtgcca agtggacatt cccacctggg gaactaaaca tcctttgggg  12360
atgctttggc accataaggt gtcaaccctg attgatgaaa tggtgtcgcg tcgaatgtac  12420
cgcatcatgg aaaaagcagg gcaggctgcc tggaaacagg tggtgagcga ggctacgctg  12480
tctcgcatta gtagtttgga tgtggtggct cattttcagc atctagccgc cattgaagcc  12540
gagacctgta aatatttggc ctcccggctg cccatgctac acaacctgcg catgacaggt  12600
tcaaatgtaa ccatagtgta aatagcact ttgaatcagg tgtttgctat ttttccaacc   12660
cctggttccc ggccaaagct tcatgatttt cagcaatggt taatagctgt acattcctcc  12720 atatttcct ctgttgcagc ttcttgtact ctttttgttg tgctgtggtt gcgggttcca   12780
atactacgta ctgtttttgg tttccgctgg ttagggcaa ttttcttc gaactcacag     12840 tgaattacac ggtgtgtcca ccttgcctca cccggcaagc agccacagag atctacgaac  12900
ccggtaggtc tctttggtgc aggatagggt atgaccgatg tgaggaggat gatcatgacg  12960
agctagggtt tatggtaccg cctggcctct ccagcgaagg ccacttgact agtgtttacg  13020
cctggttggc gttcttgtcc ttcagctaca cggcccagtt ccatcccgag atattcggga  13080
tagggaatgt gagtcgagtt tatgttgaca tcaaacatca actcatctgc gccgaacatg  13140 acggcagaa caccaccttg cctcgtcatg acaacatttc agccgtgttt cagacctatt    13200
accaacatca agtcgacggc ggcaattggt ttcacctaga atggcttcgt cccttctttt  13260
cctcgtggtt ggttttaaat gtctcttggt ttctcaggcg ttcgcctgca aaccatgttt  13320
cagttcgagt cttgcagata ttaagaccaa caccaccgca gcggcaggct ttgctgtcct  13380
ccaagacatc agttgcctta ggcatcgcga ctcggcctct gaggcgattc gcaaaatccc  13440
tcagtgccgt acggcgatag ggacacccgt gtatgttacc atcacagcca atgtgacaga  13500
tgagaattat ttacattctt ctgatctcct catgctttct tcttgccttt tctatgcttc  13560
tgagatgagt gaaaagggat ttaaggtggt atttggcaat gtgtcaggca tcgtggctgt  13620
gtgtgtcaat tttaccagct acgtccaaca tgtcaaggag tttacccaac gctccctggt  13680
ggtcgaccat gtgcggttgc tccatttcat gacacctgag accatgaggt gggcaactgt  13740
tttagcctgt cttttttgcca ttctgttggc aatttgaatg tttaagtatg ttggagaaat  13800
gcttgaccgc gggctgttgc tcgcaattgc tttctttgtg gtgtatcgtg ccgttctgtt  13860
ttgctgtgct cgccaacgcc agcaacgaca gcagctccca tctacagctg atttacaact  13920
tgacgctatg tgagctgaat ggcacagact ggctagctaa caaatttgat tgggcagtgg  13980
agagttttgt catcttttcc gttttgactc acattgtctc ctatggtgcc ctcactacca  14040
gccatttcct tgacacagtc gctttagtca ctgtgtctac cgccgggttt gttcacgggc  14100
ggtatgtcct aagtagcatc tacgcggtct gtgccctggc tgcgttgact tgcttcgtca  14160
ttaggtttgc aaagaattgc atgtcctggc gctacgcgtg taccagatat accaacttc   14220 ttctggacac taagggcgga ctctatcgtt ggcggtcgcc tgtcatcata gagaaaaggg  14280
gcaaagttga ggtcgaaggt catctgatcg acctcaaaag agttgtgctt gatggttccg  14340
tggcaacccc tataaccaga gtttcagcgg aacaatgggg tcgtccttag atgacttctg  14400
tcatgatagc acggctccag aaaaggtgct tttggcgttt tctattacct acacgccagt  14460
```

-continued

```
gatgatatat gccctaaagg tgagtcgcgg ccgactgcta gggcttctgc accttttgat    14520
cttcctgaat tgtgcttkca ccttcgggta catgactttc gcgcactttc agagtacaaa    14580
taaggtcgcg ctcactatgg gagcagtagt tgcactcctt tggkgggtgt actcagccat    14640
agaaacctgg aaattcatca cctccagatg ccgtttgtgc ttgctaggcc gcaagtacat    14700
tctggcccct gcccaccacg ttgaaagtgc cgcagggttt catccgattg cggcaaatga    14760
taaccacgca tttgtcgtcc ggcgtcccgg ctccactacg gtcaacggca cattggtgcc    14820
cgggttaaaa agcctcgtgt tgggtggcag aaaagctgtt aaacagggag tggtaaacct    14880
tgtcaaatat gccaaataac aacggcaagc agcagaagag aaagaagggg gatggccagc    14940
cagtcaatca gctgtgccag atgctgggta agatcatcgc tcagcaaaac cagtccagag    15000
gcaagggacc gggaaagaaa aataagaaga aaaacccgga gaagccccat tttcctctag    15060
cgactgaaga tgatgtcaga catcacttta cccctagtga gcggcaattg tgtctgtcgt    15120
caatccagac cgcctttaat caaggcgctg ggacttgcac cctgtcagat tcagggagga    15180
taagttacac tgtggagttt agtttgccta cgcatcatac tgtgcgcctg atccgcgtca    15240
cagcatcacc ctcagcatga tgggctggca ttcttgaggc atctcagtgt atgaattgga    15300
agaatgtatg tgtgaatggca ctgattgaca ttgtgcctct aagtcaccta ttcaattagg    15360
gcgaccgtgt gggggtgaga tttaattggc gagaaccatg cggccgaaat ta            15412
```

<210> SEQ ID NO 14
<211> LENGTH: 123
<212> TYPE: PRT
<213> ORGANISM: Artificial Sequence
<220> FEATURE:
<223> OTHER INFORMATION: US pMA C2

<400> SEQUENCE: 14

```
Met Pro Asn Asn Asn Gly Lys Gln Gln Lys Arg Lys Lys Gly Asp Gly
1               5                   10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120
```

<210> SEQ ID NO 15
<211> LENGTH: 123
<212> TYPE: PRT
<213> ORGANISM: Artificial Sequence
<220> FEATURE:
<223> OTHER INFORMATION: ORF7-pBAD

<400> SEQUENCE: 15

```
Met Pro Asn Asn Asn Gly Lys Gln Gln Lys Arg Lys Lys Gly Asp Gly
1               5                   10                  15
```

```
Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
 65                 70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120

<210> SEQ ID NO 16
<211> LENGTH: 123
<212> TYPE: PRT
<213> ORGANISM: Artificial Sequence
<220> FEATURE:
<223> OTHER INFORMATION: 01NP1.2

<400> SEQUENCE: 16

Met Pro Asn Asn Gly Lys Gln Gln Lys Arg Lys Lys Gly Asp Gly
1               5                   10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
 65                 70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120

<210> SEQ ID NO 17
<211> LENGTH: 123
<212> TYPE: PRT
<213> ORGANISM: Artificial Sequence
<220> FEATURE:
<223> OTHER INFORMATION: 01NP1

<400> SEQUENCE: 17

Met Pro Asn Asn Gly Lys Gln Gln Lys Arg Lys Lys Gly Asp Gly
1               5                   10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
 65                 70                  75                  80
```

```
Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120

<210> SEQ ID NO 18
<211> LENGTH: 3463
<212> TYPE: DNA
<213> ORGANISM: Artificial Sequence
<220> FEATURE:
<223> OTHER INFORMATION: pQE31

<400> SEQUENCE: 18
ctcgagaaat cataaaaaat ttatttgctt tgtgagcgga taacaattat aatagattca      60
attgtgagcg gataacaatt tcacacagaa ttcattaaag gagaaaatt aactatgaga      120 ggatctcacc atcaccatca ccatacggat ccgcatgcga gctcggtacc ccgggtcgac      180
ctgcagccaa gcttaattag ctgagcttgg actcctgttg atagatccag taatgacctc      240
agaactccat ctggatttgt tcagaacgct cggttgccgc cgggcgtttt ttattggtga      300
gaatccaagc tagcttggcg agattttcag gagctaagga agctaaaatg gagaaaaaaa      360
tcactggata taccaccgtt gatatatccc aatggcatcg taaagaacat tttgaggcat      420
ttcagtcagt tgctcaatgt acctataacc agaccgttca gctggatatt acggccttt       480 taaagaccgt aaagaaaaat aagcacaagt tttatccggc ctttattcac attcttgccc      540
gcctgatgaa tgctcatccg gaatttcgta tggcaatgaa agacggtgag ctggtgatat      600
gggatagtgt tcacccttgt tacaccgttt ccatgagcaa aactgaaacg ttttcatcgc      660
tctggagtga ataccacgac gatttccggc agtttctaca catatattcg caagatgtgg      720
cgtgttacgg tgaaaacctg gcctatttcc ctaaagggtt tattgagaat atgtttttcg      780
tctcagccaa tccctgggtg agtttcacca gttttgattt aaacgtggcc aatatggaca      840
acttcttcgc ccccgttttc accatgggca aatattatac gcaaggcgac aaggtgctga      900
tgccgctggc gattcaggtt catcatgccg tttgtgatgg cttccatgtc ggcagaatgc      960
ttaatgaatt acaacagtac tgcgatgagt ggcaggcgg ggcgtaattt ttttaaggca     1020
gttattggtg cccttaaacg cctggggtaa tgactctcta gcttgaggca tcaaataaaa     1080
cgaaaggctc agtcgaaaga ctgggccttt cgttttatct gttgtttgtc ggtgaacgct     1140
ctcctgagta ggacaaatcc gccctctaga gctgcctcgc gcgtttcggt gatgacggtg     1200
aaaacctctg acacatgcag ctcccggaga cggtcacagc ttgtctgtaa gcggatgccg     1260
ggagcagaca agcccgtcag ggcgcgtcag cgggtgttgg cgggtgtcgg ggcgcagcca     1320
tgacccagtc acgtagcgat agcggagtgt atactggctt aactatgcgg catcagagca     1380
gattgtactg agagtgcacc atatgcggtg tgaaataccg cacagatgcg taaggagaaa     1440
ataccgcatc aggcgctctt ccgcttcctc gctcactgac tcgctgcgct cggtcgttcg     1500
gctgcggcga gcggtatcag ctcactcaaa ggcggtaata cggttatcca cagaatcagg     1560
ggataacgca ggaaagaaca tgtgagcaaa aggccagcaa aaggccagga accgtaaaaa     1620
ggccgcgttg ctggcgtttt tccataggct ccgcccccct gacgagcatc acaaaaatcg     1680
acgctcaagt cagaggtggc gaaacccgac aggactataa agataccagg cgtttccccc     1740
tggaagctcc ctcgtgcgct ctcctgttcc gaccctgccg cttaccggat acctgtccgc     1800
```

-continued

```
ctttctccct tcgggaagcg tggcgctttc tcatagctca cgctgtaggt atctcagttc    1860
ggtgtaggtc gttcgctcca agctgggctg tgtgcacgaa cccccgttc agcccgaccg     1920 ctgcgcctta tccggtaact atcgtcttga gtccaacccg gtaagacacg acttatcgcc    1980
actggcagca gccactggta acaggattag cagagcgagg tatgtaggcg gtgctacaga    2040
gttcttgaag tggtggccta actacggcta cactagaagg acagtatttg gtatctgcgc    2100
tctgctgaag ccagttacct tcggaaaaag agttggtagc tcttgatccg gcaaacaaac    2160
caccgctggt agcggtggtt ttttttgtttg caagcagcag attacgcgca gaaaaaaagg   2220
atctcaagaa gatcctttga tcttttctac ggggtctgac gctcagtgga acgaaaactc    2280
acgttaaggg attttggtca tgagattatc aaaaggatc ttcacctaga tccttttaaa    2340
ttaaaaatga agttttaaat caatctaaag tatatatgag taaacttggt ctgacagtta    2400
ccaatgctta atcagtgagg cacctatctc agcgatctgt ctatttcgtt catccatagt    2460
tgcctgactc cccgtcgtgt agataactac gatacgggag ggcttaccat ctggccccag    2520
tgctgcaatg ataccgcgag acccacgctc accggctcca gatttatcag caataaacca    2580
gccagccgga agggccgagc gcagaagtgg tcctgcaact ttatccgcct ccatccagtc    2640
tattaattgt tgccgggaag ctagagtaag tagttcgcca gttaatagtt tgcgcaacgt    2700
tgttgccatt gctacaggca tcgtggtgtc acgctcgtcg tttggtatgg cttcattcag    2760
ctccggttcc caacgatcaa ggcgagttac atgatccccc atgttgtgca aaaagcggt    2820 tagctccttc ggtcctccga tcgttgtcag aagtaagttg gccgcagtgt tatcactcat    2880
ggttatggca gcactgcata attctcttac tgtcatgcca tccgtaagat gcttttctgt    2940
gactggtgag tactcaacca agtcattctg agaatagtgt atgcggcgac cgagttgctc    3000
ttgcccggcg tcaatacggg ataataccgc gccacatagc agaactttaa aagtgctcat    3060
cattggaaaa cgttcttcgg ggcgaaaact ctcaaggatc ttaccgctgt tgagatccag    3120
ttcgatgtaa cccactcgtg cacccaactg atcttcagca tcttttactt tcaccagcgt    3180
ttctgggtga gcaaaaacag gaaggcaaaa tgccgcaaaa aagggaataa gggcgacacg    3240
gaaatgttga atactcatac tcttcctttt tcaatattat tgaagcattt atcagggtta    3300
ttgtctcatg agcggataca tatttgaatg tatttagaaa aataaacaaa taggggttcc    3360
gcgcacattt ccccgaaaag tgccacctga cgtctaagaa accattatta tcatgacatt    3420
aacctataaa aataggcgta tcacgaggcc ctttcgtctt cac                       3463
```